United States Patent
Rich et al.

(10) Patent No.: US 10,519,109 B2
(45) Date of Patent: Dec. 31, 2019

(54) GLYCOPYRRONIUM FATTY ACID SALTS AND METHODS OF MAKING SAME

(71) Applicant: QAAM PHARMACEUTICALS, LLC, Canandaigua, NY (US)

(72) Inventors: Steven A. Rich, Canandaigua, NY (US); Emerich Eisenreich, Claremont, CA (US); Xuejun Karl Liu, Arcadia, CA (US); Bingidimi Itute Mobele, Altamont, NY (US); Satish Goud Puppali, Rancho Cucamonga, CA (US)

(73) Assignee: QAAM PHARMACEUTICALS, LLC, Canandaigua, NY (US)

( * ) Notice: Subject to any disclaimer, the term of this patent is extended or adjusted under 35 U.S.C. 154(b) by 0 days.

(21) Appl. No.: 15/736,662

(22) PCT Filed: Jun. 6, 2016

(86) PCT No.: PCT/US2016/035967
§ 371 (c)(1),
(2) Date: Dec. 14, 2017

(87) PCT Pub. No.: WO2016/204998
PCT Pub. Date: Dec. 22, 2016

(65) Prior Publication Data
US 2018/0179156 A1 Jun. 28, 2018

Related U.S. Application Data

(60) Provisional application No. 62/175,737, filed on Jun. 15, 2015.

(51) Int. Cl.
*C07D 207/12* (2006.01)
*C07C 53/126* (2006.01)
*C07C 57/12* (2006.01)
*C07C 57/03* (2006.01)

(52) U.S. Cl.
CPC .......... *C07D 207/12* (2013.01); *C07C 53/126* (2013.01); *C07C 57/03* (2013.01); *C07C 57/12* (2013.01)

(58) Field of Classification Search
None
See application file for complete search history.

(56) References Cited

U.S. PATENT DOCUMENTS

| | | |
|---|---|---|
| 5,346,906 A | 9/1994 | Baker et al. |
| 5,861,431 A | 1/1999 | Hildebrand et al. |
| 6,063,808 A | 5/2000 | Fabiano et al. |
| 6,204,285 B1 | 3/2001 | Fabiano et al. |
| 6,255,502 B1 | 7/2001 | Penkler et al. |
| 7,091,236 B1 | 8/2006 | Roberts et al. |
| 8,343,467 B2 | 1/2013 | Woehrmann et al. |
| 8,404,701 B2 | 3/2013 | Chase et al. |
| 8,877,768 B2 | 11/2014 | Chase et al. |
| 2004/0082644 A1 | 4/2004 | Korsten |
| 2006/0018839 A1 | 1/2006 | Ieni et al. |
| 2006/0142241 A1 | 6/2006 | Yoo |
| 2011/0086950 A1 | 4/2011 | Changping |
| 2011/0201597 A1 | 8/2011 | Chase et al. |
| 2014/0350281 A1 | 11/2014 | DeMattei et al. |
| 2015/0086640 A1 | 3/2015 | Staniforth et al. |

FOREIGN PATENT DOCUMENTS

| | | |
|---|---|---|
| WO | 2009052353 A2 | 4/2009 |
| WO | 2014091384 A2 | 6/2014 |

OTHER PUBLICATIONS

Ancelin et al., "Non-degenerative mild cognitive impairment in elderly people and use of anticholinergic drugs: longitudinal cohort study", BMJ, doi:10.1136/bmj.38740.439664.DE, 5 pages, 2006.
Aschenbrenner et al., Drug Therapy in Nursing, p. 324, 2009.
Campbell et al., "Use of anticholinergics and the risk of cognitive impairment in an African American population", Neurology, vol. 75, pp. 152-159, 2010.
Carnahan et al., "The Concurrent Use of Anticholinergics and Cholinesterase Inhibitors: Rare Event or Common Practice?", JAGS vol. 52, pp. 2082-2087, 2004.
Chew et al., "Serum Anticholinergic Activity and Cognition in Patients with Moderate-to-Severe Dementia", Am. J. Geriatr. Psychiatry, vol. 13, pp. 535-538, 2005.
Cooke et al., "Glycopyrrolate in Bladder Dysfunction", South African Medical Journal, vol. 63, p. 3, 1983.
Cuvposa (glycopyrrolate) oral solution, Product Information Sheet, pp. 6-15, 2010.
Detrol® LA (tolterodine tartrate) capsules, Product Information Sheet, 12 pages, 2008.
Drinka, "Antimuscarinic Drugs for Overactive Bladder and Their Potential Effects on Cognitive Function in Older Patients", JAGS, vol. 54, pp. 1004-1005, 2006.
Douaud et al., "Preventing Alzheimer's disease-related gray matter atrophy by B-vitamin treatment", PNAS, vol. 110, pp. 9523-9528, 2013.
Enablex® (darifenacin) tablets, Product Information Sheet, 16 pages, 2010.
Exelon® Capsule, Product Information Sheet, Novartis, 4 pages, 2002.

(Continued)

*Primary Examiner* — Kamal A Saeed
(74) *Attorney, Agent, or Firm* — Brown & Michaels, PC

(57) ABSTRACT

Novel glycopyrronium fatty acid salts have been developed. Bi-phasic reaction conditions enable the desired counterion exchange reactions between glycopyrronium bromide and fatty acid salts of alkali metals and alkaline earth metals in methods to form glycopyrronium fatty acid salts. In preferred embodiments, an excess of the free fatty acid in the reaction mixture stabilizes the glycopyrronium fatty acid salt and reduces the formation of the impurity, Acid A. In some preferred embodiments, between 0.2 and 1.2 molar equivalent of excess free fatty acid is added to the reaction mixture. In another embodiment, approximately 1.2 molar equivalent of excess free fatty acid is added to the reaction mixture.

20 Claims, 38 Drawing Sheets

(56) References Cited

OTHER PUBLICATIONS

Exelon® Patch (rivastigmine transdermal system), Product Information Sheet, LTS Lohmann Therapie Systems AG, 12 pages, 2000.
Ferguson, "Modulation of lymphatic smooth muscle contraction responses by the endothelium", Journal of Surgical Research, vol. 52, pp. 359-363, 1992.
Gish et al., "Memorandum: Age-dependent manifestations of central anticholinergic effects", Department of Health and Human Services Public Health Service Food and Drug Administration Center for Drug Evaluation and Research, 30 pages, 2007.
Hashimoto et al., "Urinary Incontinence: an Unrecognised Adverse Effect with Donepezil", The Lancet, vol. 356, p. 568, 2000.
Iliff et al., "A Paravascular Pathway Facilitates CSF Flow Through the Brain Parenchyma and the Clearance of Interstitial Solutes, Including Amyloid ß". Sci. Transl. Med., vol. 4(147):147ra111, 11 pages, 2012.
Janos et al., "Overactive bladder medicines and cognitive testing", Int. J. Clin. Pract., vol. 62, pp. 1637-1642, 2008.
Jewart et al., "Cognitive, Behavioral and Physiological Changes in Alzheimer Disease Patients as a Function of Incontinence Medications", Am. J. Geriatr. Psychiatry, vol. 13, pp. 324-328, 2005.
Jhee et al., "Centrally Acting Antiemetics Mitigate Nausea and Vomiting in Patients with Alzheimer's Disease Who Receive Rivastigmine", Clinical Neuropharmacology, vol. 25, pp. 122-123, 2002.
Kay et al., "Antimuscarinic Drugs for Overactive Bladder and Their Potential Effects on Cognitive Function in Older Patients", JAGS, vol. 53, pp. 2195-2201, 2005.
Kay et al., "Preserving cognitive function for patients with overactive bladder: evidence for a differential effect with darifenacin", Int. J. Clin. Pract., vol. 62, pp. 1792-1800, 2008.
Khullar et al., "Prevalence of Faecal Incontinence among Women with Urinary Incontinence", Br. J. Obstet. Gynaecol., vol. 105, pp. 1211-1213, 1998.
Levin et al., "Direct Measurement of the Anticholinergic Activity of a Series of Pharmacological Compounds of the Canine and Rabbit Urinary Bladder", J. Urology, vol. 128, pp. 396-398, 1982.
Lopez et al., "Predictors of progression in patients with AD and Lewy bodies", Neurology, vol. 54, pp. 1774-1779, 2000.
Medline Plus, "Stress incontinence: MedlinePluss Medical Encyclopedia", available at http://www.nlm.nih.gov/medlineplus/ency/article/000891.htm, 5 pages, 2009.
Oken, "Antihistamines, a Possible Risk Factor for Alzheimer's Disease", Medical Hypotheses, vol. 44, pp. 47-48, 1995.
Olichney et al., "Cognitive Decline is Faster in Lewy Body Variant than in Alzheimer's Disease", Neurology, vol. 51, pp. 351-357, 1998.
Ono Pharmaceutical Co., Ltd., "Launch of Rivistach® Patch, for the Treatment of Dementia of Alzheimer's Type", 2 pages, 2011.
Ray et al. "Central Anticholinergic Hypersensitivity in Aging", Journal of Geriatric Psychiatry and Neurology, vol. 5, pp. 72-77, 1992.
Robinul® glycopyrrolate tablets, Product Information Sheet, 4 pages, 2010.
Roe et al., "Use of Anticholinergic Medications by Older Adults with Dementia", JAGS, vol. 50, pp. 836-842, 2002.
Rudolph et al., "The Anticholinergic Risk Scale and Anticholinergic Adverse Effects in Older Persons", Arch. Intern. Med., vol. 168, pp. 508-513, 2008.
Sanctura® (trospium chloride), Product Information Sheet, 12 pages, 2011.
Sink et al., "Dual Use of Bladder Anticholinergics and Cholinesterase Inhibitors: Long-Term Functional and Cognitive Outcomes", JAGS, vol. 56, pp. 847-853, 2008.
Terry et al., "The Cholinergic Hypothesis of Age and Alzheimer's Disease-Related Cognitive Deficits: Recent Challenges and Their Implications for Novel Drug Development", JPET, vol. 306, pp. 821-827, 2003.
Tsao et al., "Transient Memory Impairment and Hallucinations Associated with Tolterodine Use", New England Journal of Medicine, vol. 349, pp. 2274-2275, 2003.
Van Eijk et al., "Effect of rivastigmine as an adjunct to usual care with haloperidol on duration of delirium and mortality in critically ill patients: a multicentre, double-blind, placebo-controlled randomised trial", Lancet, vol. 376, pp. 1829-1837, 2010.
Vesicare® (solifenacin succinate) tablets, Product Information Sheet, 16 pages, 2010.
Williams et al., "Survival and mortality differences between dementia with Lewy bodies vs Alzheimer disease", Neurology, vol. 67, pp. 1935-1941, 2006.
Verdejo et al. Anales de Medicina, 1992, vol. 9, No. 3, abstract only (cited by Examiner on Dec. 10, 2014 in U.S. Appl. No. 13/325,371).
Collomb et al., "Composition of fatty acids in cow's milk fat produced in the lowlands, mountains and highlands of Switzerland using high-resolution gas chromatography," International Dairy Journal 12 (2002) 649-659.
Pubchem Open Chemistry Database, 2005, Compound Summary for CID 11693, Glycopyrrolate, retrieved from https://pubchem.ncbi.nlm.nih.gov/compound/glycopyrrolate.
Simard et al., "Locating high-affinity fatty acid-binding sites on albumin by x-ray crystallography and NMR spectroscopy," PNAS, 2005, 102(50), 17958-17963.
Alcalde et al. "A Simple Halide-to-Anion Exchange Method for Heteroaromatic Salts and Ionic Liquids", Laboratory of Organic Chemistry, Faculty of Pharmacy, University of Barcelona; Apr. 2012.
International Search Report for PCT/US2016/035967 dated Sep. 2, 2016.
Partial European Search Report for PCT/US2016/035967 dated Mar. 26, 2018.
Furniss et al. "Experimental Techniques 2.22 Solvent Extraction", Vogel's Textbook of Practical Organic Chemistry; Pearson Pretice Hall; pp. 156-160; 1989.
Langguth et al. "Lipophilisation of Hydrophilic Compounds"; Arzneim-Forsch/Drug Res. 37; 1987.

Fig. 3

| Sample | | HPLC Results (AUC) | | | Comments |
|---|---|---|---|---|---|
| ID | Sample Details | Bromide | Acid A | Glycopyrronium | |
| XL-007-106-1 | Main Me-THF layer | 8.77% | 2.26% | 88.96% | |
| XL-007-106-2 | Me-THF after first water wash | 3.61% | 2.38% | 93.99% | |
| XL-007-106-3 | Me-THF after second water wash | 1.34% | 2.39% | 96.26% | |
| XL-007-106-4 | Me-THF after third water wash | 0.71% | 2.34% | 96.93% | |
| XL-007-106-4 | Me-THF after third water wash | 1.73% | 5.18% | 93.08% | Repeated analysis of water layer after standing in the separating funnel for 48 h for improved separation |
| XL-007-106 | After concentration | 2.74% | 5.60% | 91.64% | Concentrated at 25 °C under vacuum |
| XL-007-106-1A | Main water layer | 84.12% | 1.06% | 14.81% | |
| XL-007-106-2A | First water wash | 75.79% | 2.40% | 21.79% | |
| XL-007-106-3A | Second water wash | 66.30% | 5.29% | 28.39% | |
| XL-007-106-4A | Third water wash | 11.57% | 5.08% | 83.33% | |
| XL-007-106-4A | Third water wash | 14.58% | 9.64% | 75.77% | Repeated analysis of water layer after standing in the separating funnel for 48 h for improved separation |

Fig. 4

| Sample | | HPLC Results (AUC) | | | Comments |
|---|---|---|---|---|---|
| ID | Sample Details | Bromide | Acid A | Glycopyrronium | |
| XL-007-109-1 | Me-THF after first water wash | 5.99% | 0.92% | 93.08% | |
| XL-007-109-2 | Me-THF after second water wash | 3.50% | 1.43% | 95.05% | |
| XL-007-109-3 | Me-THF after third water wash | 2.41% | 2.75% | 94.83% | |
| XL-007-109 | After concentration | 8.55% | 3.13% | 88.31% | Concentrated at 25 °C under vacuum |
| XL-007-109-1A | Main water layer | 85.91% | none | 14.08% | |
| XL-007-109-2A | First water wash | 79.67% | none | 20.32% | |
| XL-007-109-3A | Second water wash | 74.11% | none | 25.88% | |
| XL-007-109-4A | Third water wash | 24.73% | 5.03 | 70.23% | |

Fig. 5

| | Reaction 1 | Reaction 2 | Reaction 3 | Reaction 4 |
|---|---|---|---|---|
| Reagents: | | | | |
| SM-1 (scale) | 1.0 g | 1.0 g | 2.5 g | 2.4 g |
| Me$_2$CO$_3$ | 5.0 g (16.8 eq.) | 1.18 g (4.0 eq.) | 2.3 g (3.0 eq.) | 2.8 g (4.0 eq.) |
| Solvent | No extra solvent | t-Amyl alcohol | DMAc | t-Amyl alcohol |
| Oil bath temperature | 130 °C [1] | 140 °C [2] | 130 °C [3] | 130 °C [4] |
| Reaction Time | 6 hours | 2 hours | 7 hours | 14 hours |
| IPC Results | N/A | N/A | Seven hours: 3.6 area% of SM-1; 12.4 area% of Acid A; 84 area% of methyl ester | Seven hours: 51.8 area% of SM-1; 30.4 area% of Acid A; 17.8 area% of methyl ester Fourteen hours 24.5 area% of SM-1; 30.3 area% of Acid A; 45.2 area% of methyl ester |
| Product | 1.1 g after concentration | 1.2 g after concentration | 2.2 g after aqueous wash | N/A |
| HPLC Results | No "Glycopyrronium" peak was observed and some un-reacted SM-1 was present | ~85 area% of SM-1; ~2.3 area% of "Glycopyrronium"; ~11 area% of Acid A | ~95 area% of methyl ester | N/A |
| 1H NMR Results [5] | No methyl peaks matching the quaternary ammonium salt | The methyl peaks corresponding to the quaternary ammonium salt were very small | Product was confirmed as methyl ester of Acid A | N/A |
| Conclusions | Methylation in excess dimethyl carbonate failed to provide the desired methylated product. | Methylation in t-amyl alcohol at ~140°C over two hours failed to afford complete methylation, but hydrolysis of SM-1 to Acid A occurred. | Methylation in DMAc at 130C failed to provide the desired quaternary product, but SM-1 was converted to acid A and its methyl ester. | Methylation in t-amyl alcohol at ~100°C with extended reaction time failed to afford the desired quaternary product. By-product Acid a and its methyl ester was formed during the reaction |

[1] The internal pressure increased to a max pressure with 15 psig.
[2] The internal pressure increased to a max pressure with 15 psig.
[3] The internal pressure increased to a max pressure with 60 psig.
[4] The internal pressure increased to a max pressure with 25 psig.
[5] Acid A was confirmed with the sample independently prepared by hydrolysis of SM-1.

AREA PERCENT REPORT

SORTED BY: SIGNAL
MULTIPLIER: 1.0000
DILUTION: 1.0000
USE MULTIPLIER & DILUTION FACTOR WITH ISTDs

SIGNAL 1: DAD1 A, SIG=210,8 REF=360,100

| PEAK # | RET TIME (MIN) | TYPE | WIDTH (MIN) | AREA (mAU*s) | HEIGHT (mAU) | AREA % |
|---|---|---|---|---|---|---|
| 1 | 15.161 | MM | 0.1272 | 2089.22754 | 273.65390 | 96.0360 |
| 2 | 15.619 | MF | 0.0567 | 3.57500e-1 | 1.05047e-1 | 0.0164 |
| 3 | 15.705 | MF | 0.0746 | 7.69562e-1 | 1.71847e-1 | 0.0354 |
| 4 | 15.827 | FM | 0.1645 | 4.08049 | 4.13368e-1 | 0.1876 |
| 5 | 17.779 | MM | 0.0781 | 5.85760e-1 | 1.24941e-1 | 0.0269 |
| 6 | 18.982 | MM | 0.1080 | 8.85946e-1 | 1.36721e-1 | 0.0407 |
| 7 | 20.325 | MM | 0.0839 | 3.42095e-1 | 6.79694e-2 | 0.0157 |
| 8 | 20.495 | MM | 0.0937 | 10.65661 | 1.89477 | 0.4899 |
| 9 | 21.099 | MM | 0.0771 | 2.62635e-1 | 5.67742e-2 | 0.0121 |
| 10 | 21.887 | MM | 0.1132 | 1.08475 | 1.59675e-1 | 0.0499 |
| 11 | 27.447 | MM | 0.0815 | 2.17781 | 4.45613e-1 | 0.1001 |
| 12 | 28.632 | MM | 0.2774 | 22.36731 | 1.34365 | 1.0282 |
| 13 | 29.313 | MM | 0.0963 | 38.52335 | 6.66453 | 1.7708 |
| 14 | 31.643 | MM | 0.1509 | 1.46514 | 1.61774e-1 | 0.0673 |
| 15 | 32.174 | MF | 0.1355 | 7.88104e-1 | 9.69468e-2 | 0.0362 |
| 16 | 32.306 | FM | 0.1488 | 9.89743e-1 | 1.10865e-1 | 0.0455 |
| 17 | 33.912 | MM | 0.1541 | 8.97962e-1 | 9.71092e-1 | 0.0413 |
| TOTALS: | | | | 2175.46240 | 285.70550 | |

AREA PERCENT REPORT

SORTED BY: SIGNAL
MULTIPLIER: 1.0000
DILUTION: 1.0000
USE MULTIPLIER & DILUTION FACTOR WITH ISTDs

SIGNAL 1: DAD1 A, SIG=210,8 REF=360,100

| PEAK # | RET TIME (MIN) | TYPE | WIDTH (MIN) | AREA (mAU*s) | HEIGHT (mAU) | AREA % |
|---|---|---|---|---|---|---|
| 1 | 15.146 | MM | 0.1268 | 2072.02051 | 272.32730 | 87.6482 |
| 2 | 15.673 | MF | 0.1331 | 7.89762e-1 | 9.88960e-2 | 0.0334 |
| 3 | 15.848 | FM | 0.1611 | 2.03526 | 2.10608e-1 | 0.0861 |
| 4 | 16.223 | MF | 0.1684 | 7.31523e-1 | 7.23953e-2 | 0.0309 |
| 5 | 16.330 | FM | 0.1058 | 3.49233e-1 | 5.50007e-2 | 0.0148 |
| 6 | 16.647 | MF | 0.0652 | 2.50569e-1 | 6.40397e-2 | 0.0106 |
| 7 | 16.703 | FM | 0.0944 | 3.25546e-1 | 5.75042e-2 | 0.0138 |
| 8 | 17.773 | MM | 0.0759 | 6.06932e-1 | 1.33313e-1 | 0.0257 |
| 9 | 18.989 | MM | 0.0904 | 5.99195e-1 | 1.10496e-1 | 0.0253 |
| 10 | 20.319 | MF | 0.0776 | 3.81165e-1 | 8.18591e-2 | 0.0161 |
| 11 | 20.488 | FM | 0.0828 | 224.44286 | 45.17399 | 9.4941 |
| 12 | 21.098 | MM | 0.0825 | 2.98388e-1 | 6.02741e-2 | 0.0126 |
| 13 | 21.885 | MM | 0.0960 | 8.75967e-1 | 1.52156e-1 | 0.0371 |
| 14 | 27.429 | MM | 0.0755 | 2.54322 | 5.61148e-1 | 0.1076 |
| 15 | 29.295 | MM | 0.0976 | 50.23679 | 8.57705 | 2.1251 |
| 16 | 31.633 | MM | 0.1830 | 3.00260 | 2.73486e-1 | 0.1270 |
| 17 | 32.167 | MF | 0.1980 | 2.88648 | 2.42939e-1 | 0.1221 |
| 18 | 32.293 | FM | 0.1333 | 1.64481 | 2.05600e-1 | 0.0696 |
| TOTALS: | | | | 2364.02080 | 328.45806 | |

AREA PERCENT REPORT

SORTED BY: SIGNAL
CALIB. DATA MODIFIED: 12/05/2014 8:40:34 AM
MULTIPLIER: 1.0000
DILUTION: 1.0000
USE MULTIPLIER & DILUTION FACTOR WITH ISTDs

SIGNAL 1: DAD1 A, SIG=210,8 REF=360,100

| PEAK # | RET TIME (MIN) | TYPE | WIDTH (MIN) | AREA (mAU*s) | AREA % | NAME |
|---|---|---|---|---|---|---|
| 1 | 13.050 | BB | 0.1404 | 1469.35474 | 90.8652 | GP |
| 2 | 13.788 | BV | 0.1333 | 1.38567 | 0.0857 | ? |
| 3 | 15.008 | BV | 0.1086 | 3.38840e-1 | 0.0210 | ? |
| 4 | 15.339 | BV | 0.0173 | 3.19566e-1 | 0.0198 | ? |
| 5 | 15.830 | BV | 0.0797 | 5.53090e-1 | 0.0342 | ? |
| 6 | 17.165 | BV | 0.0936 | 6.71909e-1 | 0.0416 | ? |
| 7 | 17.682 | BB | 0.0807 | 92.99374 | 5.7508 | ACID A |
| 8 | 20.177 | BV | 0.0606 | 6.81594e-1 | 0.0421 | ? |
| 9 | 24.393 | BB | 0.0950 | 27.98519 | 1.7306 | ? |
| 10 | 24.815 | BB | 0.0880 | 2.03513 | 0.1259 | ? |
| 11 | 26.398 | BB | 0.0798 | 20.75115 | 1.2833 | ? |

TOTALS: 1617.07061

AREA PERCENT REPORT

SORTED BY: SIGNAL
CALIB. DATA MODIFIED: 12/05/2014 8:40:34 AM
MULTIPLIER: 1.0000
DILUTION: 1.0000
USE MULTIPLIER & DILUTION FACTOR WITH ISTDs

SIGNAL 1: DAD1 A, SIG=210,8 REF=360,100

| PEAK # | RET TIME (MIN) | TYPE | WIDTH (MIN) | AREA (mAU*s) | AREA % | NAME |
|---|---|---|---|---|---|---|
| 1 | 13.050 | BB | 0.1426 | 1480.29688 | 90.8661 | GP |
| 2 | 13.766 | BV | 0.1456 | 1.53003 | 0.0939 | ? |
| 3 | 15.003 | BV | 0.0859 | 4.99939e-1 | 0.0307 | ? |
| 4 | 15.313 | BB | 0.0469 | 1.65397e-1 | 0.0102 | ? |
| 5 | 15.828 | BV | 0.0777 | 5.95428e-1 | 0.0365 | ? |
| 6 | 17.161 | BV | 0.1183 | 9.80880e-1 | 0.0602 | ? |
| 7 | 17.684 | BB | 0.0788 | 94.28443 | 5.7875 | ACID A |
| 8 | 20.179 | BV | 0.0707 | 4.78445e-1 | 0.0294 | ? |
| 9 | 24.395 | BB | 0.0905 | 26.70000 | 1.6389 | ? |
| 10 | 24.818 | BB | 0.0857 | 1.94646 | 0.1195 | ? |
| 11 | 26.399 | BB | 0.0807 | 21.61863 | 1.3270 | ? |

TOTALS: 1629.09649

AREA PERCENT REPORT

SORTED BY: SIGNAL
CALIB. DATA MODIFIED: 12/05/2014 8:40:34 AM
MULTIPLIER: 1.0000
DILUTION: 1.0000
USE MULTIPLIER & DILUTION FACTOR WITH ISTDs

SIGNAL 1: DAD1 A, SIG=210,8 REF=360,100

| PEAK # | RET TIME (MIN) | TYPE | WIDTH (MIN) | AREA (mAU*s) | AREA % | NAME |
|---|---|---|---|---|---|---|
| 1 | 13.058 | BB | 0.1414 | 1372.55225 | 91.2525 | GP |
| 2 | 13.824 | BBA | 0.1648 | 1.08466 | 0.0721 | ? |
| 3 | 15.855 | BV | 0.0893 | 6.35602e-1 | 0.0423 | ? |
| 4 | 17.133 | BV | 0.0946 | 8.06691e-1 | 0.0536 | ? |
| 5 | 17.686 | BV | 0.0808 | 61.94052 | 4.1180 | ACID A |
| 6 | 18.309 | BB | 0.0713 | 4.62513e-1 | 0.0307 | ? |
| 7 | 18.587 | BV | 0.0856 | 6.09179e-1 | 0.0405 | ? |
| 8 | 20.178 | BV | 0.0632 | 3.29590e-1 | 0.0219 | ? |
| 9 | 24.477 | BB | 0.0903 | 3.14137 | 0.2089 | ? |
| 10 | 24.816 | BB | 0.0834 | 3.01253 | 0.2003 | ? |
| 11 | 26.401 | BB | 0.0807 | 30.61319 | 2.0353 | ? |
| 12 | 28.566 | BB | 0.1318 | 4.86617 | 0.3235 | ? |
| 13 | 29.584 | BB | 0.1172 | 24.07088 | 1.6003 | ? |

TOTALS: 1504.12514

AREA PERCENT REPORT

SORTED BY: SIGNAL
CALIB. DATA MODIFIED: 12/05/2014 8:40:34 AM
MULTIPLIER: 1.0000
DILUTION: 1.0000
USE MULTIPLIER & DILUTION FACTOR WITH ISTDs

SIGNAL 1: DAD1 A, SIG=210,8 REF=360,100

| PEAK # | RET TIME (MIN) | TYPE | WIDTH (MIN) | AREA (mAU*s) | AREA % | NAME |
|---|---|---|---|---|---|---|
| 1 | 13.057 | BB | 0.1408 | 1363.68787 | 91.3890 | GP |
| 2 | 13.796 | BBA | 0.1060 | 5.88608e-1 | 0.0394 | ? |
| 3 | 15.822 | BB | 0.0907 | 6.96373e-1 | 0.0467 | ? |
| 4 | 17.172 | BV | 0.1278 | 1.11755 | 0.0749 | ? |
| 5 | 17.690 | BB | 0.0811 | 59.83648 | 4.0100 | ACID A |
| 6 | 18.313 | BV | 0.0636 | 4.38142e-1 | 0.0294 | ? |
| 7 | 18.576 | BV | 0.0938 | 9.20101e-1 | 0.0617 | ? |
| 8 | 20.183 | BV | 0.0545 | 4.27755e-1 | 0.0287 | ? |
| 9 | 24.477 | BB | 0.0937 | 2.97541 | 0.1994 | ? |
| 10 | 24.818 | BB | 0.0854 | 3.15553 | 0.2115 | ? |
| 11 | 26.399 | BB | 0.0804 | 29.99472 | 2.0101 | ? |
| 12 | 28.509 | BB | 0.1291 | 3.75733 | 0.2518 | ? |
| 13 | 29.572 | BB | 0.1162 | 24.58340 | 1.6475 | ? |

TOTALS: 1492.17926

AREA PERCENT REPORT

SORTED BY: SIGNAL
CALIB. DATA MODIFIED: 12/05/2014 8:40:34 AM
MULTIPLIER: 1.0000
DILUTION: 1.0000
USE MULTIPLIER & DILUTION FACTOR WITH ISTDs

SIGNAL 1: DAD1 A, SIG=210,8 REF=360,100

| PEAK # | RET TIME (MIN) | TYPE | WIDTH (MIN) | AREA (mAU*s) | AREA % | NAME |
|---|---|---|---|---|---|---|
| 1 | 13.070 | BB | 0.1352 | 1163.46033 | 39.7889 | GP |
| 2 | 15.865 | BB | 0.0939 | 4.13036e-1 | 0.0141 | ? |
| 3 | 17.136 | BB | 0.0432 | 2.14958e-1 | 7.351e-3 | ? |
| 4 | 17.692 | BB | 0.0808 | 70.54691 | 2.4126 | ACID A |
| 5 | 18.309 | BBA | 0.0662 | 2.93541e-1 | 0.0100 | ? |
| 6 | 18.989 | BV | 0.0796 | 6.31166e-1 | 0.0216 | ? |
| 7 | 20.184 | BV | 0.0616 | 3.60141e-1 | 0.0123 | ? |
| 8 | 20.386 | VV | 0.1058 | 1.23050 | 0.0421 | ? |
| 9 | 21.261 | BV | 0.1090 | 2.03984 | 0.0698 | ? |
| 10 | 22.699 | BV | 0.1379 | 8.42927 | 0.2883 | ? |
| 11 | 23.359 | BV | 0.1343 | 2.18818 | 0.0748 | ? |
| 12 | 24.818 | BB | 0.1154 | 2.24744 | 0.0769 | ? |
| 13 | 26.401 | BV | 0.1177 | 23.02224 | 0.7873 | ? |
| 14 | 26.653 | VB | 0.1116 | 2.62104 | 0.0896 | ? |
| 15 | 27.853 | BV | 0.0890 | 1614.01575 | 55.1974 | ? |
| 16 | 28.158 | VV | 0.1018 | 22.51083 | 0.7698 | ? |
| 17 | 28.344 | VB | 0.1657 | 6.38885 | 0.2185 | ? |
| 18 | 32.591 | BB | 0.1287 | 3.46753 | 0.1186 | ? |
| TOTALS: | | | | 1492.17926 | | |

AREA PERCENT REPORT

SORTED BY: SIGNAL
CALIB. DATA MODIFIED: 12/05/2014 8:40:34 AM
MULTIPLIER: 1.0000
DILUTION: 1.0000
USE MULTIPLIER & DILUTION FACTOR WITH ISTDs

SIGNAL 1: DAD1 A, SIG=210,8 REF=360,100

| PEAK # | RET TIME (MIN) | TYPE | WIDTH (MIN) | AREA (mAU*s) | AREA % | NAME |
|---|---|---|---|---|---|---|
| 1 | 13.051 | BB | 0.1399 | 1402.12244 | 39.5620 | GP |
| 2 | 14.848 | BV | 0.0628 | 3.66435e-1 | 0.0103 | ? |
| 3 | 15.814 | BV | 0.0718 | 4.62627e-1 | 0.0131 | ? |
| 4 | 17.142 | BV | 0.1082 | 1.15670 | 0.0326 | ? |
| 5 | 17.686 | BB | 0.0787 | 85.66539 | 2.4171 | ACID A |
| 6 | 20.175 | BV | 0.0541 | 3.89841e-1 | 0.0110 | ? |
| 7 | 20.382 | VV | 0.1030 | 1.34319 | 0.0379 | ? |
| 8 | 21.247 | BV | 0.1028 | 1.83370 | 0.0517 | ? |
| 9 | 22.692 | BV | 0.1183 | 6.94587 | 0.1960 | ? |
| 10 | 22.846 | VV | 0.0717 | 1.10283 | 0.0311 | ? |
| 11 | 23.355 | BV | 0.0884 | 1.22437 | 0.0345 | ? |
| 12 | 24.476 | BB | 0.0930 | 1.55678 | 0.0439 | ? |
| 13 | 24.813 | BBA | 0.0798 | 1.31747 | 0.0372 | ? |
| 14 | 26.396 | BV | 0.0746 | 15.82830 | 0.4466 | ? |
| 15 | 26.466 | VV | 0.0711 | 12.21716 | 0.3447 | ? |
| 16 | 26.651 | VB | 0.1458 | 4.21305 | 0.1189 | ? |
| 17 | 27.848 | BV | 0.0893 | 1964.56592 | 55.4318 | ? |
| 18 | 28.155 | VV | 0.1058 | 28.56983 | 0.8061 | ? |
| 19 | 28.335 | VB | 0.1547 | 8.38243 | 0.2365 | ? |
| 20 | 32.606 | BB | 0.1398 | 4.84739 | 0.1368 | ? |

TOTALS: 3544.11171

GLYCOPYRRONIUM FATTY ACID SALTS AND METHODS OF MAKING SAME

REFERENCE TO RELATED APPLICATIONS

This application claims one or more inventions which were disclosed in Provisional Application No. 62/175,737, filed Jun. 15, 2015, entitled "GLYCOPYRRONIUM FATTY ACID SALTS AND METHODS OF MAKING SAME". The benefit under 35 USC § 119(e) of the United States provisional application is hereby claimed, and the aforementioned application is hereby incorporated herein by reference.

FIELD OF THE INVENTION

The invention pertains to the field of glycopyrronium salts. More specifically, the invention pertains to novel lipophilic glycopyrronium fatty acid salts.

BACKGROUND OF THE INVENTION

Glycopyrrolate (also known as glycopyrronium bromide) is a bromide salt with a quaternary ammonium counterion with the chemical name of 3-[cyclopentyl (hydroxy)phenylacetoxy]-1,1-dimethyl pyrrolidinium bromide, a molecular formula of $C_{19}H_{28}BrNO_3$ and a molecular weight of 398.34. Its chemical structure is shown in Table 2 below.

Trospium chloride is a quaternary ammonium salt with the chemical name of 3 (2 hydroxy-2,2 diphenylacetoxy) spiro[bicyclo[3.2.1]octane-8,1'pyrrolidin]-1'-ium chloride. The molecular formula of trospium chloride is $C_{25}H_{30}ClNO_3$ and its molecular weight is 427.97. The chemical structure of trospium chloride is:

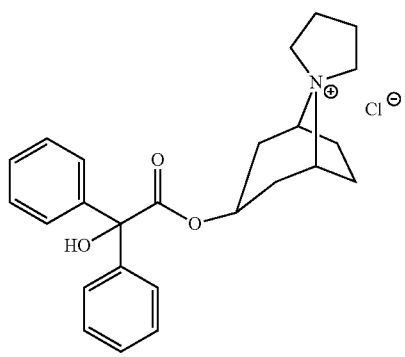 [SMILES: O=C(OC1CC2CCC(C1)[N+]21CCCC1)C(O)(c1ccccc1)c1ccccc1 ; [Cl-]]

The quaternary ammonium antimuscarinic drugs (QAAM) are particularly useful because of their ability to antagonize endogenous acetylcholine during periods of excessive acetylcholine production, or prolonged acetylcholine effect from physiologic and pharmacologic reasons. These compounds share the property that they do not appreciably penetrate the central nervous system (CNS), and glycopyrrolate and trospium chloride have been particularly useful in treating patients in need of a peripheral anticholinergic effect on antimuscarinic receptors.

The same biochemical property that is advantageous in preventing CNS distribution, also limits intestinal absorption, requiring the currently available formulations of these medications to be taken in the absence of food, and resulting in incomplete and variable bioavailability in patients.

SUMMARY OF THE INVENTION

Bi-phasic reaction conditions enable the desired counterion exchange reactions between glycopyrronium bromide and alkali and alkaline earth metal salts of fatty acids. Favorable partitioning of the glycopyrronium moiety into the organic phase (along with the fatty acids) and partitioning of the bromide into the aqueous phase preferably uses water and methyl tetrahydrofuran. While the glycopyrronium fatty acid salts are unstable with respect to hydrolysis under the reaction conditions and are isolated as oily products, an excess of the fatty acid in the reaction mixture stabilizes the glycopyrronium fatty acid salt and reduces the formation of the hydrolysis byproduct impurity, Acid A.

Methods of manufacturing glycopyrronium fatty acid salts preferably include use of a molar excess of the fatty acid. In some embodiments, at least a 0.2 molar equivalent of excess free fatty acid is added to the reaction mixture to form a glycopyrronium fatty acid salt. In some preferred embodiments, between 0.2 and 1.2 molar equivalent of excess free fatty acid is added to the reaction mixture. In another preferred embodiment, at least 0.6 molar equivalent of excess free fatty acid is added to the reaction mixture. In yet another preferred embodiment, between 0.6 and 1.2 molar equivalent of excess free fatty acid is added to the mixture to form a glycopyrronium fatty acid salt. In another embodiment, approximately 1.2 molar equivalent of excess free fatty acid is added to the reaction mixture. In another embodiment, at least 1.1 molar equivalent of excess free fatty acid is added to the reaction mixture.

Since excess free fatty acids stabilize the formulations described herein, this may result in enhanced bioavailability of the glycopyrronium moiety.

BRIEF DESCRIPTION OF THE DRAWINGS

FIG. 3 shows the HPLC Results of an exchange reaction of glycopyrronium bromide with potassium stearate.

FIG. 4 shows the HPLC Results of an exchange reaction of glycopyrronium bromide with potassium palmitate.

FIG. 5 shows the methylation of glycopyrrolate base with dimethyl carbonate.

DETAILED DESCRIPTION OF THE INVENTION

Figure 1:
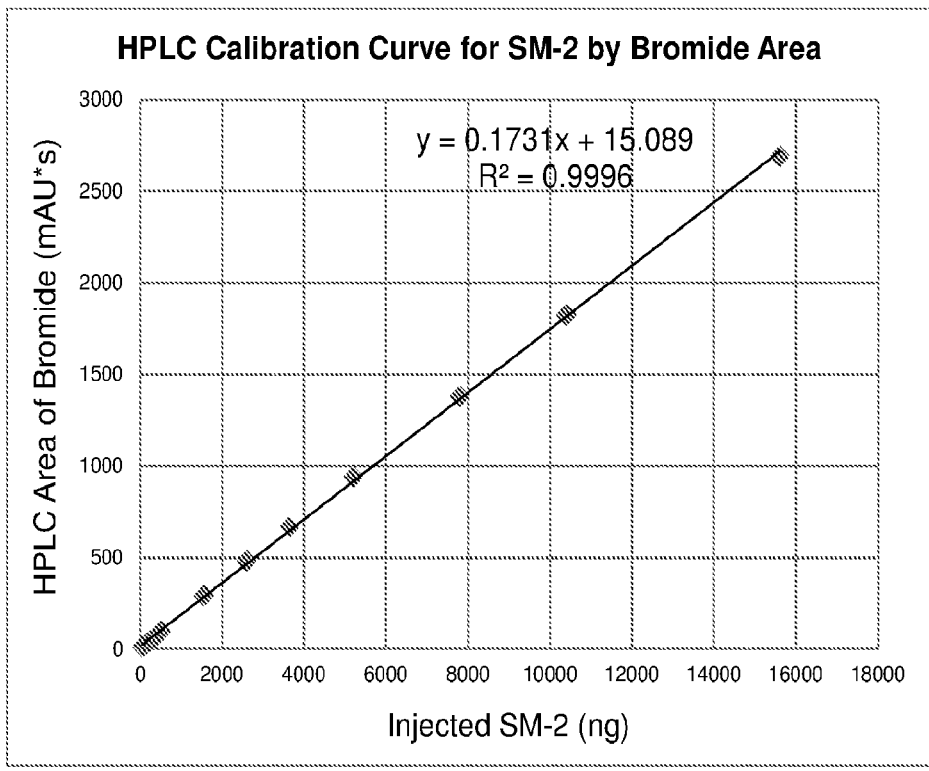
FIG. 1 shows the HPLC Calibration Curve for glycopyrronium bromide by Bromide Peak.

Currently available quaternary ammonium anti-cholinergic muscarinic receptor antagonists compositions occur as a salt, with the quaternary ammonium cation and a non-organic anion.

U.S. Pat. No. 8,097,633, entitled "Uses for Quaternary Ammonium Anticholinergic Muscarinic Receptor Antagonists in Patients Being Treated for Cognitive Impairment or Acute Delirium", issued Jan. 17, 2012, and U.S. Patent Publication 2012/0088785, entitled "New Uses for Quaternary Ammonium Anticholinergic Muscarinic Receptor Antagonists in Patients Being Treated for Cognitive Impairment or Acute Delirium", published Apr. 12, 2012, both herein incorporated by reference, disclose methods for treating the adverse effects of acetylcholinesterase inhibitors using quaternary ammonium anti-cholinergic muscarinic receptor antagonists such as glycopyrrolate or trospium.

U.S. Pat. No. 8,969,402, entitled "Combined Acetylcholinesterase Inhibitor and Quaternary Ammonium Antimuscarinic Therapy to Alter Progression of Cognitive Diseases", issued Mar. 3, 2015, and US Patent Publication No. 2013/0172398, entitled "Combined Acetylcholinesterase Inhibitor and Quaternary Ammonium Antimuscarinic Therapy to Alter Progression of Cognitive Diseases", published Jul. 4, 2013, both herein incorporated by reference, disclose administering quaternary ammonium anti-cholinergic muscarinic receptor antagonists in combination with acetyl-cholinesterase inhibitors to treat either cognitive impairment or acute delirium. This therapy results in a modification of a cognitive disorder or disease, namely a slow-down in the disease progression. New formulations for quaternary ammonium anti-cholinergic muscarinic receptor antagonists are also disclosed.

In preferred embodiments of the present invention, a quaternary ammonium anti-cholinergic muscarinic receptor antagonist includes a salt comprising an organic lipophilic anion as an anionic component of the salt. In some preferred embodiments, the lipophilic anion of the quaternary ammonium anti-cholinergic muscarinic receptor antagonist preferably includes a fatty acid including at least eight carbon molecules. In some preferred embodiments, the quaternary ammonium anti-cholinergic muscarinic receptor antagonist is glycopyrrolate or trospium.

The quaternary ammonium antimuscarinic drugs (QAAM) are particularly useful because of their ability to antagonize endogenous acetylcholine during periods of excessive acetylcholine production, or prolonged acetylcholine effect from physiologic and pharmacologic reasons. These compounds share the property that they do not appreciably penetrate the central nervous system (CNS), and glycopyrronium bromide and trospium chloride have been particularly useful in treating patients in need of a peripheral anticholinergic effect on antimuscarinic receptors.

The same biochemical property that is advantageous in preventing CNS distribution, also limits intestinal absorption, requiring the currently available formulations of these medications to be taken in the absence of food, and resulting in incomplete and variable bioavailability in patients.

Enhancing the oral bioavailability of glycopyrrolate, trospium, and other QAAMs allows for administration of the medication without regard to food, and possibly without regard to other medications. It would also decrease the inter-subject variability in effect of the medication and reduce the effect of changes in gastrointestinal motility on drug absorption, because the degree of variability between patients is directly proportional to the time it takes to absorb a medication. There may also be an improvement in patient adherence to taking the medication by being able to take it in proximity to food.

A QAAM is produced with a lipophilic anion as the anionic component of a salt. Structure activity analysis (SAR) suggests that an optimum lipophilic anion would be a fatty acid of at least 8 carbon molecules, so that the hydrophobic tail of the molecules would provide enhanced lipid solubility to counteract the positive charge of the ionized cationic QAAM molecule. In some preferred embodiments, the appropriate salts come from a family of medium and long chain fatty acids including, but not limited to: arachidic acid, stearic acid, palmitic acid, oleic acid, erucic acid, linoleic acid, arachidonic acid, lauric acid, capric acid, linolenic acid, or myristic acid.

The salt of the QAAM (cation) and the fatty acid (anion) can be produced through organic chemistry reactions referred to as "ion swapping", "counterion exchange" or "salt metathesis". In such a reaction, the QAAM compound as the current elemental salt (glycopyrrolate hydrobromide, trospium chloride) is placed in a biphasic solution with the elemental salt of an omega-3 fatty acid such as α-linolenic acid. The solution is subjected to variations in temperature, pH and agitation to produce a salt that is selectively extracted into the organic phase. The extracts are concentrated under reduced pressure to remove the solvent and the salt is isolated, qualitatively and quantitatively identified and then stoichiometrically administered to animals. Quantitative serum and/or urine assays are used to make comparisons with the elemental salt of the QAAM, both in the presence and absence of food. Intravenous administration of the QAAM (example: glycopyrrolate) with quantitative serum and/or urine assay can be used as a reference standard for 100% bioavailability, and both the native compound and the synthesized salt are compared against this to establish their relative bioavailability in the presence and absence of food and other commonly co-administered medications.

In addition to the bioavailability studies mentioned above, quality studies would need to be done during the process to make sure there is no hydrolysis of the QAAM molecule in the process.

The synthesized fatty acids/QAAM salt are useful as an individual product for the treatment of various diseases involving excessive acetylcholine activity in humans and animals, whether these are produced by a pathologic process or the use of a medication (including but not limited to: overactive bladder, sialorrhea, diarrhea, bradycardia, hyperhidrosis, overactive gastric secretion, dumping syndrome, bronchospasm, vasomotor rhinitis). Enhanced bioavailability QAAM should be able to improve symptoms without causing significant central nervous system anti-cholinergic toxicity. Enhanced bioavailability allows for administration without regard to food, and may also allow for transdermal absorption to be enhanced to the level that transdermal formulations of this product would be practical. This could also be used in combination with acetylcholinesterase inhibiting drugs, or any other drug that increases acetylcholine tone.

Bi-phasic reaction conditions enable the desired exchange reactions between glycopyrronium bromide and fatty acid salts of alkali metals and alkaline earth metals to produce glycopyrronium fatty acid salts. Favorable partitioning of the glycopyrronium moiety into the organic phase (along with the fatty acids) and partitioning of the bromide into the aqueous phase uses water and methyl tetrahydrofuran. While the glycopyrronium fatty acid salts are moderately unstable with respect to hydrolysis under the reaction conditions and are isolated as oily products, an excess of the fatty acid in the reaction mixture stabilizes the glycopyrronium fatty acid salt and reduces the formation of the hydrolysis byproducts, Acid A and the quaternary ammonium degradant (QAA).

The mixture of glycopyrronium fatty acid salt and excess free fatty acid may be isolated from each other to produce a consistent, well defined product. The glycopyrronium fatty acid salts described herein potentially offer the desired increase in glycopyrronium bioavailability. Since excess free fatty acids stabilize the formulations described herein, this may result in enhanced bioavailability of the glycopyrronium moiety.

Practical and scalable synthetic processes for preparation of lipophilic glycopyrronium fatty acid salts were developed. Initially, the preparation of the lipophilic glycopyrronium fatty acid salts from glycopyrronium bromide and fatty acid potassium salts was performed in organic solvents (anhydrous conditions) or biphasic (water/organic) conditions since this provided an opportunity for quick success in identifying a suitable preparative procedure. Solubility of the starting materials and products impacted these options, ultimately limiting the approach to bi-phasic (solvent/water) systems. The preparation of the lipophilic glycopyrronium fatty acid salts primarily utilized lauric acid, palmitic acid, linoleic acid and stearic acid (potassium stearate). The processes utilized different salts, including Na, K and Ca salts of fatty acids. In other embodiments, Mg or Ba salts of fatty acids are used.

The evaluation included multiple steps. The first step was screening and evaluation of lipophilic salt preparation options utilizing lauric acid. Subsequent process development and analytical method development were conducted using preparations using stearic acid. Then, at least 5 g of a lipophilic glycopyrronium fatty acid salt utilizing stearic acid was created. Three additional and different samples of at least 3 g lipophilic glycopyrronium salts were synthesized with additional fatty acids (palmitic acid, lauric acid, linoleic acid and stearic acid—see Table 23B below). The resulting four samples were then characterized.

Analytical methods were also developed for the glycopyrronium fatty acid salts. These methods appropriately and accurately assess the quality of future glycopyrronium fatty acid salts development samples. A more refined process for the general synthesis of glycopyrronium fatty acid salts has also been developed.

Some of the analytical method applications include, but are not limited to, an assessment of the salt exchange effectiveness, to ensure that the reactions are pushed to >95% conversion by determining an optimal number and amount of aqueous washes to remove inorganic bromide salts (byproducts), the determination of the optimal amount of excess free fatty acid (evaluating a suitable range of molar equivalents) needed to stabilize the active pharmaceutical ingredient (API) and the improvement of the isolation and purification of the reaction product (for example through precipitation with suitable solvent/antisolvent combinations) by evaluating the purity of the reaction products. In some preferred embodiments, the optimal number of aqueous washes is 3-4 washes. In other embodiments, the preferred number of washes is at least three washes.

Analytical method development also preferably includes methods for quantitation of chromophoric starting materials, products and degradants, method for quantitation of weakly- or non-chromophoric starting materials and degradants (fatty acids and derived salts, dimethylhydroxypyrrolidinium degradants), methods for quantitation of the bromide ion in the starting material and the product, and methods for quantitation of the potassium (or sodium) ion in the product. Individually, none of these methods alone would be sufficient to assess the effectiveness of the salt exchange process and the purity of the derived products, but taken together, the combination of these orthogonal analytical methods achieves both of these objectives.

Some abbreviations used throughout this application are shown in Table 1 and chemical structures are shown in Table 2.

TABLE 1

| | |
|---|---|
| API | Active Pharmaceutical Ingredient |
| ACN | Acetonitrile |
| Br | Bromine |
| DCM | Dichloromethane |
| DMSO | Dimethylsulfoxide |
| FA | Fatty acid |
| GC | Gas Chromatography |
| GP | Glycopyrronium |
| GPBr | Glycopyrronium Bromide |
| GPFA | Glycopyrronium Fatty Acid |
| HPLC | High Performance Liquid Chromatography |

TABLE 1-continued

| | |
|---|---|
| IPAc | Isopropyl acetate |
| K | Potassium |
| 2-Me-HF | 2-Methyl Tetrahydrofuran (Methyl-THF) |
| MIBK | Methyl Isobutyl Ketone |
| MTBE | Methyl-t-Butyl Ether |
| Na | Sodium |
| QAA | Quaternary Amino Alcohol (descriptive reference for degradant CAS 51052-74-5, 3-hydroxy-1,1-dimethyl pyrrolidinium bromide) |

TABLE 2

| Entry | Chemical Structure | Origin | Notes |
|---|---|---|---|
| 1 | Glycopyrronium Bromide mw 398.34 | Starting Material | |
| 2 | (M = K, Na) | Starting Material | Alkali metal salts of Fatty Acids |
| 3 | 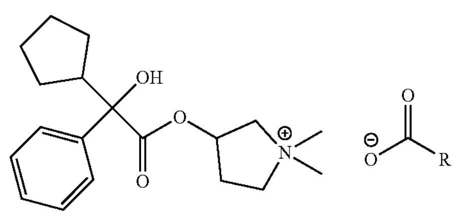 | Reaction Product | Glycopyrronium Fatty Acid Salt(s) |
| 4 | 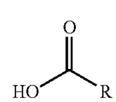 | Additive | Fatty Acids (excess) |
| 5 | (e.g. KBr, NaBr) | Reaction By-Product | Bromide Salts |
| 6 | "Acid A" CAS 427-49-6 α-cyclopentyl-α-hydroxy-benzene acetic acid | Degradant | Derived from Starting Material (entry 1) or Product (entry 3) |

TABLE 2-continued

| Entry | Chemical Structure | Origin | Notes |
|---|---|---|---|
| 7 | Fatty acid salt of CAS 109357-53-1<br>3-hydroxy-1,1-dimethyl pyrrolidinium Fatty acid salt | Degradant | Derived from Product (entry 3) |
| 8 | "QAA", (Quaternary Amino Alcohol), CAS 51052-74-5, 3-hydroxy-1,1-dimethyl pyrrolidinium bromide | Degradant | Derived from Starting Material (entry 1) |
| 9 | Methyl THF | Reaction Solvent | |

A general chemical structure for the targeted lipophilic glycopyrronium fatty acid salts 1 is shown below in Table 3A.

TABLE 3A

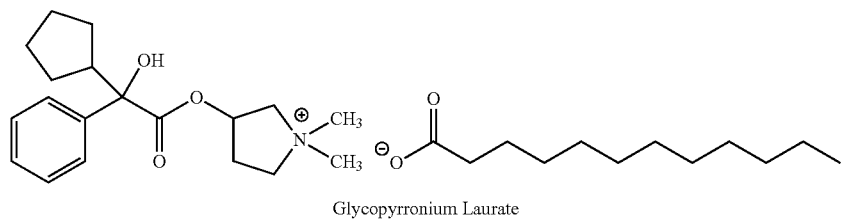 [SMILES: C[N+]1(C)CCC(OC(=O)C(O)(c2ccccc2)C2CCCC2)C1 ; CCCCCCCCCCCC(=O)[O-]]

Chemical structures for some preferred examples of glycopyrronium fatty acid salts are listed here.

R=$C_{11}H_{23}$ (lauric acid)

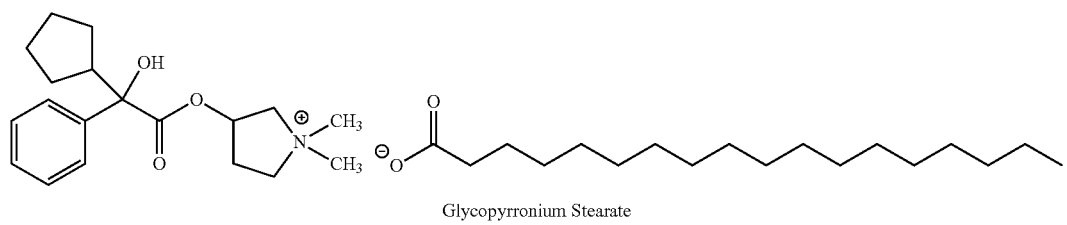 [SMILES: C[N+]1(C)CCC(OC(=O)C(O)(c2ccccc2)C2CCCC2)C1 ; CCCCCCCCCCCCCCCCCC(=O)[O-]]

Glycopyrronium Laurate

R=$C_{17}H_{35}$ (stearic acid)

Glycopyrronium Stearate

R=C$_{17}$H$_{33}$ (oleic acid)
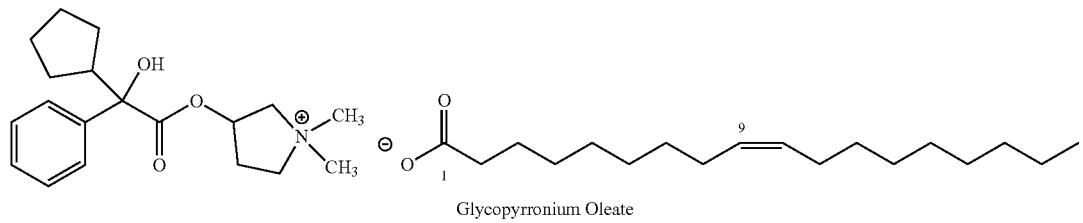 [SMILES: C[N+]1(C)CCC(OC(=O)C(O)(c2ccccc2)C2CCCC2)C1 ; CCCCCCCC/C=C\CCCCCCCC(=O)[O-]]
Glycopyrronium Oleate
R=C$_{15}$H$_{31}$ (palmitic acid)
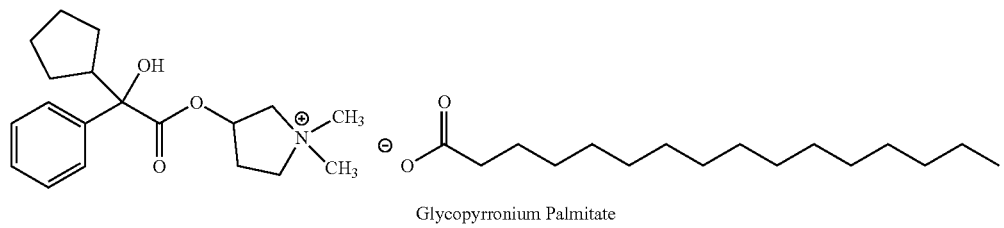 [SMILES: C[N+]1(C)CCC(OC(=O)C(O)(c2ccccc2)C2CCCC2)C1 ; CCCCCCCCCCCCCCCC(=O)[O-]]
Glycopyrronium Palmitate
R=C$_9$H$_{19}$ (capric acid)
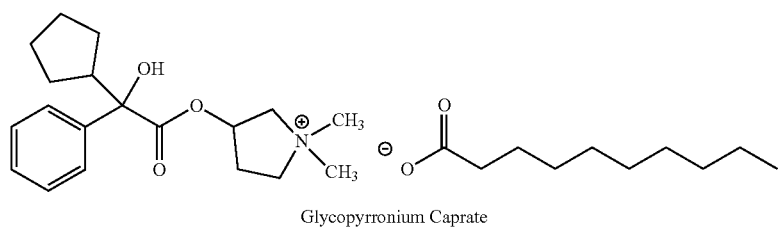 [SMILES: C[N+]1(C)CCC(OC(=O)C(O)(c2ccccc2)C2CCCC2)C1 ; CCCCCCCCCC(=O)[O-]]
Glycopyrronium Caprate
R=C$_{19}$H$_{31}$ (arachidonic acid)
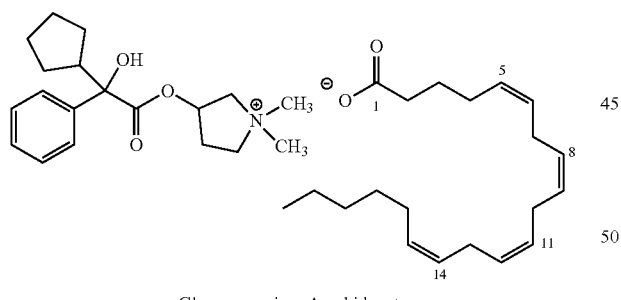
Glycopyrronium Arachidonate
R=C$_{19}$H$_{39}$ (arachidic acid)
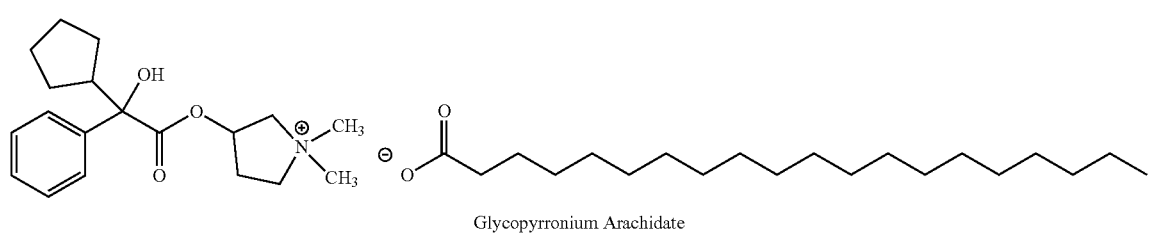 [SMILES: C[N+]1(C)CCC(OC(=O)C(O)(c2ccccc2)C2CCCC2)C1 ; CCCCCCCCCCCCCCCCCCCC(=O)[O-]]
Glycopyrronium Arachidate R=C$_{21}$H$_{41}$ (erucic acid)
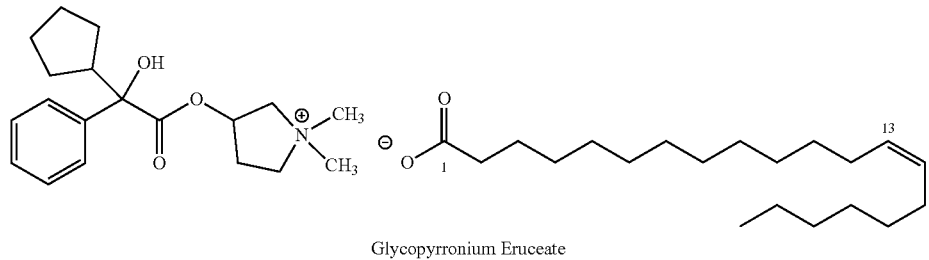 [SMILES: C[N+]1(C)CCC(OC(=O)C(O)(c2ccccc2)C2CCCC2)C1 ; CCCCCC/C=C\CCCCCCCCCCCC(=O)[O-]]
Glycopyrronium Eruceate
R=C$_{17}$H$_{31}$ (linoleic acid)
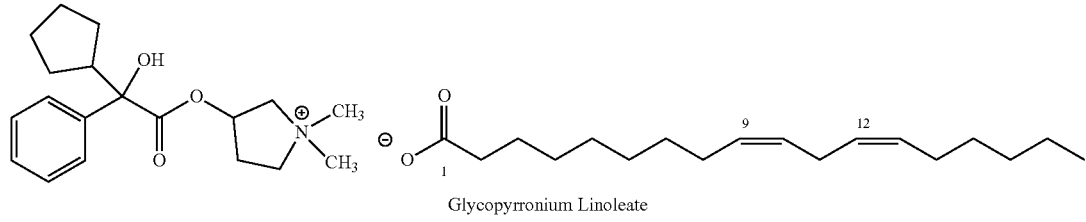 [SMILES: C[N+]1(C)CCC(OC(=O)C(O)(c2ccccc2)C2CCCC2)C1 ; CCCCC/C=C\C/C=C\CCCCCCCC(=O)[O-]]
Glycopyrronium Linoleate
R=C$_{13}$H$_{27}$ (myristic acid)
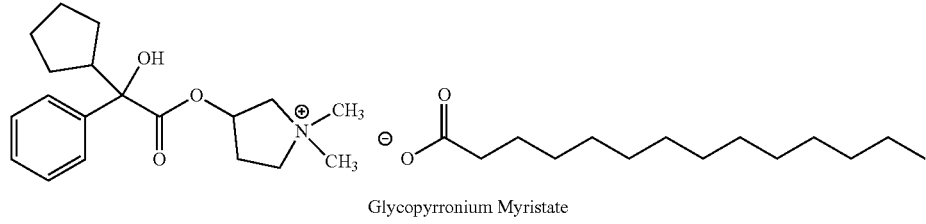 [SMILES: C[N+]1(C)CCC(OC(=O)C(O)(c2ccccc2)C2CCCC2)C1 ; CCCCCCCCCCCCCC(=O)[O-]]
Glycopyrronium Myristate
R=C$_{17}$H$_{29}$ (α-linolenic acid)
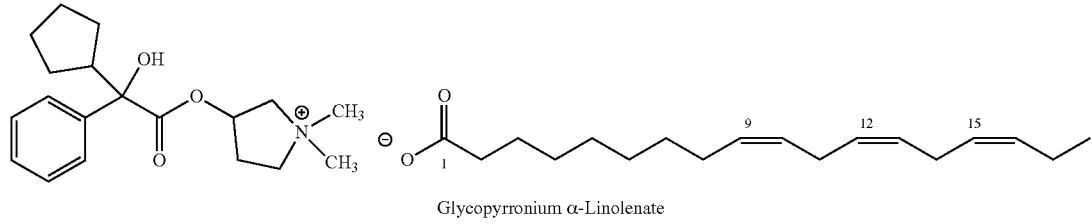 [SMILES: C[N+]1(C)CCC(OC(=O)C(O)(c2ccccc2)C2CCCC2)C1 ; CC/C=C\C/C=C\C/C=C\CCCCCCCC(=O)[O-]]
Glycopyrronium α-Linolenate
R=C$_{17}$H$_{29}$ (γ-linolenic acid)
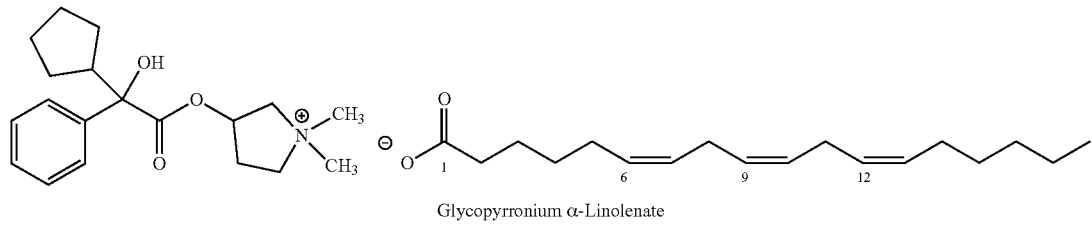 [SMILES: C[N+]1(C)CCC(OC(=O)C(O)(c2ccccc2)C2CCCC2)C1 ; CCCCC/C=C\C/C=C\C/C=C\CCCCC(=O)[O-]]
Glycopyrronium α-Linolenate There were two preferred starting materials (glycopyrronium bromide 2 and glycopyrrolate base 3), as shown in Table 3B below.

TABLE 3B

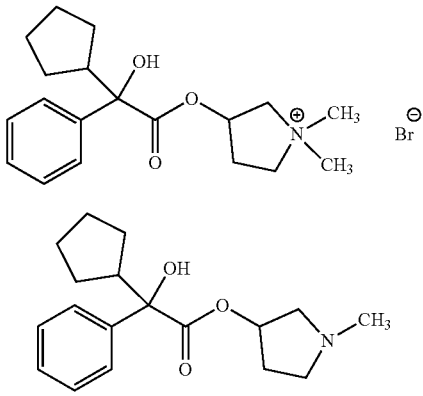

Synthesis of Glycopyrronium salts

A practical, scalable synthesis of glycopyrronium salts of fatty acids was developed. The general chemical structure of the glycopyrronium salt of fatty acids is shown as compound 1 in Table 3A. Three different approaches were considered, starting from either glycopyrronium bromide (compound 2 in Table 3B, also known as "glycopyrrolate") or from a synthetic precursor, designated herein as the glycopyrrolate base (compound 3 in Table 3B). The three approaches were a) salt metathesis using ion exchange resins, starting from glycopyrronium bromide (compound 2 in Table 3B), b) direct salt metathesis, starting from glycopyrronium bromide (compound 2 in Table 3B), and c) synthesis via glycopyrronium methyl carbonates, using glycopyrrolate base (compound 3 in Table 3B) as the starting material.

Adding at least 0.2 molar equivalents of excess free fatty acids into a preparation with fatty acid salts and glycopyrronium bromide in a water/Me-THF system stabilized the reaction mixture and allowed for the formation of glycopyrronium fatty acid salts.

"Free fatty acid" as defined herein is fatty acid in its free form, which is different from the fatty acid in its ionized form (salt form).

In preferred embodiments, at least a 0.2 molar equivalent of excess free fatty acid is added to the reaction mixture to form a glycopyrronium fatty acid salt. In some preferred embodiments, between 0.2 and 1.2 molar equivalent of excess free fatty acid is added to the reaction mixture. In another preferred embodiment, at least 0.6 molar equivalent of excess free fatty acid is added to the reaction mixture. In yet another preferred embodiment, between 0.6 and 1.2 molar equivalent of excess free fatty acid is added to the mixture to form a glycopyrronium fatty acid salt. In another embodiment, approximately 1.2 molar equivalent of excess free fatty acid is added to the reaction mixture. In another embodiment, at least 1.1 molar equivalent of excess free fatty acid is added to the reaction mixture.

In preferred embodiments, the isolated glycopyrronium fatty acid salt mixtures have an enrichment of the fatty acid (relative to glycopyrronium) compared to the input ratio. In embodiments using 1.2 molar equivalent of excess free fatty acid, the isolated products preferably have more than the 2.2:1 FA:GP input ratio. In some of these embodiments, the ratio is approximately between 2.25:1 and 3.00:1. In some of these embodiments, the ratio is approximately between 2.29:1 and 287:1.

In one example, a reaction mixture of glycopyrronium bromide with potassium laurate is stabilized with respect to the formation of the by-product (Acid A) by adding excess free lauric acid. Some preferred fatty acids include, but are not limited to, arachidic acid, stearic acid, palmitic acid, oleic acid, erucic acid, linoleic acid, arachidonic acid, lauric acid, capric acid, linolenic acid, or myristic acid. Some preferred salts for the fatty acid salt include, but are not limited to, Na, K, or Ca salts. In other embodiments, Mg or Ba salts may be used.

As described herein, excess free fatty acid is relative to the glycopyrronium bromide and fatty acid salt used. For example, for a lauric acid reaction with potassium, it is the excess free lauric acid relative to the glycopyrronium bromide and potassium laurate used.

The excess free fatty acid stabilizes the reaction mixture. The larger excesses of free fatty acid (0.6-1.2 molar excess) improved the phase separations, improved stability of the organic extract solutions, and improved stability of the isolated products.

There is potential to isolate a mixture of glycopyrronium fatty acid salt and excess free fatty acid to ensure a consistent, well defined product.

Ion Exchange

From the outset, the synthesis approach using ion exchange resins was challenging due to the known hydrolytic instability of glycopyrronium bromide at pH values above pH 5.6 (see, for example G Gupta, V. D., "Stability of Oral Liquid Dosage Forms of Glycopyrrolate Prepared With the Use of Powder", International Journal of Pharmaceutical Compounding, 2003, 7(5), 386-388, herein incorporated by reference) and the complexity and cost of the required technology. While aqueous solutions of glycopyrronium bromide are reasonably stable at ambient temperature at pH 5.6 and below, glycopyrronium bromide would be expected to rapidly hydrolyze at the ester linkage at the pH values required in a salt exchange process employing resins.

Starting from commercially available glycopyrronium bromide (structure 2 in Table 3B), the corresponding fatty acid salts (structure 1 in Table 3A) can in principle be derived through the use of anionic ion exchange resins. Table 4 provides an ion exchange flow diagram, which shows a schematic of how this may be accomplished.

TABLE 4

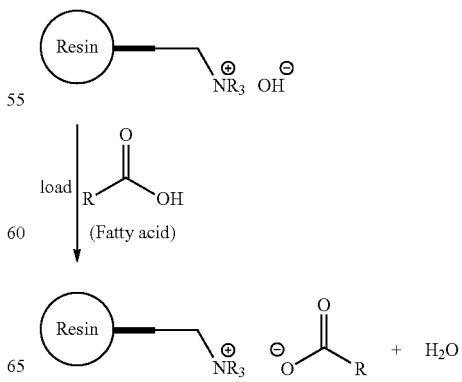

TABLE 4-continued

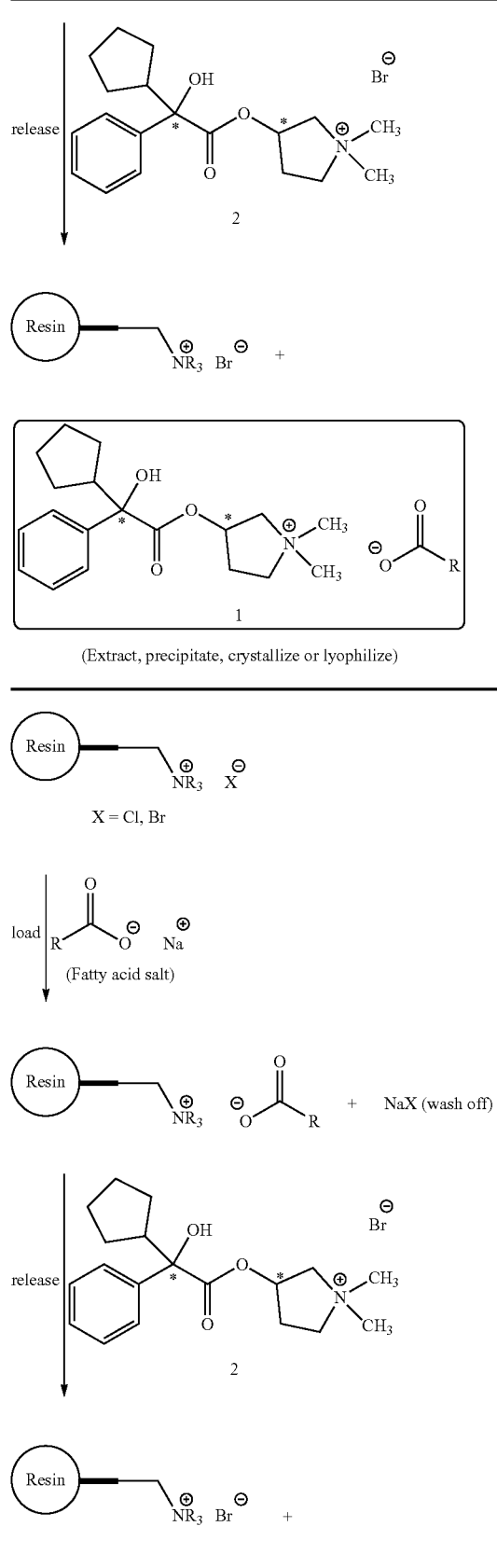

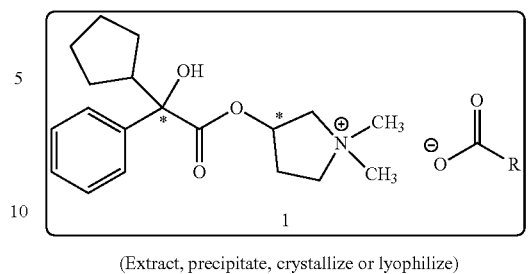

(Extract, precipitate, crystallize or lyophilize)

However, the ion exchange approach using resins requires expertise beyond standard synthesis methodologies. Besides the selection of a suitable resin, a number of parameters need to be carefully chosen to maximize the effectiveness of this process. Factors that impact the adsorption-desorption isotherms in ion exchange include, but are not limited to, the relative ratio of substrate to resin, the solvent system (eluent), the temperature, and the substrate concentration. The hydrophobic interactions between the resin and the fatty acid backbone may play an important role as well in binding efficiency (besides the electrostatic attraction of the polar groups). For this reason, the resin choice itself may be an important consideration (see, for example Ihara, Y. "Adsorption of Fatty Acid Sodium Salts on Ion Exchange Resins", Journal of Applied Polymer Science, 1986, 32(6), 5665-5667, herein incorporated by reference). In Ihara, the weakly basic resin with hydrophobic phenyl groups in the polymer (IRA94) showed a better performance than the less hydrophobic resin (IRA68). The adsorption efficiency of the fatty acid sodium salts dramatically increased, in going from C-6 to C-12 fatty acid salts.

An additional challenge with the ion exchange methodology is the instability of glycopyrrolate at elevated pH in aqueous solutions due to ester hydrolysis. This compound is reasonably stable at ambient temperature at pH 5.6 and below (Gupta, 2003) but is expected to be susceptible to hydrolysis of the ester under the processing conditions (as pH values will be substantially higher than pH 5.6).

The other two approaches were evaluated for the preparation of lipophilic glycopyrronium fatty acid salts.

Lauric acid was selected as a model fatty acid for the initial work. The exchange reaction of glycopyrronium bromide with potassium laurate was screened in various solvent systems.

The best solvent system was water/methyl tetrahydrofuran (Me-THF) which provided the desired product, glycopyrronium laurate. Unfortunately, the isolated oily product was unstable and decomposed into the by-product, Acid A. The decomposition products from attempted methylation of the glycopyrrolate base with dimethyl carbonate, which include Acid A and the methyl ester of Acid A, are shown in Table 5.

TABLE 5

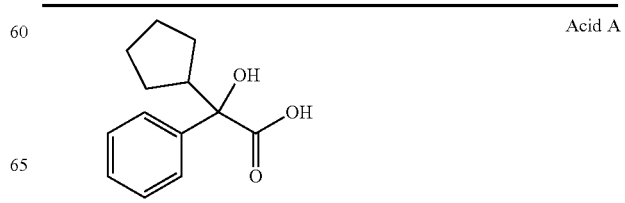

Acid A

TABLE 5-continued

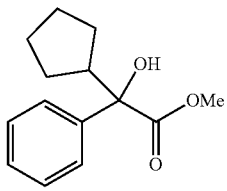 [SMILES: COC(=O)C(O)(c1ccccc1)C1CCCC1]

Methyl Ester of Acid A

Potassium stearate and potassium palmitate were also investigated in the Me-THF/water system in attempts to improve the stability of the target salts and to obtain the target materials in a solid form. These reactions failed to provide solid product(s) and showed a partial hydrolysis to Acid A during the process.

Direct Salt Metathesis (Counterion Exchange)

The reaction of glycopyrronium bromide with fatty acid salts was performed in organic solvents (anhydrous conditions) and biphasic (water/organic) conditions. The reactions in organic solvents did not result in any product formation, while using biphasic conditions provided the desired products in the reaction mixture.

The general chemistry of this process is shown below:

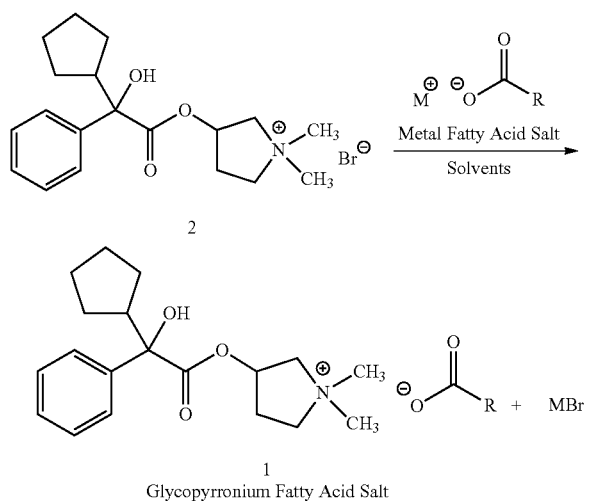

An example of the chemistry in this process is shown below:

Example

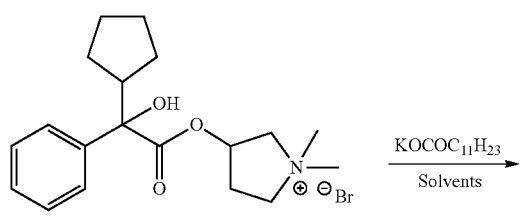

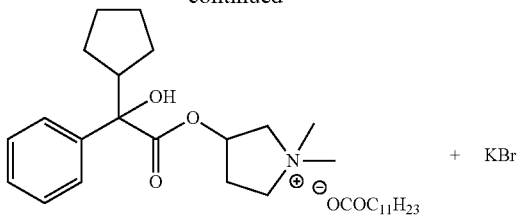

+ KBr

A direct salt metathesis ("ion swap") between glycopyrronium bromide and the sodium or potassium salt of representative fatty acids using an extractive process was successfully developed. In this process, the water soluble inorganic salt derived from the bromide exchange with the carboxylate conjugate base of the fatty acid is partitioned in the aqueous phase and removed from the reaction medium to drive the exchange process.

A direct counterion exchange between glycopyrronium bromide and suitable fatty acid salts was then evaluated. The driving force for a typical salt metathesis reaction is the generation of an insoluble salt that precipitates out of solution. In the case of fatty acid salts, the most likely starting materials would be the corresponding silver salts. For example, see US patent publication 2011/0306650, published Dec. 15, 2011, and incorporated herein by reference, which describes the preparation of glycopyrronium chloride by reacting glycopyrronium bromide with silver acetate to produce glycopyrronium acetate (silver bromide precipitates out). The acetate salt is then reacted with HCl to produce the glycopyrronium chloride (along with acetic acid). Glycopyrronium sulfate is produced similarly by salt metathesis using silver sulfate. Such starting materials were not desirable due to concerns over heavy metal residues in the drug substance, as they were expected to be difficult to fully remove from the desired glycopyrronium fatty acid salts and require special waste disposal considerations for the precipitated silver salts on large scale (preferably via metal recovery).

Nonetheless, a proper solvent choice in combination with the fatty acid salts of innocuous metals such as sodium, potassium or calcium was considered for assessment of counterion exchange through precipitation of the derived bromide salts (sodium, potassium or calcium bromide). Alternatively, the counterion exchange reaction could be driven by extracting the highly soluble inorganic salt into the aqueous phase.

Figure 2:
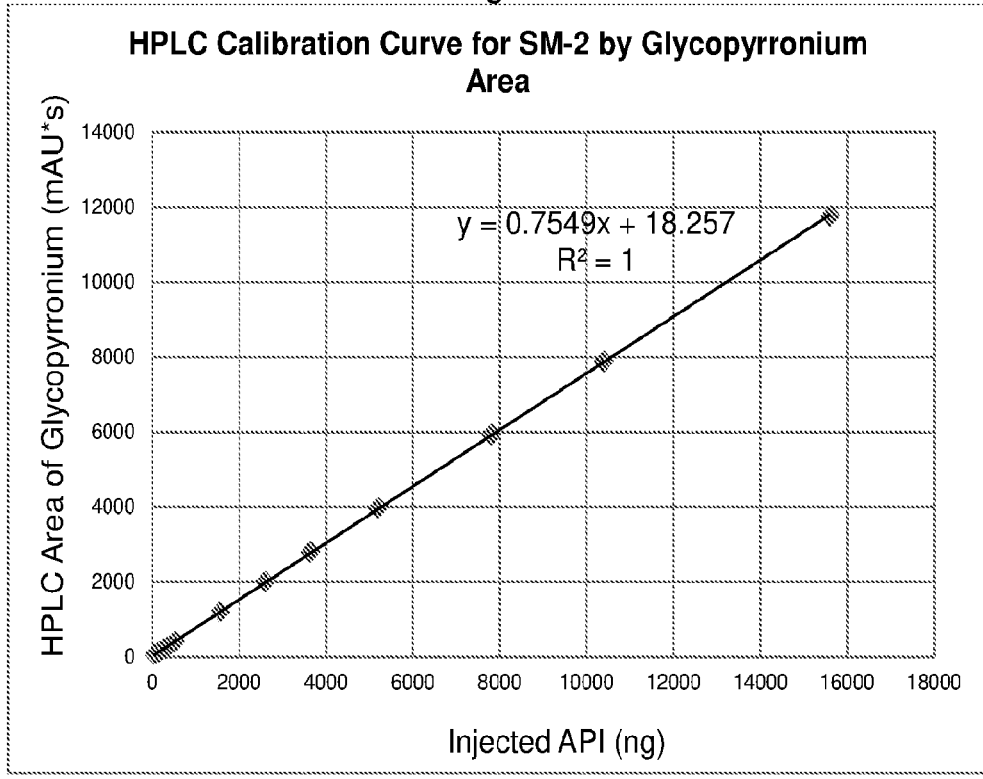
FIG. 2 shows the HPLC Calibration Curve for glycopyrronium bromide by "Glycopyrronium" Peak.

In order to select the reaction solvents, the glycopyrronium bromide (GPBr-structure 2 in Table 3B) solubility in various solvents was determined using HPLC calibration curves (see FIGS. 1 and 2). The results of glycopyrronium bromide solubility in various solvents at room temperature are summarized in Table 6 below. The experiment was conducted with 50 mg of glycopyrronium bromide and 1 mL of solvent in most cases. The mixture was stirred at room temperature for 24 hours and then filtered to afford a clear filtrate. The filtrate was diluted with acetonitrile and checked by HPLC.

TABLE 6

| Solvents | At Room Temperature | Note |
| --- | --- | --- |
| Water | >840 mg/mL | Additional GPBr was used |
| Methanol | >541 mg/mL | Additional GPBr was used |
| Ethanol | 142 mg/mL | Additional GPBr was used |

TABLE 6-continued

| Solvents | At Room Temperature | Note |
|---|---|---|
| IPA | 26 mg/mL | |
| 2-Butanol | 24 mg/mL | |
| tert-Butanol | 4.8 mg/mL | |
| Acetone | 5.4 mg/mL | |
| MEK | 0.4 mg/mL | |
| MIBK | <0.1 mg/mL | Out of calibration limit |
| THF | <0.1 mg/mL | Out of calibration limit |
| Me-THF | <0.1 mg/mL | Out of calibration limit |
| DCM | 31 mg/mL | |

Three lauric acid salts (Na, K, and Ca) were prepared as model salts. These salts were prepared following the procedure in Zacharie et al. ("A Simple and Efficient Large-Scale Synthesis of Metal Salts of Medium-Chain Fatty Acids", Organic Process Research & Development 2009, 13, 581-583), herein incorporated herein by reference.

Preparation of Sodium Laurate

Lauric acid (50.08 g, 1.0 eq.) was dissolved in ethanol (500 mL, 10 vol., 95% denatured) at room temperature and reacted with NaHCO$_3$ (18.9 g, 0.9 eq.) in ethanol (500 mL, 10 vol., 95% denatured) at refluxing temperature. The reaction mixture (suspension) was stirred at refluxing temperature (~77° C.) overnight. Some solids precipitated overnight (vs. solution reported in literature) and the mixture was diluted with additional ethanol (~1.5 L). The solution was decanted and cooled to room temperature over four hours (solid product precipitated at ~55° C.). The slurry was filtered and the product was washed with MTBE (3×200 mL) to remove excess free un-reacted lauric acid. The white wet cake was dried in the air over the weekend and in a vacuum oven at 50±5° C. overnight to afford 27.2 g (54.4% yield) of white solid. While the yield was lower than in the prior art literature, the procedure could be optimized for better yield. Some methods for improving yield include, but are not limited to, optimizing the concentration during the crystallization process or using an antisolvent to decrease the solubility of the product and improve the yield.

Preparation of Potassium Laurate

The second experiment was conducted with 25 g (1.0 eq.) of lauric acid and 11.25 g of KHCO$_3$ (0.9 eq.) in ethanol (250 mL) at reflux. The product was crystallized from ethanol/MTBE (1/1) to afford 22.1 g (82.5% yield) of potassium laurate after drying in the air over the weekend and in a vacuum oven at 50±5° C. overnight.

In order to select the reaction solvents and their optimized volumes, the solubility of potassium laurate in various solvents was checked by adding solvent to dissolve the solids under sonication. A vial was charged with potassium laurate (~100 mg) and then solvent was added dropwise under sonication. The potassium laurate could not be dissolved with most solvents (200 vol.). The results of potassium laurate solubility in various solvents are summarized in Table 7 below:

TABLE 7

| Solvents | At Room Temperature | At 50° C. |
|---|---|---|
| Water | ~138 mg/mL | NA |
| Methanol | ~50 mg/mL | NA |
| Ethanol | ~14 mg/mL | NA |
| IPA | <5 mg/mL | <5 mg/mL |
| Methyl Acetate | <5 mg/mL | <5 mg/mL |
| Ethyl Acetate | <5 mg/mL | <5 mg/mL |
| Isopropyl Acetate | <5 mg/mL | <5 mg/mL |
| Butyl Acetate | <5 mg/mL | <5 mg/mL |
| Acetone | <5 mg/mL | <5 mg/mL |
| MEK | <5 mg/mL | <5 mg/mL |
| MIBK | <5 mg/mL | <5 mg/mL |

Preparation of Calcium Laurate

The third experiment was conducted with 15.6 g (1.0 eq.) of lauric acid and 2.6 g of Ca(OH)$_2$ (0.9 eq.) in ethanol (450 mL) at reflux for 4 hours. The product precipitated at reflux temperature. The reaction mixture was further diluted with methanol (500 mL) at reflux temperature. The slurry was cooled to room temperature and filtered then rinsed with an MTBE wash. The solid was dried in the air overnight and in a vacuum oven at 50±5° C. overnight to afford 10.4 g of white solid (67.7% yield). The procedure could be optimized to increase yield. Some methods for improving yield include, but are not limited to, optimizing the concentration during the crystallization process or using an antisolvent to decrease the solubility of the product and improve the yield.

Reaction in Organic solvents

Salt metathesis via precipitation was attempted using potassium laurate, sodium laurate, potassium stearate and potassium palmitate, in combination with acetone, methanol and dichloromethane as solvents.

Potassium laurate was selected as the model fatty acid salt for this approach. The first attempted reaction was conducted in anhydrous acetone. Glycopyrronium bromide (0.508 g, 1.0 eq.) was charged into a 250 mL flask followed by acetone (50 mL). Potassium laurate (1.1 eq.) was added to the mixture. The mixture was stirred and additional acetone (100 mL) was added in an attempt to dissolve the solids. The solids failed to dissolve completely. The mixture was stirred overnight and was then concentrated to a residue. Ethyl acetate (EtOAc, 100 mL) was used to extract the crude residue. The extract was concentrated to afford only 48 mg (less than 10% wt recovery) of an oily residue. HPLC analysis of the residue showed that several peaks were present. Proton NMR analysis showed that a complex mixture was obtained.

The reaction failed to provide the desired product, most likely due to the low solubility of both the glycopyrronium bromide and the potassium laurate.

Since both starting compounds are soluble in methanol, the next reaction was attempted in methanol. Glycopyrronium bromide (1.036 g, 1.0 eq.) was charged into a 20 mL vial followed by methanol (5 mL) to dissolve all solids. A potassium laurate solution in methanol (0.691 g, 1.1 eq., 10 mL of methanol) was added to the mixture. The mixture was stirred over the weekend at ambient temperature and then the solution was checked by HPLC which showed that one new peak (RRT=1.37) was formed at ~47% HPLC AUC. The solution was concentrated to remove methanol and then extracted with EtOAc (3×100 mL). The EtOAc extracts were combined and concentrated to an oily residue (0.8 g). HPLC analysis showed that the new peak was enriched to 61% AUC. Proton NMR analysis showed that a methyl ester peak at 3.77 ppm was formed. The proposed structure for this by-product follows:

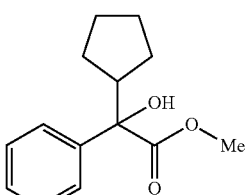

Proposed by-product

The solid (0.87 g) remaining after the EtOAc extraction was checked by HPLC which showed that the major peak was "Bromide" with ~91% AUC. However, proton NMR analysis suggested that the solid was a mixture of at least three possible compounds listed in Table 8 below.

TABLE 8

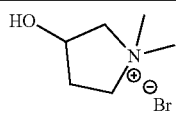

Proposed by-Product

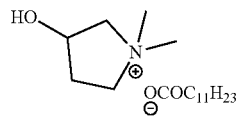

Proposed by-Product

The glycopyrronium fatty acid salt was unstable in the methanolic reaction mixture. However, it was confirmed that the starting material, glycopyrronium bromide (structure 2 in Table 3B), in the absence of other components, is stable in methanol.

To explore the exchange reactions under anhydrous conditions, four fatty acid salts (potassium laurate, sodium laurate, potassium stearate, and potassium palmitate) were tested by suspending the reactants in dichloromethane (DCM) and stirring for 90 h at room temperature. Any precipitation of potassium bromide (or sodium bromide) was expected to provide enrichment of the glycopyrronium peak relative to the bromide peak in the HPLC analysis of the filtered DCM solutions. The reaction mixture (DCM, 1.0 mL) was filtered through a syringe filter, concentrated, and the resulting solid residue was dissolved in a mobile phase and analyzed by HPLC. The HPLC results of the exchange reactions in an anhydrous DCM system are shown in Table 9 below.

TABLE 9

| Sample Name | Sample Information | HPLC area ratio of "Bromide"/ "Glycopyrronium" | Comments |
|---|---|---|---|
| GPBr | API (Bromide Salt) | 1:18 | Standard Solution |
| XL-007-102 | Potassium Laurate | 1:15.6 | No loss of bromide |
| XL-007-103 | Sodium Laurate | 1:17.8 | No loss of bromide |

TABLE 9-continued

| Sample Name | Sample Information | HPLC area ratio of "Bromide"/ "Glycopyrronium" | Comments |
|---|---|---|---|
| XL-007-104 | Potassium Stearate | 1:17.0 | No loss of bromide |
| XL-007-105 | Potassium Palmitate | 1:16.4 | No loss of bromide |

The bromide/glycopyrronium ratio clearly indicated that no enrichment of glycopyrronium relative to bromide had taken place. No desired product was observed using anhydrous conditions (DCM) with potassium laurate, sodium laurate, potassium stearate or potassium palmitate.

All attempts were unsuccessful due to solubility issues (low solubility of glycopyrronium bromide in acetone), instability (transesterification reaction in methanol) and insufficient solubility difference (in dichloromethane).

Reaction in Biphasic Conditions

An alternative approach whereby the exchange process is accomplished in a biphasic solvent mixture was more successful. A counterion exchange via selective extraction is shown in Table 10.

TABLE 10

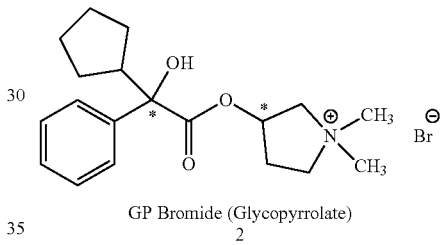

GP Bromide (Glycopyrrolate)
2

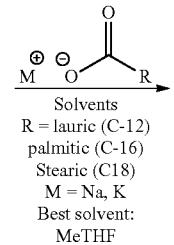

Solvents
R = lauric (C-12)
palmitic (C-16)
Stearic (C18)
M = Na, K
Best solvent:
MeTHF

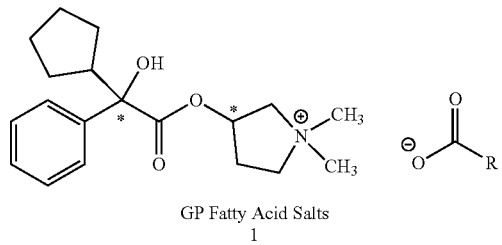

GP Fatty Acid Salts
1

Six solvents were evaluated in the extractive procedure: 2-methyl tetrahydrofuran (MeTHF), methyl tert-butyl ether (MTBE), isopropyl acetate (IPAc), methyl isobutyl ketone (MIBK), toluene, and dichloromethane (DCM). Using sodium laurate as the model fatty acid salt, MeTHF was determined to be the best solvent, affording an organic phase that was highly enriched in glycopyrronium laurate.

Further experiments using potassium laurate, potassium palmitate and potassium stearate demonstrated the generality of this methodology. The reaction products were characterized by proton NMR analysis and confirmed to be consistent with the fatty acid salts. HPLC analysis using a developmental HPLC method showed enrichments of up to 96% area/area following 3-4 aqueous washes of the MeTHF extracts.

A hydrolysis side reaction was observed to be a significant problem in the counterion exchange process at the prevailing pH (8.0-8.3). This issue was resolved by using an excess of the free fatty acid to "buffer" the medium and minimize the hydrolysis reaction, and by performing the exchange and further processing of the materials at ambient temperature.

Since both starting compounds are very soluble in water, the reaction was attempted in water/Me-THF. Glycopyrronium bromide (structure 2 in Table 3B) (1.0 eq.) was charged into a 20 mL vial followed by water (2 mL) to dissolve all solids. The glycopyrronium bromide solution was transferred into a solution of potassium laurate in water (1.1 eq., 5 mL of water) in a 20 mL vial. The glycopyrronium bromide vial was rinsed with water (3×1 mL) and the rinse was transferred into the reaction vial. HPLC analysis showed that the area ratio of the "Bromide" peak to the "Glycopyrronium" peak was 20/80. Me-THF (10 mL) was added to the reaction solution. The mixture was stirred for one hour and then settled for phase separation. Both layers were checked by HPLC and it was found that the area ratio of the "Bromide" peak to the "Glycopyrronium" Peak was significantly different between the two layers (XL-007-071-1 and XL-007-071-2, Table 11 below). The reaction mixture was then re-mixed for one hour and then settled for one hour to afford two layers (XL-007-071-3 and XL-007-071-4). HPLC analysis showed that the ratio of the two peaks was unchanged. The results showed that more "Bromide" was contained in the aqueous layer and the "Glycopyrronium" was extracted into the Me-THF layer. The aqueous layer was removed, replaced with fresh water, mixed and then settled to afford two layers (XL-007-071-5 and XL-007-071-6). HPLC analysis showed that the Me-THF layer contained 93 area % of "Glycopyrronium". The Me-THF layer was washed with water an additional two times and the product in the Me-THF layer was enriched to 96 area % (XL-007-071-10). The HPLC results for the aqueous and organic layers of the reaction mixture are shown in Table 11.

TABLE 11

| Sample Name | Sample Information | HPLC Area Ratio of "Bromide"/"Glycopyrronium" | |
|---|---|---|---|
| XL-007-071-0 | Initial Water solution of both components | 20/80 | |
| XL-007-071-1 | Aqueous Layer | 80/20 | |
| XL-007-071-2 | Me-THF Layer | 11/89 | |
| XL-007-071-3 | Aqueous Layer | 80/19 | Repeated |
| XL-007-071-4 | Me-THF Layer | 11/89 | Repeated |
| XL-007-071-5 | Aqueous Layer | 68/32 | After first water wash |
| XL-007-071-6 | Me-THF Layer | 7/93 | |
| XL-007-071-7 | Aqueous Layer | 27/73 | After second water wash |
| XL-007-071-8 | Me-THF Layer | 6/94 | |
| XL-007-071-9 | Aqueous Layer | 7/93 | After third water wash |
| XL-007-071-10 | Me-THF Layer | 4/96* | |

One aliquot sample from the washed Me-THF layer (XL-007-071-10) was taken and concentrated to an oil which was analyzed by proton NMR in different solvents (CDCl$_3$, DMSO-d$_6$, and D$_2$O) for comparison against the starting materials. The proton NMR spectrum was consistent with the expected spectrum of the desired product:

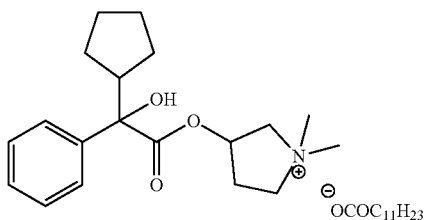 [SMILES: C[N+]1(C)CCC(OC(=O)C(O)(c2ccccc2)C2CCCC2)C1 ; "OCOC11H23"]

To improve upon the selective solubility and partitioning of bromide and fatty acid salt between the aqueous and solvent layers, the reaction of glycopyrronium bromide (structure 2 in Table 3B) with sodium laurate was screened in the following six solvents with water: Methyl tetrahydrofuran (Me-THF), Methyl tert-butyl ether (MTBE), Isopropyl acetate (IPAc), 4-Methyl-2-pentanone(MIBK), Toluene, and Dichloromethane (DCM).

The reaction was conducted with glycopyrronium bromide (100 mg, 1.0 eq.) and sodium laurate (61 mg, 1.1 eq.) with 7 mL of water and 7 mL of organic solvent at room temperature. The reaction mixture was stirred over four days and then settled. Both layers were checked by HPLC and the analytical results for the sodium laurate/glycopyrronium bromide exchange are summarized in Table 12 below:

TABLE 12

| | | HPLC Area Ratio of "Bromide"/"Glycopyrronium" | |
|---|---|---|---|
| Experiment | Solvent System | Organic Layer | Aqueous Layer |
| 1 | Me-THF/water | 18/82[1] | 46/54[1] |
| 2 | MTBE/water | 25/75[2] | 30/70[1] |
| 3 | IPAc/water | 80/20[2] | 30/70[1] |
| 4 | Toluene/water | 40/60[2] | 26/74[1] |
| 5 | MIBK/water | 72/28[2] | 29/71[1] |
| 6 | DCM/water | 65/35[2] | 38/62[1] |

[1]Decomposed product (Acid A) was observed in significant amounts by HPLC
[2]HPLC peak areas were very small.

From these six experiments, Me-THF was the best solvent for selective product partition and extraction. Unfortunately, the decomposition product (Acid A, RRT=0.74) was observed in both the organic layer and aqueous layer.

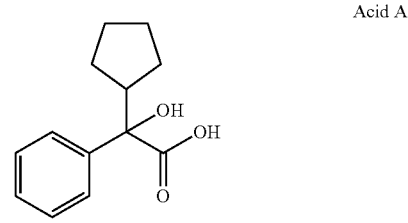 [SMILES: O=C(O)C(O)(c1ccccc1)C1CCCC1]

Acid A

Me-THF was selected for further investigation based on the results of the solvent screening. The reaction using potassium laurate and Me-THF was scaled up to 4.89 g of glycopyrronium bromide with potassium laurate (3.07 g, 1.05 eq.) in 25 mL of water and 53 mL of methyl THF at room temperature. The mixture was stirred for one hour and settled for phase separation. Three layers formed and each was checked by HPLC and the results of the scale up reaction in water/Me-THF are summarized in Table 13. It was confirmed that an additional peak ($t_R$=5.29 min, RRT=0.74) was detected and that this peak increased over time. This peak was confirmed to be the by-product, Acid A, by comparison with a separate preparation and isolation of Acid A. Acid A, the hydrolysis product of glycopyrrolate base (structure 3 in Table 3B) was isolated and characterized by HPLC and NMR ($^1$H and $^{13}$C).

The bottom layer (aqueous) was removed and the top two layers were washed with water (3×20 mL). It was observed that only two layers were formed after the first phase separation. The final organic layer (XL-007-080-4 A) was concentrated at 60° C. on a rotary evaporator to afford a residue which was re-dissolved with methyl THF (100 mL). The insoluble solids (KBr and potassium laurate) were filtered and dissolved with water and then checked by HPLC (XL-007-080-P1). The filtrate was concentrated to dryness to afford an oil (6.12 g, XL-007-080-P2) and HPLC analysis showed that the bromide peak was reduced to 1.34 area %. The product was dried in a vacuum oven at 50° C. over the weekend. NMR analysis of the dried product showed some decomposition. The dried oily product was dissolved with MTBE (100 mL) and precipitation was attempted by adding n-heptane, resulting in two liquid layers. Both layers were checked by HPLC (Top layer: XL-007-082-1 and bottom layer: XL-007-082-2) and showed high levels of the by-product, Acid A.

-continued

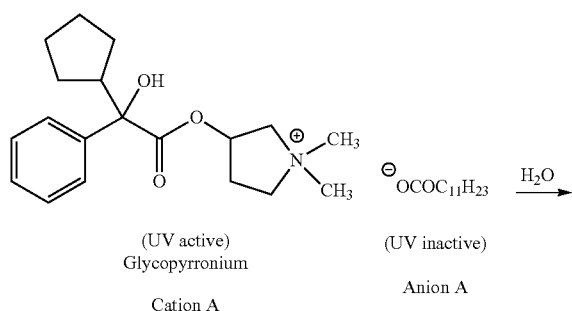

(UV inactive)
Cation B (UV active)
Anion B $C_{11}H_{23}CO_2H$
(UV inactive)
Free Fatty Acid The nature of the reaction mixture, which included components with strong chromophores and others that had weak chromophores (for all intents and purposes herein labeled as "UV inactive") rendered the accurate analysis and quantitation of all components in the mixtures very challenging.

TABLE 13

| Sample | | HPLC Results (AUC) | | | |
|---|---|---|---|---|---|
| ID | Information | Bromide | Acid A | Glycopyrronium | |
| XL-007-080-1A | Top Layer | 13.57% | 0.51% | 85.92% | |
| XL-007-080-1B | Middle Layer | 14.37% | 0.50% | 85.13% | |
| XL-007-080-1C | Bottom Layer | 85.61% | ND | 14.39% | Phase Removed |
| XL-007-080-2C | Bottom Layer | 76.66% | ND | 23.34% | Phase Removed |
| XL-007-080-3A | Top Layer | 3.65% | 1.44% | 94.91% | |
| XL-007-080-3C | Bottom Layer | 62.93% | ND | 37.07% | Phase Removed |
| XL-007-080-4A | Top Layer | 1.85% | 1.83% | 96.32% | |
| XL-007-080-4C | Bottom Layer | 24.96% | 2.80% | 71.23% | Phase Removed |
| XL-007-080-P1 | Filtered Solids | 12.88% | ND | ND | Potassium Laurate as major peak (lower response) |
| XL-007-080-P2 | Oil Product | 1.34% | 4.84% | 93.82% | |
| XL-007-082-1 | Top Layer | 0.83% | 12.37% | 86.80% | |
| XL-007-082-2 | Bottom Layer | 1.01% | 15.06% | 83.94% | |

It was confirmed that the isolated oily product had partially decomposed. Most likely, this decomposition is consistent with a hydrolysis reaction, which is facilitated at elevated temperature and elevated pH. The proposed decomposition reaction scheme is shown below:

For this reason, orthogonal and complementary analytical methods were developed to facilitate both the in-process analysis of the reactions and the assessment of both the purity and the composition of the isolated reaction products.

The desired product, glycopyrronium laurate, was isolated by Me-THF extraction from an aqueous solution of glycopyrronium bromide and potassium laurate. Unfortunately, the isolated product was unstable during the isolation process with the levels of Acid A increasing over time. The isolated product degraded at 50° C. from ~94 area % to 83-86 area % over a weekend. Glycopyrronium bromide itself was stable in the HPLC diluent solution (ACN/water) at ambient temperature over two weeks (by HPLC).

The preparation of glycopyrronium laurate was repeated at 5.0 g scale (GPBr). The HPLC results of the repeated scale-up reaction in water/ME-THF are summarized in Table 14 below. It was confirmed by HPLC that the decomposition product Acid A, was formed during the work up and isolation.

TABLE 14

| Sample | | HPLC Results (AUC) | | | |
|---|---|---|---|---|---|
| ID | Information | Bromide | Acid A | Glycopyrronium | pH |
| XL-007-091-A | First aq. Layer | 84.70% | 0.78% | 14.52% | 8.00 |
| XL-007-091-B | Second aq. Layer | 74.82% | 1.46% | 23.72% | 8.00 |
| XL-007-091-C | Third aq. Layer | 57.96% | 2.97% | 39.08% | 8.07 |
| XL-007-091-D | Fourth aq. Layer | 19.51% | 4.90% | 75.59% | 8.25 |
| XL-007-091-1 | Me-THF Layer (final) | 4.31% | 4.12% | 91.06% | |
| XL-007-091-2 | Me-THF layer after overnight ambient | 3.25% | 6.07% | 90.67% | |

The Me-THF solution was stress-tested at room temperature and at 50° C. over the weekend with and without the addition of an excess of free lauric acid. The results of the stress test are listed in Table 15. While the room temperature solutions showed far less degradation than the heated samples, decomposition was still significant. The attempt to stabilize the product with excess free lauric acid resulted in less decomposition being observed than in the corresponding samples without excess free lauric acid. It was noted that the Me-THF solutions split into two layers at 50° C. This was likely due to a decrease in the solubility limit of water in the mixture upon heating.

Without excess free lauric acid, the product slowly decomposed at ambient temperature from 90.67 area % product content to 87.72% in the Me-THF solution. At 50° C., the product decomposed significantly, to only 57 area % in the top layer and ~50% in the bottom layer. In the presence of excess free lauric acid at ambient temperature, the product showed only slight decomposition (Expt. 2 A) while at 50° C., the product decomposed, leaving only ~65-70 area %, even with excess free lauric acid present.

TABLE 15

| | | | HPLC Results (AUC %) | | |
|---|---|---|---|---|---|
| Expt. | Conditions | | Bromide | Acid A | Glycopyrronium |
| 0 | Initial Me—THF Solution | | 3.25% | 6.07% | 90.67% |
| 1A | Me—THF Solution at RT over weekend | | 3.02% | 9.26% | 87.72% |
| 1B | Me—THF Solution at 50° C. over weekend | Top | 2.79% | 40.08% | 57.13% |
| | | Bottom | 4.07% | 46.08% | 49.47% |
| 2A | Me—THF Solution in the presence of Lauric Acid at RT over weekend | | 3.95% | 6.61% | 89.44% |
| 2B | Me—THF Solution in the presence of Lauric Acid at 50° C. over weekend | Top | 2.07% | 28.36% | 69.58% |
| | | Bottom | 4.38% | 30.01% | 65.60% |

The desired product in Me-THF degraded over time. The product degraded significantly faster at 50° C. With the presence of excess free lauric acid (approximately 1.0 molar equivalent excess), the product decomposition was slower especially at ambient temperature.

A Me-THF extraction of the aqueous solution of glycopyrronium bromide and potassium laurate produced the desired product but the desired product was unstable during the extraction process at room temperature. The observed decomposition product was confirmed by independent preparation and isolation to be the hydrolysis product (Acid A). It was confirmed that the product decomposed significantly faster at 50° C. The isolated crude product was oily and failed to precipitate from heptane and other solvents (MTBE, IPAc, and EtOAc).

Since the oily product obtained from potassium laurate was unstable, fatty acids with longer chains were tested in an attempt to get solid products with potentially improved stability.

Potassium stearate and potassium palmitate were prepared and tested with glycopyrronium bromide in the Me-THF/water system.

Stearic acid and palmitic acid were used as the potassium salts. The preparations of potassium stearate and potassium palmitate were performed following the procedures from Zacharie et al. ("A Simple and Efficient Large-Scale Synthesis of Metal Salts of Medium-Chain Fatty Acids", Organic Process Research & Development 2009, 13, 581-583), which are summarized below.

For the preparation of potassium stearate, stearic acid (25.0 g, 1.0 eq.) was dissolved in ethanol (500 mL, 20 vol., 95% denatured) at 45° C. in a 2-L round bottom flask. $KHCO_3$ (7.88 g, 0.9 eq.) was added into the solution and then the reaction mixture was heated to reflux (~77° C.). The reaction was stirred overnight (21 hours) at reflux. MTBE (500 mL) was added to the solution at 65° C. Some foaming occurred and vigorous stirring was needed to break the foam. A second portion of MTBE (500 mL) was then added at 50° C. and the resulting slurry was cooled to room temperature over approximately 3 hours. The slurry was filtered and the wet cake was washed with MTBE (3×125 mL). The white wet cake was dried in a vacuum oven at ~50° C. overnight to afford a white solid product (25.4 g, quantitative yield).

For the preparation of potassium palmitate, palmitic acid (15.0 g, 1.0 eq.) was dissolved in ethanol (200 mL, 95% denatured) at 40° C. in a 1-L round bottom flask. Solid $KHCO_3$ (5.27 g, 0.9 eq.) was added into the solution and then the reaction mixture was heated to reflux (~77° C.). The reaction was stirred overnight (20 hours) at reflux. MTBE (100 mL) was added to the solution at 65° C. and a solid product precipitated. A second portion of MTBE (100 mL)

was then added and the resulting slurry was cooled to room temperature over approximately 3 hours. The slurry was filtered and the wet cake was washed with MTBE (3×100 mL). The white wet cake was dried in a vacuum oven at ~50° C. overnight to afford a white solid product (14.7 g, 94.8% yield).

The exchange reactions were performed by dissolving the fatty acid salt with glycopyrronium bromide in Me-THF/water, stirring for 5.0 h at room temperature, then separating the phases and washing the organic phase with water. The HPLC analytical results of both Me-THF and water layers are shown in FIG. 3 (potassium stearate) and 4 (potassium palmitate). The exchange reactions with potassium stearate and potassium palmitate did not provide the desired products free of the Acid A impurity. After concentration of the extracts, both reactions gave sticky oily residues that were difficult to isolate. Neither offered an advantage over the results from potassium laurate.

Stabilization of Exchange Reactions by Adding Excess free Fatty Acid

In an attempt to stabilize the glycopyrronium laurate product and avoid the decomposition of glycopyrronium to Acid A, the Me-THF/water reaction system was tested with excess free lauric acid (1.1 molar equivalent excess relative to glycopyrronium bromide). Two experiments with and without excess free lauric acid were conducted by mixing two solutions of glycopyrronium bromide (1.04 g, 1.0 eq.) in water (5 mL) and potassium laurate (1.1 eq.) in water (5 mL) with Me-THF (20 mL) with and without excess lauric acid (1.1 eq.) at room temperature overnight. For each reaction, both layers were checked by HPLC with the results of the HPLC for the exchange reaction with excess free lauric acid summarized in Table 16 below. The reaction with excess free lauric acid showed no formation of the by-product, Acid A, after mixing overnight but the experiment without excess free lauric acid, had Acid A in both layers.

TABLE 16

| | HPLC Area Ratio of "Bromide"/"Glycopyrronium" | |
|---|---|---|
| Experiment | Me—THF Layer | Aqueous Layer |
| Without Lauric Acid[1] | 9.1/90.9[1] | 80.8/19.2[2] |
| With Excess free Lauric Acid (1.1 eq.) | 7.4/92.6[3] | 80.6/19.4 |

[1]5.5 area % of Acid A was observed in the Me—THF layer.
[2]2.2 area % of Acid A was observed in aqueous layer.
[3]The lauric acid peak co-eluted in glycopyrronium peak.

Adding 1.1 molar equivalents of excess free lauric acid into a preparation with potassium laurate and glycopyrronium bromide in the water/Me-THF system stabilized the reaction mixture.

Bi-phasic reaction conditions enabled the desired exchange reactions between glycopyrronium bromide and alkali and alkaline earth metal salts of fatty acids. Favorable partitioning of the glycopyrronium moiety into the organic phase (along with the fatty acids) and partitioning of the bromide into the aqueous phase was achieved with water and methyl tetrahydrofuran. The glycopyrronium fatty acid salts were unstable with respect to hydrolysis under the reaction conditions and were unstable as isolated oily products. The formation of the impurity, Acid A, was noted over time. An excess of the free fatty acid in the reaction mixture stabilized the glycopyrronium fatty acid salt and reduced the formation of the impurity, Acid A.

Reaction with Methyl Carbonates

In the prior art, dimethyl carbonate chemistry has been mostly employed in the surfactants and detergents industry as well as in the manufacture of ionic liquids with counterions that are different from halides.

The reaction of glycopyrrolate base with methyl carbonate and subsequent treatment with fatty acids failed to provide any of the desired product(s) and produced only decomposition products from the glycopyrrolate base.

One example of the chemistry involved in this process is shown below:

Example

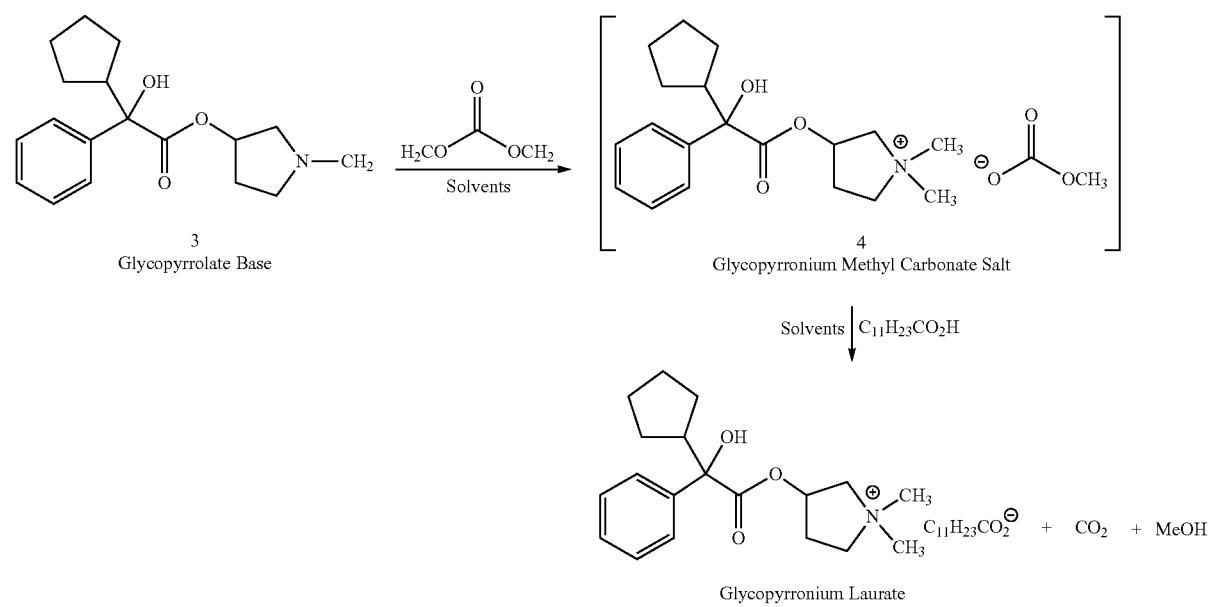

The synthesis approach proceeding through methyl carbonates was unsuccessful, due to the instability of the starting glycopyrrolate base (compound 3 in Table 17) and its quaternization reaction products (glycopyrronium methyl carbonates, compound 4 in Table 17) under the high temperature and pressure conditions required for a successful quaternization reaction with dimethyl carbonate.

Since a clean synthesis of the required methyl carbonated salt of glycopyrronium could not be accomplished, this approach was discontinued and subsequent efforts focused on a direct salt metathesis using glycopyrronium bromide.

Tertiary amines can be alkylated with dimethyl carbonate to generate the corresponding quaternary methyl ammonium carbonate salts in good to high yields. Subsequent reaction with a proton source leads to a clean ion metathesis reaction via decomposition of the methyl carbonate counterion into $CO_2$ and methanol, which are readily removed from the reaction mixture to yield products with high purity.

TABLE 17

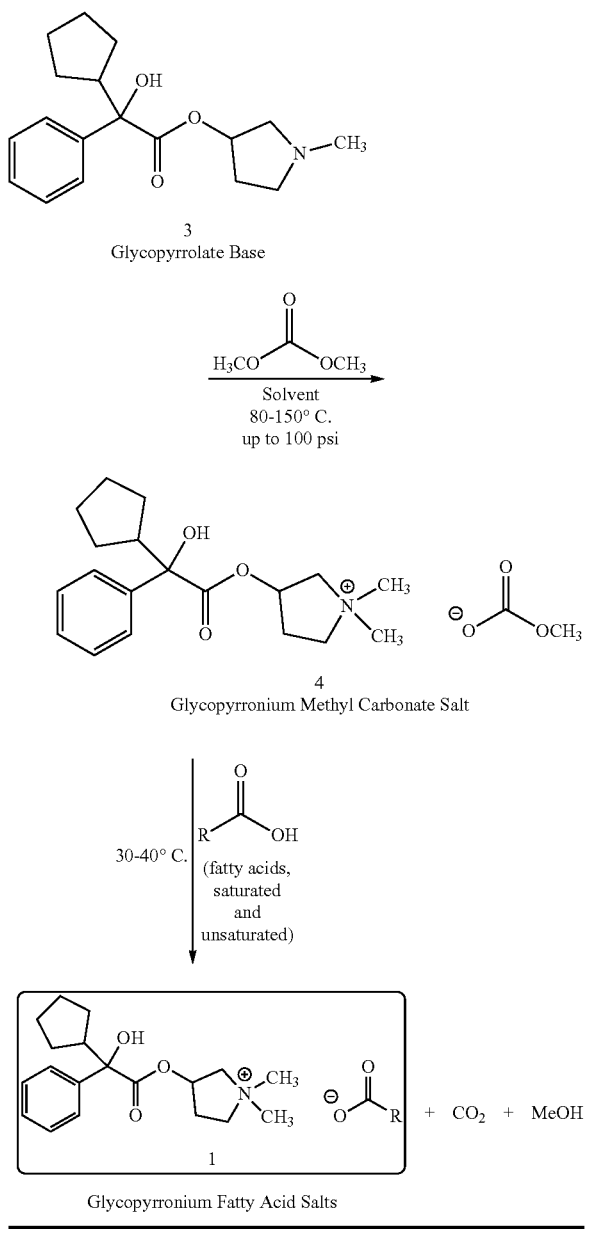

Table 17 shows the sequence of steps for synthesis of glycopyrronium salts of fatty acids via methyl carbonates from glycopyrrolate base.

The alkylation reaction requires high temperatures (typically 80-150° C., depending of the reactivity of the tertiary amine) and is run under pressure, as dimethyl carbonate has a boiling point of 90° C. Heterocyclic tertiary amines are reported to react faster and at relatively lower temperatures than the sterically crowded aliphatic tertiary amines. For example, Mori et al., U.S. Pat. No. 4,892,944, issued Jan. 9, 1990 and incorporated herein by reference, report that N-methyl pyrrolidine (the closest structural motif to the glycopyrrolate base 3) can be quaternized at 120° C. to afford the corresponding methyl carbonate salt in 97% isolated yield after a 6 hour reaction. Bicyclic amines bearing a nitrogen atom at the bridgehead, which are known to be even more nucleophilic, react readily at atmospheric pressure under refluxing conditions (80-90° C.) to afford the methyl carbonates in high yields. (see Friesen et al., US Patent Publication 2012/0321969, published Dec. 20, 2012, herein incorporated by reference).

The quaternization reaction was evaluated in neat dimethyl carbonate, and in two non-nucleophilic solvents, t-amyl alcohol and dimethyl acetamide, which were expected to be unreactive toward the starting glycopyrrolate base. The glycopyrrolate base, compound 3, was custom made by Shanghai Chempartner (China) based on a published procedure (see Allmendinger et al., "Carry Over of Impurities: A Detailed Exemplification for Glycopyrrolate (NVA237)", Organic Process Research & Development 2012, 16, 1754-1769, herein incorporated by reference).

Four reactions of glycopyrrolate base (structure 3 in Table 3B) with dimethyl carbonate (shown in Table 18) were attempted. For the general procedure, glycopyrrolate base (structure 3 in Table 3B) was charged into a Fisher-Porter pressure bottle followed by methyl carbonate and solvent. The solution was purged with nitrogen three times under slight vacuum and then the reactor was sealed. The reaction mixture was stirred and heated with oil bath. The detailed reaction conditions and results are summarized in FIG. 5.

TABLE 18

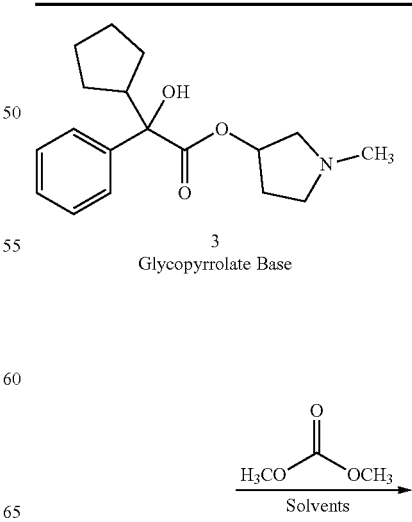

TABLE 18-continued

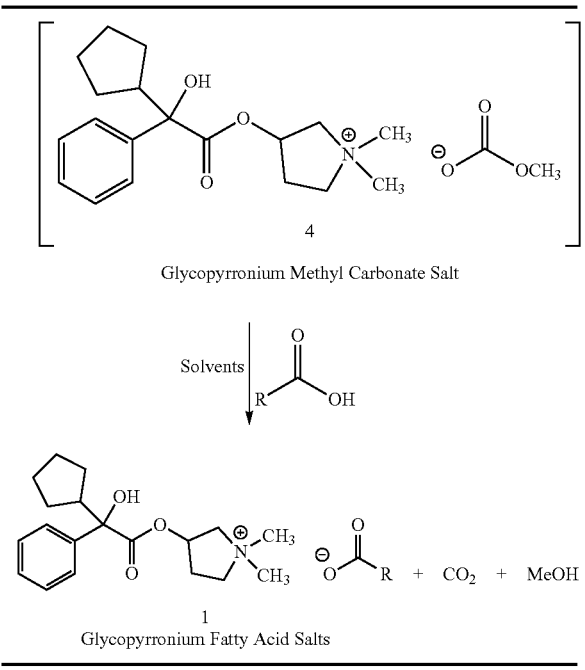

Glycopyrronium Fatty Acid Salts

In all four experiments (see FIG. 5), the glycopyrrolate base 3 was observed to decompose under the reaction conditions, yielding the cyclopentyl mandelic acid derivative ("Acid A") and the corresponding methyl ester (Table 5). The analytical results showed that no desired product was observed in any of the reaction mixtures.

Due to the instability of the starting glycopyrrolate base, the salt metathesis approach via the glycopyrronium methyl carbonate salt was abandoned.

Figure 6:
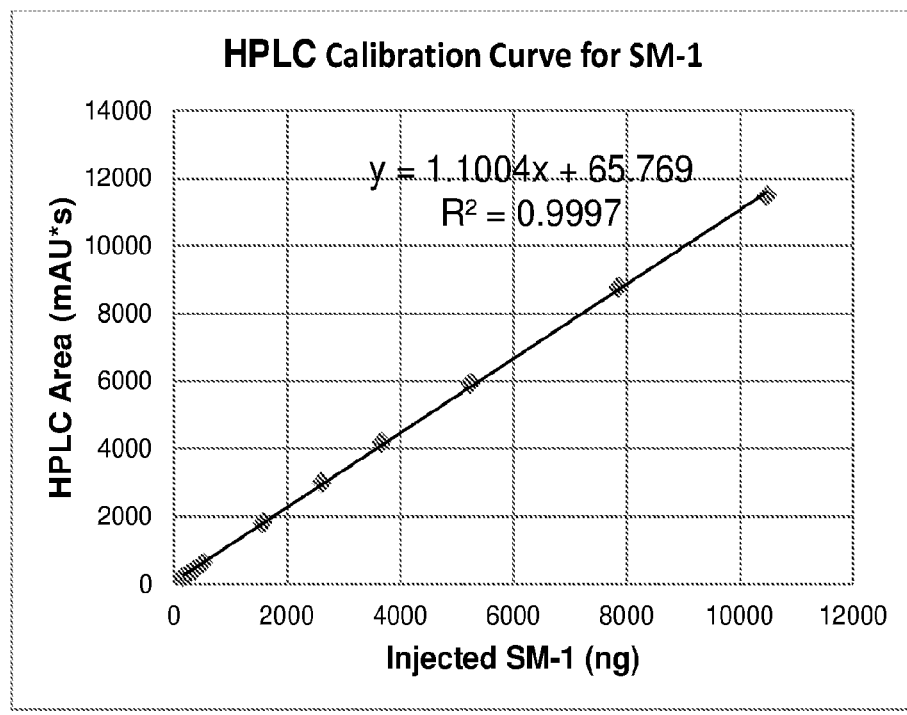
FIG. 6 shows the HPLC calibration curve for the glycopyrrolate base.

Preparation of HPLC Calibration Curves for Glycopyrrolate base and Glycopyrronium Bromide Based on analytical result reports for the raw materials, an HPLC method was set-up and three HPLC calibration curves for glycopyrrolate base (structure 3 in Table 3B) as well as glycopyrronium bromide (structure 2 in Table 3B) were prepared. These are summarized in Table 19 and FIGS. 1-2 and 6.

TABLE 19

| Column | Waters XBridge C18 |
| --- | --- |
|  | 150 × 4.6 mm; 3.5 μm |
| Flow Rate | 1.0 mL/min |
| Column Temperature | 40° C. |
| Detection Wavelength | 214 nm |
| Mobile Phase A | 0.01M of $NH_4HCO_3$ Water |
| Mobile Phase B | Acetonitrile |
| Gradient | 0 to 10 min    MP B from 5% to 100% |
|  | 10 to 15 min    MP B at 100% |
|  | 15.1 to 20 min    MP B at 5% |
| Glycopyrrolate Retention Time | ~9.5 minutes |
| Glycopyrronium bromide Retention Time[Note] | Peak #1 at ~1.5 minutes |
|  | Peak #2 at ~7.2 minutes |

Note:
Glycopyrronium bromide gave two distinct peaks in the chromatogram. Peak #1 (RRT = 0.20) corresponds to the "Bromide" ($Br^-$ ion) and Peak #2 (RRT = 1.00) corresponds to the "Glycopyrronium" moiety.

Further Synthesis and Analysis

Analytical methods were also developed for the glycopyrronium fatty acid salts. These methods appropriately and accurately assess the quality of glycopyrronium fatty acid salt samples. A more refined process for the general synthesis of glycopyrronium fatty acid salts has also been developed.

The analysis includes both improvement in the synthesis of the glycopyrronium fatty acid salts and the development of methods to analyze those salts.

The synthesis process was improved and simplified by generating the required sodium or potassium salt of the fatty acids in situ (via treatment of the fatty acids with sodium or potassium hydroxide) rather than using sodium or potassium salts of the fatty acids prepared in a separate step. Substantial efforts were expended in defining a suitable amount of excess free fatty acid that would stabilize the product by minimizing its hydrolysis, while also facilitating the extraction process by minimizing the formation of emulsions, which were quite severe in some instances. Most of the development work in this second phase of the project was done with stearic acid. Also, in addition to lauric, palmitic and stearic acid, which are all saturated fatty acids, linoleic acid (C-18 unsaturated fatty acid; with cis,cis-9,12 double bonds) was also successfully converted to a glycopyrronium salt, further demonstrating the generality of the method.

The analytical methods development addressed the challenge stemming from the nature of the components from the reaction mixture, which required the use of complementary analytical methods to assess the salt metathesis process and the quality of the product. With the methods that have been developed, the salt metathesis process can now be well monitored and the quality of the fatty acid salts obtained reliably assessed. The process that has been developed may be optimized to permit large scale production.

Some of the analytical method applications include, but are not limited to, assessment of the salt exchange effectiveness, to ensure that the reactions are pushed to >95% conversion by determining optimal number and amount of aqueous washes to remove inorganic bromide salts (byproducts), the determination of the optimal amount of excess free fatty acid (evaluating a suitable range of molar equivalents) needed to stabilize the active pharmaceutical ingredient (API) and the improvement of the isolation and purification of the reaction product (for example through precipitation with suitable solvent/antisolvent combinations) by evaluating the purity of the reaction products. In some preferred embodiments, the optimal number of aqueous washes is 3-4 washes. In other embodiments, the preferred number of washes is at least three washes.

Analytical method development also preferably includes methods for quantitation of chromophoric starting materials, products and degradants, methods for quantitation of weakly- or non-chromophoric starting materials and degradants (fatty acids and derived salts, dimethylhydroxypyrrolidinium degradants), methods for quantitation of the bromide ion in the starting material and the product, and methods for quantitation of the potassium (or sodium) ion in the product.

Glycopyrronium Fatty Acid salts (GPFA) were successfully prepared from glycopyrronium bromide and fatty acid salts utilizing a bi-phasic (organic/aqueous) system to selectively partition the inorganic salts into the aqueous phase and isolating the lipophilic organic salts (glycopyrronium fatty acid salts) from the separated organic phase. However, as discussed above, the reaction mixture was unstable to hydrolysis and also the fatty acid salts were unstable in methanol solution (transesterification by-product formation). The isolated glycopyrronium fatty acid salts (GPFA) also proved to be inherently unstable with increasing levels of the degradant, "Acid A" (CAS 427-49-6, α-cyclopentyl-α-hydroxybenzene acetic acid), forming over time. An excess of free fatty acid stabilized the reaction mixture and significantly reduced the rate of hydrolysis (limiting the formation of "Acid A"). It was also challenging to accurately quantitate all components from the reaction mixtures to assess the synthesis efficiency.

Further experiments explored the isolation of glycopyrronium fatty acid salts (GPFA) with an excess of free fatty acids to confirm improved stability of the isolated products and also to develop suitable analytical methods to characterize the isolated materials. These experiments included preparing the samples for development of analytic methods, developing analytical methods to characterize the glycopyrronium fatty acid products, defining a suitable preparatory procedure and characterization of the isolated products, and preparing a range of GPFA samples. These efforts were successful, resulting in a suitable preparatory procedure and analytical methods to analyze and characterize the isolated products.

The developed analytical methods are reliable and simple enough to be tailored to the individual glycopyrronium salts of fatty acids (with anticipated minor modification of the GC method conditions for each fatty acid utilized).

As discussed above, only one approach (counterion exchange, or salt metathesis via a selective partitioning in a biphasic aqueous/organic solvent system) proved effective in the preparation of glycopyrronium fatty acid salts. Attempted synthesis from glycopyrrolate base via quaternization with methyl carbonate at elevated temperatures and subsequent treatment of the expected quaternary methylammonium carbonate salts with fatty acids was unsuccessful due to decomposition of glycopyrrolate base under the methylation conditions. Salt exchange in organic solvents under anhydrous conditions failed due to poor solubility of the glycopyrronium bromide and the fatty acid salt in the organic solvents that were evaluated (acetone and dichloromethane). The observed hydrolytic instability of the glycopyrronium moiety precluded consideration of aqueous ion exchange with ion exchange resins.

Even with the selective bi-phasic partitioning approach, severe emulsions and poor partitioning were observed for most systems tested. Selective partitioning of bromide into the aqueous phase and glycopyrronium into the organic phase was not easily achieved. Among the solvent systems screened (2-Me-THF, MTBE, IPAc, Toluene, MIBK, and DCM), only 2-Me-THF provided adequate selectivity for the desired partitioning. Also, hydrolytic instability was noted over the course of the work-up and isolation with the formation of "Acid A" over time in both extracted solutions and isolated products. Isolated glycopyrronium fatty acid mixtures ranged in consistency from viscous oils to pastes to hard waxy solids.

The initial synthesis experiments tested lauric acid (C-12 chain), stearic acid (C-18 chain) and palmitic acid (C-15 chain). The further synthesis and analysis experiments tested stearic acid, lauric acid, palmitic acid, and linoleic acid (C-18 polyunsaturated, cis, cis-9,12-Octadecadienoic acid).

The method synthesized glycopyrronium fatty acid salts by reacting glycopyrronium bromide with a fatty acid salt in a biphasic reaction mixture and including at least a 0.2 molar equivalent of excess free fatty acid to the reaction mixture. In preferred embodiments, at least a 0.2 molar equivalent of excess free fatty acid is added to the reaction mixture to form a glycopyrronium fatty acid salt. In some preferred embodiments, between 0.2 and 1.2 molar equivalent of excess free fatty acid is added to the reaction mixture. In another preferred embodiment, at least 0.6 molar equivalent of excess free fatty acid is added to the reaction mixture. In yet another preferred embodiment, between 0.6 and 1.2 molar equivalent of excess free fatty acid is added to the mixture to form a glycopyrronium fatty acid salt. In another embodiment, approximately 1.2 molar equivalent of excess free fatty acid is added to the reaction mixture. In another embodiment, at least 1.1 molar equivalent of excess free fatty acid is added to the reaction mixture.

As described herein, excess free fatty acid is relative to the glycopyrronium bromide and fatty acid salt used. For example, for the lauric acid reaction, it is excess free lauric acid relative to the glycopyrronium bromide and potassium laurate used.

The excess free fatty acid stabilizes the reaction mixture. The larger excesses of free fatty acid (0.6-1.2 molar excess) improved the phase separations, improved stability of the organic extract solutions, and improved stability of the isolated products.

In preferred embodiments, the required sodium, potassium or calcium salt of the fatty acids is generated in-situ via treatment of the fatty acids with a metal hydroxide rather than using sodium, potassium, or calcium. In this step, a fatty acid is mixed with the metal hydroxide in the biphasic reaction mixture (preferably water and 2-methyl-tetrahydrofuran) until all solids are dissolved to form the fatty acid salt. The metal hydroxide is preferably either an alkali metal hydroxide or an alkaline earth metal hydroxide (e.g.— sodium, potassium or calcium hydroxide).

The method also preferably includes adding glycopyrronium bromide and mixing until the solids dissolve. The upper organic phase is retained, while the lower aqueous phase of the reaction mixture is removed. The upper organic phase is then washed with water. The steps of retaining the upper organic phase and removing the lower aqueous phase are preferably repeated. In preferred embodiments, these two steps are repeated at least 3 times to increase the purity of the glycopyrronium fatty acid salt. In other preferred embodiments, these two steps are repeated 3-4 times.

Vacuum distillation is preferably performed on the upper organic phase and new 2-methyl-tetrahydrofuran is added. The vacuum distillation step is preferably repeated at least once (for a total of two times), to remove trace amounts of residual water, until no distillate is observed. In preferred embodiments, a non-polar hydrocarbon solvent is added to precipitate insoluble components, which are filtered off. The filtrate is then further distilled under reduced pressure to obtain a solid. In preferred embodiments, the non-polar hydrocarbon solvent is n-heptane or a mixture of heptane isomers. In alternative embodiments, n-hexane, isooctane or petroleum ether could be used instead of heptanes.

Analytical methods were needed that would be sufficient to characterize the composition and purity of the isolated products and enable further development. No single method was suitable for all components and complementary (orthogonal) methods were required to adequately characterize the isolated products.

Development of a purity and assay method was hindered by the lack of chromophores for the fatty acid components and any 3-hydroxy-1,1-dimethyl pyrrolidinium degradants. There was also a lack of retention/separation between bromide and 3-hydroxy-1,1-dimethyl pyrrolidinium degradant by HPLC. Challenging solubility properties of the glycopyrrolate mixtures, sample precipitation, column plugging, and accelerated loss of column performance also hindered method development. Ultimately, these challenges were overcome by development of the methods described below for the characterization of the glycopyrronium fatty acid salts.

With the challenges encountered, the preparation of the target glycopyrronium fatty acid salts was not trivial and required inventiveness to achieve the preparation of stable, well characterized products suitable for further development as API products.

Methods for Preparing Glycopyrronium Fatty Acid Salts

Bi-phasic reaction conditions enable the desired exchange reactions between glycopyrronium bromide and sodium and potassium salts of fatty acids. Favorable partitioning of the glycopyrronium moiety into the organic phase (along with the fatty acids) and partitioning of the bromide into the aqueous phase was achieved with water and 2-methyl tetrahydrofuran. The glycopyrronium fatty acid salts were unstable to hydrolysis under the reaction conditions and as isolated oily products in the absence of an excess amount of free fatty acid. The formation of the impurity, "Acid A", was noted over time. An excess of the free fatty acid in the reaction mixture stabilized the glycopyrronium fatty acid salt and reduced the formation of the impurity, "Acid A". One reason for the stabilization may be an aggregation between the glycopyrronium fatty acid salt and the excess free fatty acid, with the hydrophobic fatty acid chain shielding the ester linkage and protecting it from access by water. The isolation of a well-defined product, though challenging, was achieved.

The preparatory procedure was further defined and the isolated products characterized using analytic methods. In addition, a range of glycopyrronium fatty acid samples were prepared, including glycopyrronium laurate, glycopyrronium stearate, glycopyrronium palmitate and glycopyrronium linoleate.

Initially, alkali metal fatty acid salts were prepared and isolated prior to use in preparing the glycopyrronium fatty acid mixtures. A simpler preparative procedure for the glycopyrronium fatty acid mixtures without isolation of fatty acid metal salts is preferred. Since the fatty acid metal salts, excess free fatty acid, and glycopyrronium bromide were mixed in a 2-Me-THF/water mixture, a modified procedure prepared the fatty acid metal salt in solution. The target amounts of fatty acid and metal hydroxide readily dissolved in a mixture of water and 2-Me-THF to directly provide the desired solution of fatty acid salt and excess free fatty acid.

This approach is detailed in the following example. Stearic acid (6.26 g, 22 mmol, 2.2 eq.) and potassium hydroxide (0.726 g, 11 mmol, 1.1 eq.) were dissolved in a mixture of water (50 mL) and 2-Me-THF (50 mL). The molar excess of the free stearic acid in this example was 1.2 molar equivalent of excess free stearic acid (relative to the glycopyrronium bromide) and a 1.1 molar equivalent of excess free stearic acid relative to potassium hydroxide, assuming the purity of the potassium hydroxide is 100% (which is rarely the case). Mechanical stirring provided complete dissolution over approximately 30 minutes. Without stirring, the mixture settled into two clear phases with little to no emulsion remaining after approximately 30 minutes. Glycopyrronium bromide (3.98 g, 10 mmol, 1.0 eq.) was added, mixed, and dissolved (immediate complete dissolution). The mixing was stopped and phase separation was complete in less than 30 minutes. The lower aqueous phase (pH=7) was removed and the upper organic phase was washed three times with 20 mL of water. Each phase separation required less than 1 hour. After removing the last water wash, the rich organic phase was vacuum concentrated to mushy paste at 20-25° C./25-30 Torr. 2-Me-THF (30 mL) was added and the vacuum concentration was repeated. Heptane (50 mL) was added resulting in a thin slurry. Dissolution in heptane confirmed the lipophilic nature of the glycopyrronium stearate since both glycopyrronium bromide and potassium stearate are insoluble in heptane. When the heptane solution was chilled in an ice bath, a thick slurry formed but this became a thin slurry on re-warming to ambient temperature. After cooling in an ice bath for approximately 30 minutes, the chilled slurry was filtered on a glass-frit funnel but filtration was very slow and the contents warmed to room temperature during filtration. The isolated solids, confirmed to be stearic acid, were sucked dry under a nitrogen blanket and the dried solids weighed 0.9 g. The filtrate was vacuum concentrated at 20-25° C./25-30 Torr to an oily paste. The filtrate was confirmed to be glycopyrronium stearate and excess free stearic acid.

These samples were utilized for analytical method development. During the course of the analytical method development, it was observed that the glycopyrronium stearate sample (EE-008-001-3B) was significantly more stable than prior samples prepared during the initial feasibility work phase (much slower rate of "Acid A" formation). However, the sample was still observed to slowly degrade over time, and by the time the method development was completed (~4 months), and the sample was analyzed with the final methods, formation of "Acid A" was noted (2.44% w/w, 9.29% AUC HPLC Acid A relative to glycopyrronium content).

Further experiments tested variations on the excess of free stearic acid used to prepare the glycopyrronium stearate. These experiments used the same general procedure as discussed in the glycopyrronium stearate example (EE-008-001-3B) above. More specifically, different molar equivalents of stearic acid were tested, from 1.2 to 2.0 molar equivalents (from 0.2 to 1.0 excess molar equivalents), in 0.2 molar equivalent increments. The different variations of free fatty acid excess tested are shown in Table 20. Samples were waxy solids from Methyl-THF/GPBr/Stearic Acid/Potassium Stearate mixtures after three water washes.

TABLE 20

| Sample ID | Description |
| --- | --- |
| EE-008-004-A | From 1.0 eq. GPBr, 1.1 eq. KOH, 1.2 eq. Stearic Acid |
| EE-008-004-B | From 1.0 eq. GPBr, 1.1 eq. KOH, 1.4 eq. Stearic Acid |
| EE-008-004-C | From 1.0 eq. GPBr, 1.1 eq. KOH, 1.6 eq. Stearic Acid |
| EE-008-004-D | From 1.0 eq. GPBr, 1.1 eq. KOH, 1.8 eq. Stearic Acid |
| EE-008-004-E | From 1.0 eq. GPBr, 1.1 eq. KOH, 2.0 eq. Stearic Acid |

Samples A and B had difficult (very slow) phase splits for the water washes after the initial phase split of the reaction mixture. In contrast, all phase splits for samples C, D, and E were done within approximately 1 hour. In contrast to the earlier preparation of EE-008-001-3B, with 2.2 molar equivalent of stearic acid, no filterable solids were observed from the final heptane dissolution; only some separation of an oily phase was noted and this was retained during isolation. The samples were analyzed and the results of the comparative analysis from variable fatty acid input are summarized in Table 21. Sample EE-008-001-3B was included for comparison.

TABLE 21

| Sample ID | Stearic Acid Input | Wt. % K+ | Wt. % Br− | Wt % GP | Wt. % Stearate | Wt. % Other | GP HPLC AUC | Molar ratio Stearate/GP |
|---|---|---|---|---|---|---|---|---|
| EE-008-004-A | 1.2 eq | 0.24 | 0.036 | 32.53 | 49.42 | 18.05 | 82.8% | 1.7 |
| EE-008-004-B | 1.4 eq | 0.27 | 0.058 | 21.82 | 5.85 | 72.33 | 96.4% | 0.3 |
| EE-008-004-C | 1.6 eq | 0.25 | 0.020 | 24.16 | 10.1 | 65.73 | 98.0% | 0.47 |
| EE-008-004-D | 1.8 eq | 0.32 | 0.006 | 34.65 | 32.78 | 32.57 | 96.1% | 1.05 |
| EE-008-004-E | 2.0 eq | 0.28 | 0.006 | 29.30 | 24.29 | 46.41 | 97.1% | 0.93 |
| EE-008-001-3B | 2.2 eq | <0.1 | <0.1 | 38.39 | 51.45 | 10.16 | 94.3% | 1.5 |

While an effective purge of bromide was demonstrated and residual potassium was low, there was no clear trend in the results for glycopyrronium or stearate content across the samples. Since using less than 2.2 molar equivalent of stearic acid (relative to glycopyrronium) showed no advantage, the next experiment repeated the conditions of EE-008-001-3B (2.2 eq. stearic acid).

The sample that resulted from the repeat preparation of glycopyrronium stearate using 2.2 eq. stearic acid, EE-008-008, was analyzed and compared to EE-008-001-3B. The results are shown in Table 22.

TABLE 22

|  | Sample EE-008-008 (new) | Sample EE-008-001-3B (retest) |
|---|---|---|
| GP % w/w HPLC | 31.4% | 31.7% |
| GP % AUC Purity | 95.89% | 87.33% |
| "Acid A" % w/w | 0.13% | 2.44% |
| "Acid A" AUC % | 0.50% | 9.29% |
| Stearic Acid w/w % GC | 74.1% | 67.6% |
| Potassium w/w % IC | 1.40% | 0.60% |
| Bromide w/w % IC | 0.008% | 0.002% |
| GP/Stearate molar ratio NMR | 1:2.35 | — |
| GP w/w % by H1NMR | 32.2% | — |
| Stearate w/w % by H1NMR | 67.7% | — |

While the level of the degradant "Acid A" was typically low in the freshly isolated product, this impurity increased over time (approximately 4 months) at ambient conditions.

For EE-008-008, the input was 3.98 g (10 mmol) glycopyrronium bromide (with 22 mmol stearic Acid and 11 mmol KOH). The output was a 5.35 g glycopyrronium stearate mixture. The mass recovery was 56.7%. The glycopyrronium recovery was 54.2% (by H$^1$ NMR) and 52.8% (by HPLC assay).

Figure 7:
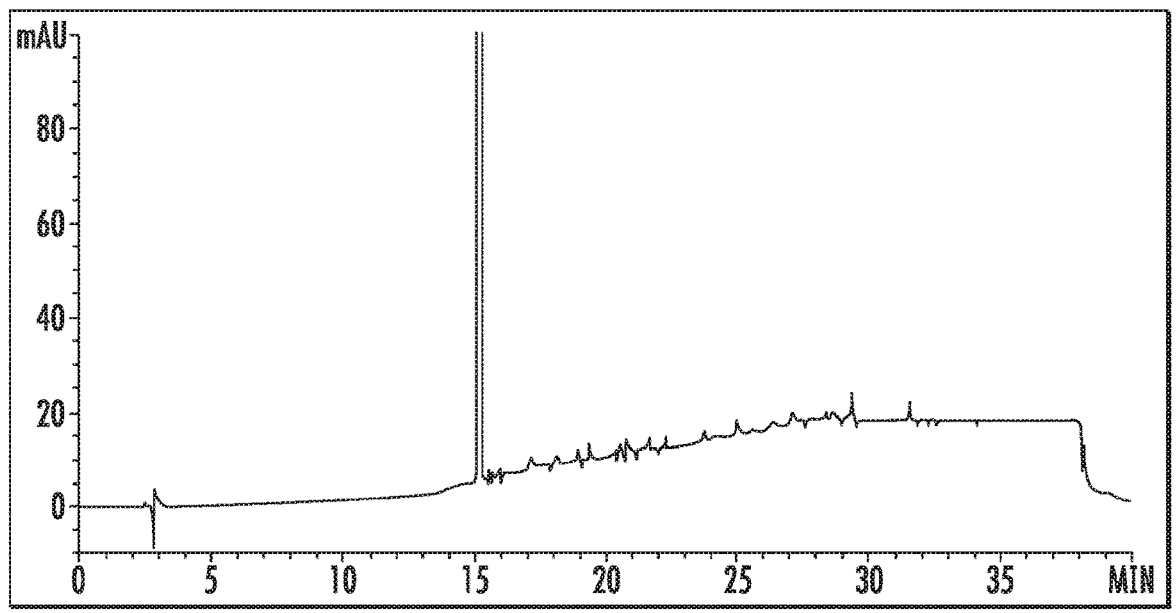
FIG. 7 shows HPLC data for glycopyrronium stearate EE-008-008.
Figure 8:
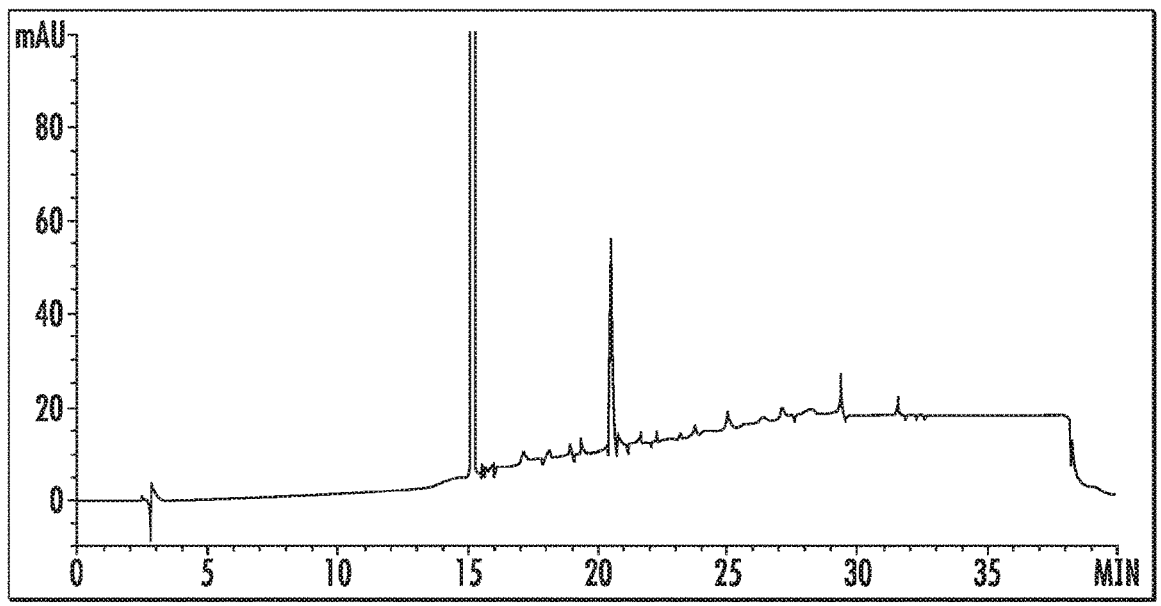
FIG. 8 shows HPLC data for glycopyrronium stearate EE-008-001-3B.

HPLC data for glycopyrronium stearate EE-008-008 is shown in FIG. 7. HPLC data for glycopyrronium stearate EE-008-001-3B is shown in FIG. 8. Peak 1, the largest peak, with 87.6482 percent area in EE-008-001-3B and 96.0360 percent area in EE-008-008, is glycopyrronium stearate. The Acid A peak occurs at approximately 17.6 minutes retention time (peak 5 in FIG. 7 and peak 8 in FIG. 8).

Figure 9:
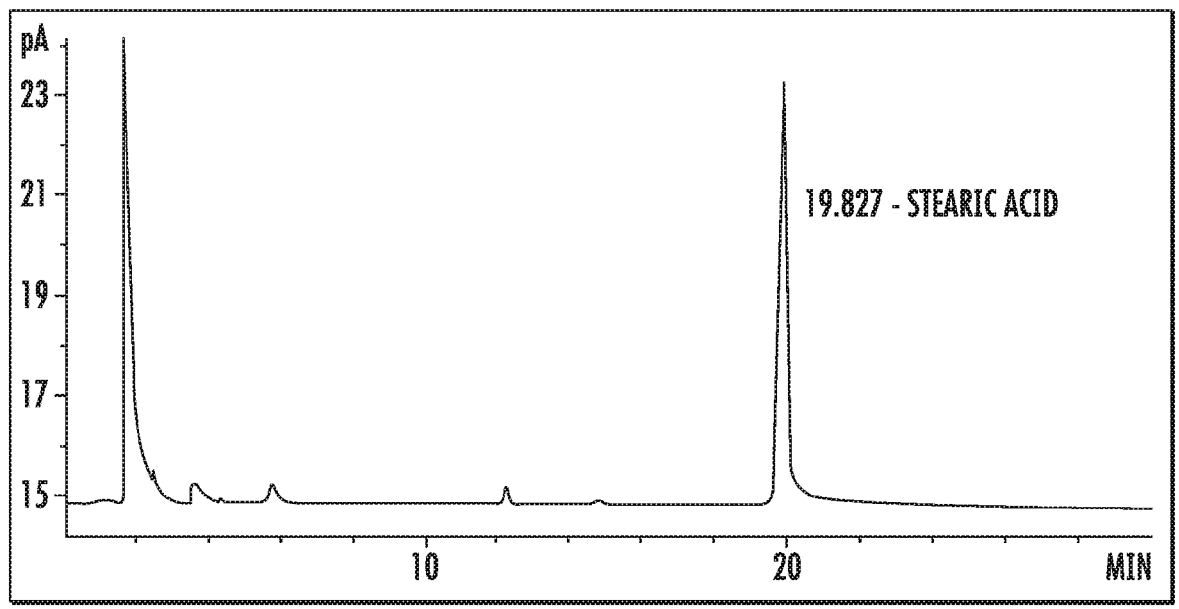
FIG. 9 shows gas chromatography data for glycopyrronium stearate sample EE-008-008.
Figure 10:
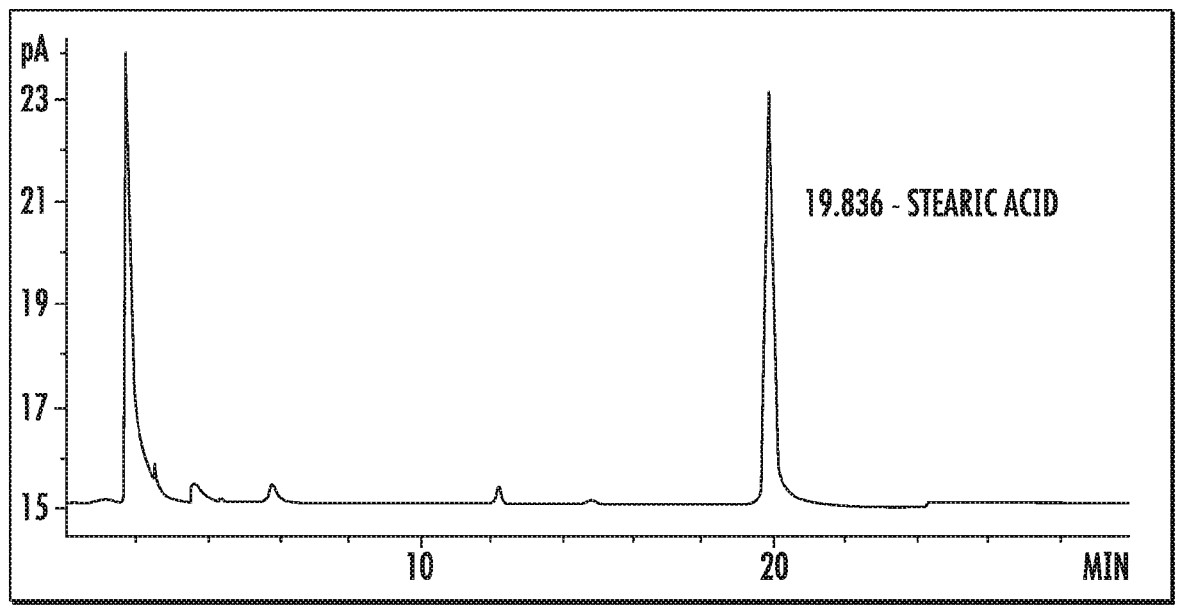
FIG. 10 shows gas chromatography data for glycopyrronium stearate sample EE-008-001-3B.
Figure 11:
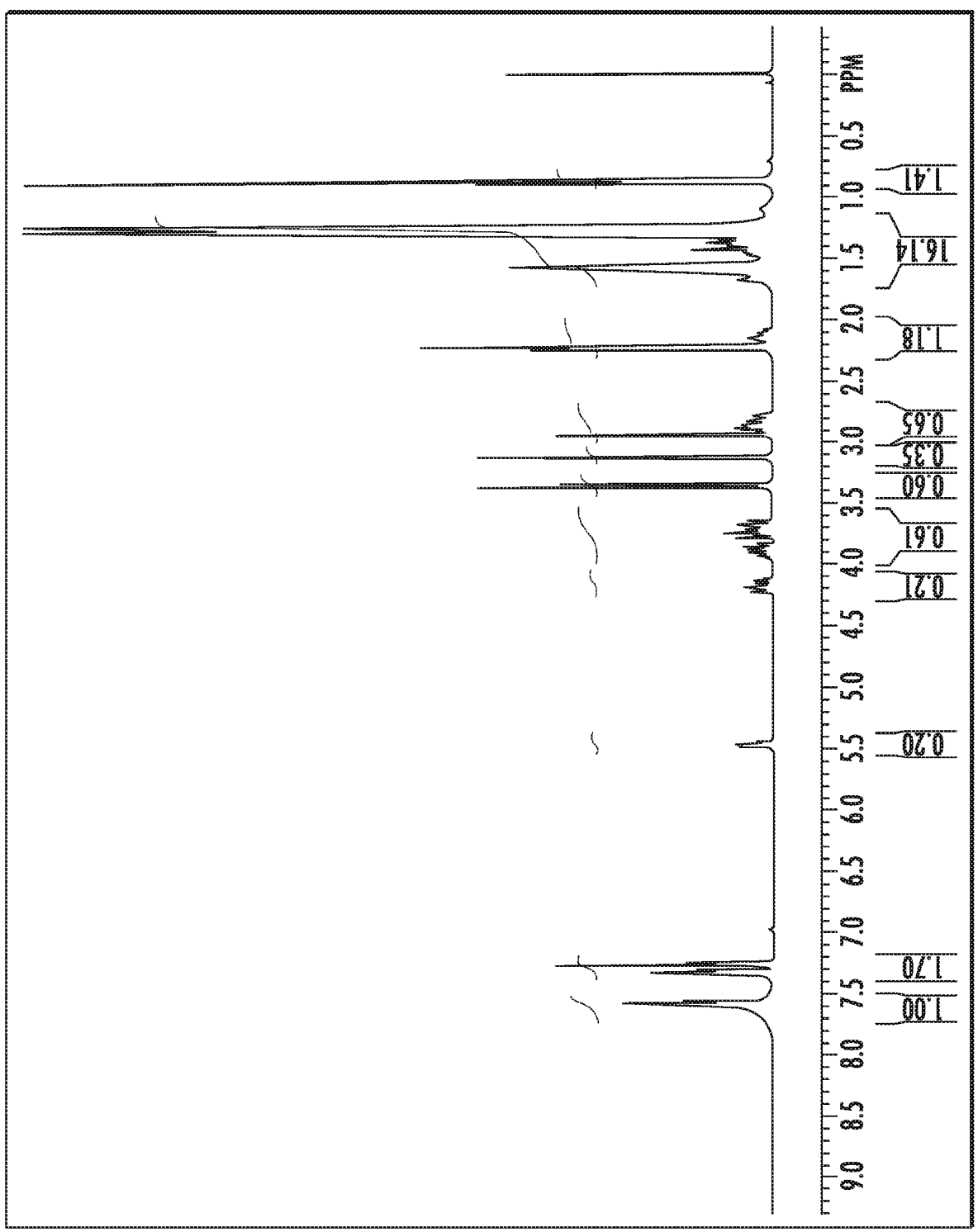
FIG. 11 shows NMR data for the whole spectrum of the glycopyrronium stearate sample EE-008-008.
Figure 12A:
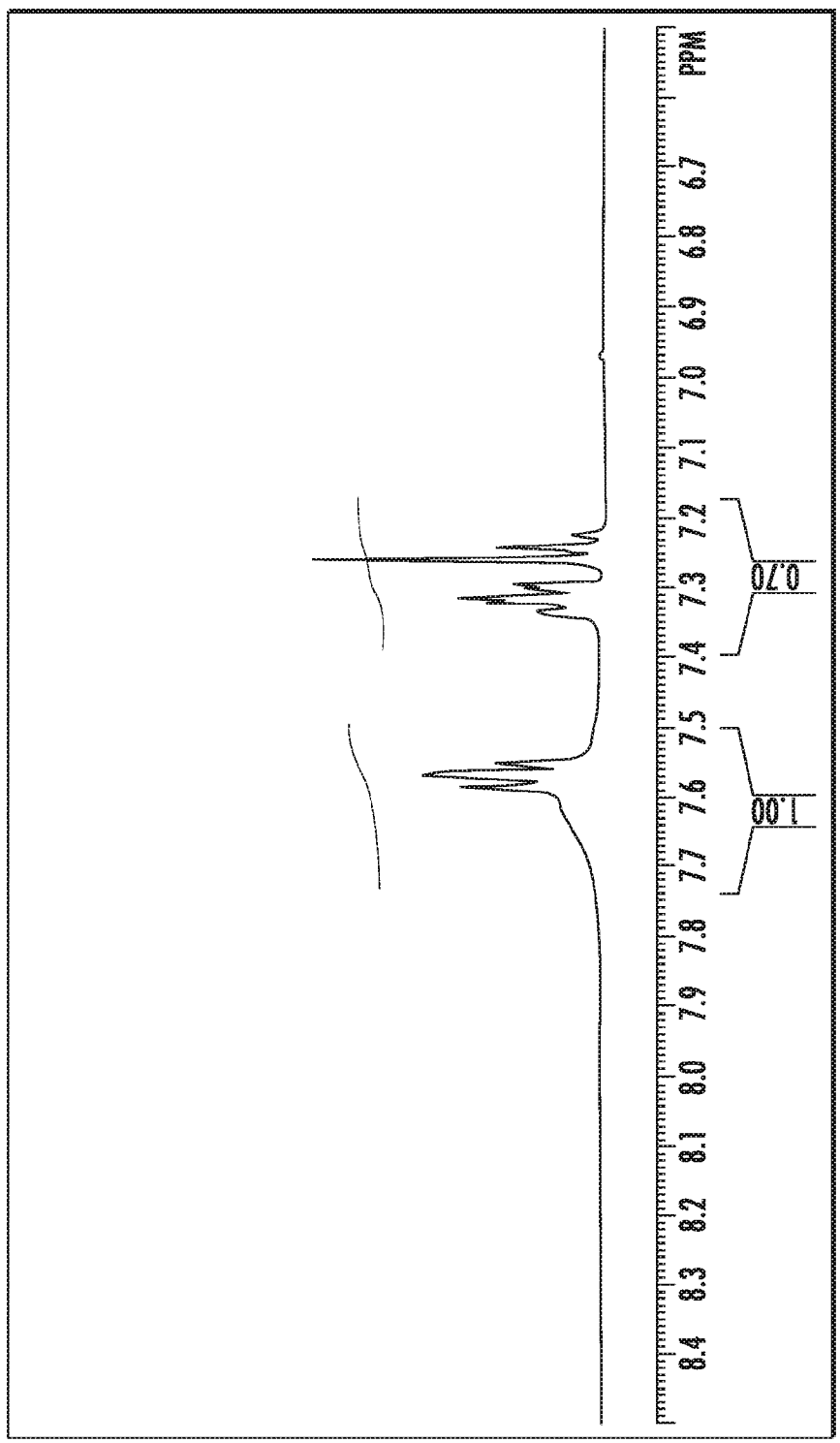
FIG. 12A shows NMR data for a portion of the spectrum of FIG. 11.
Figure 12B:
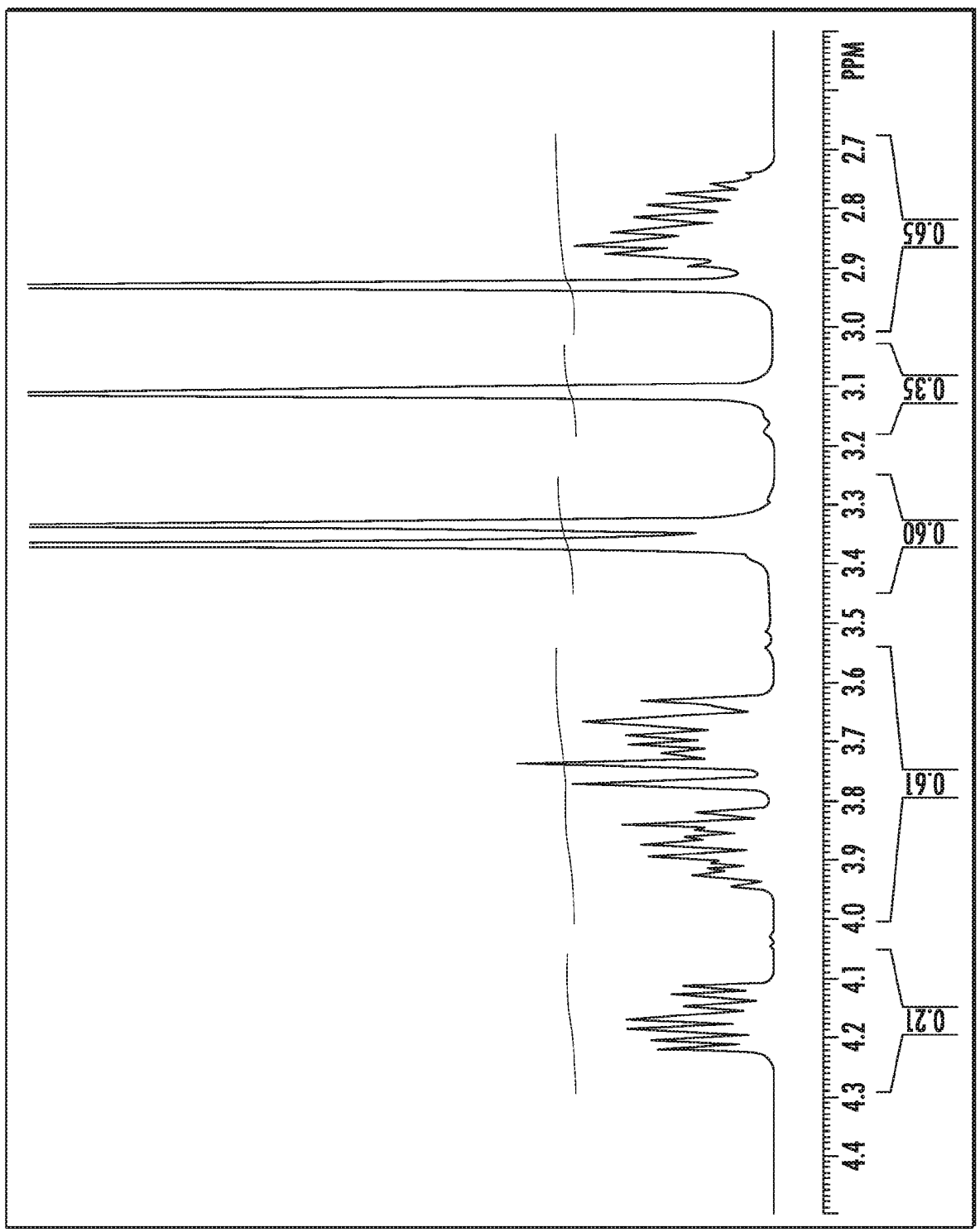
FIG. 12B shows NMR data for a portion of the spectrum of FIG. 11.
Figure 12C:
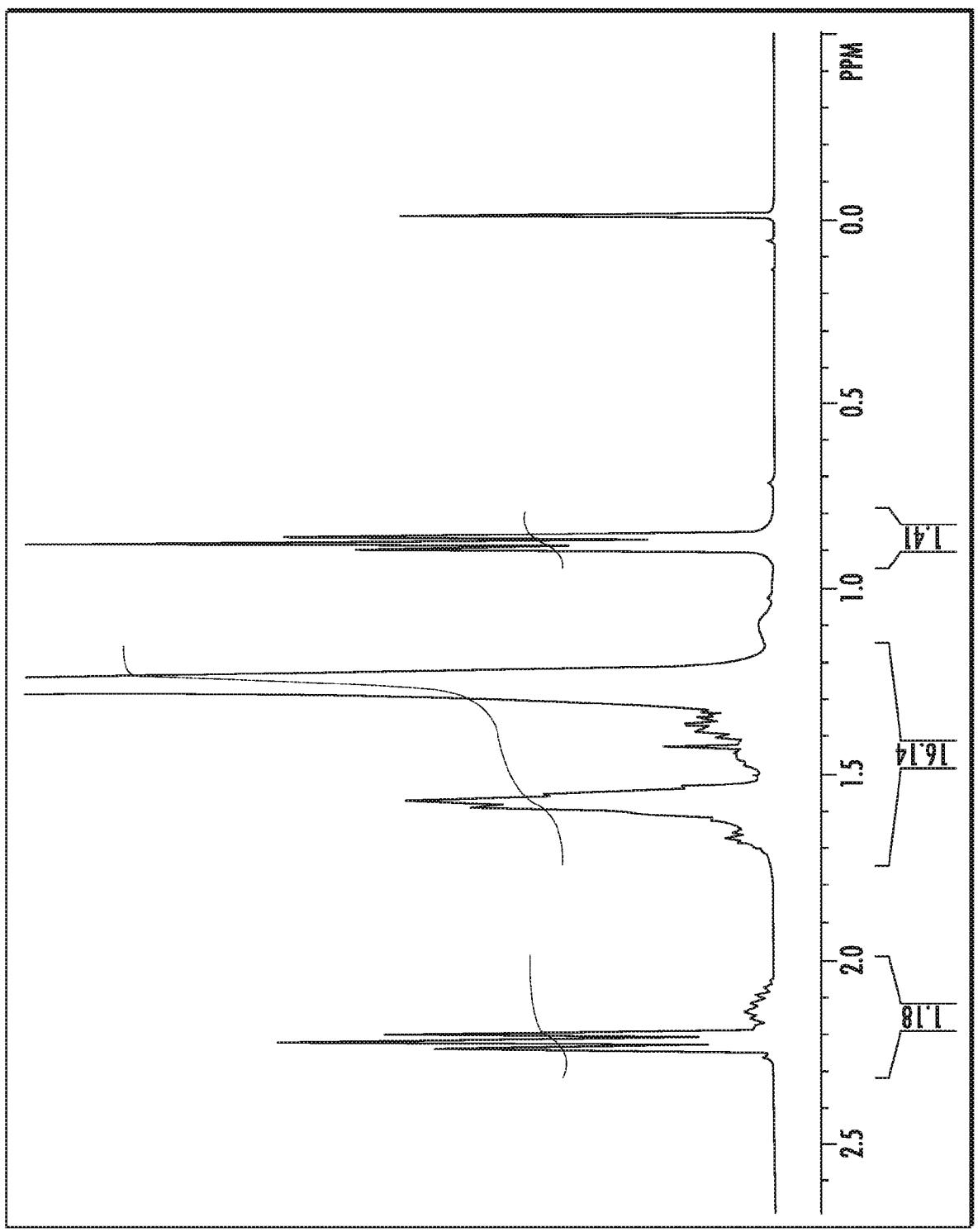
FIG. 12C shows NMR data for a portion of the spectrum of FIG. 11.

Gas chromatography data for glycopyrronium stearate sample EE-008-008 is shown in FIG. 9. Gas chromatography data for glycopyrronium stearate sample EE-008-001-3B is shown in FIG. 10. The far left peak in FIG. 9 and FIG. 10 is the solvent in the gas chromatography trace. This data shows the total amount of stearic acid (the peak at 19.827 in EE-008-008 and the peak at 19.836 in EE-008-001-3B) in the samples. The total amount of stearic acid includes the stearic acid in the glycopyrronium stearate, as well as any excess free stearic acid still present in the sample. The amount of excess free stearic acid can be calculated by determining how much stearic acid has been incorporated into the glycopyrronium stearate stoichiometrically.

All NMR chemical shifts are provided in ppm relative to tetramethylsilane (TMS). NMR data for glycopyrronium stearate sample EE-008-008 is shown in FIG. 11 and FIGS. 12A-12C. $^1$H NMR (400 MHz, CDCl$_3$) 0.88 (3H, t, CH$_3$—), 1.20-1.70 (30H, m, 15 —CH$_2$ groups from fatty acid chain and 8H, m, 4 —CH$_2$ groups from cyclopentyl ring), 2.0-2.25 (1H, m, —CH—C—N$^+$), 2.24 (2H, t, —CH$_2$C═O), 2.7-2.9 (1H, m, —CH—C—N$^+$ and 1H, m, CH group from cyclopentyl group), 2.93, 3.11, 3.33, 3.37 (6H, 4 sets of singlets, 2 —CH$_3$—N$^+$; chemical shift differences at the charged interface possibly due to different aggregation states of the fatty acid salt), 3.6-3.8 (2H, m, —CH$_2$—N$^+$), 3.8-4.0 (1H, m, —CH—N$^+$), 4.1-4.3 (1H, m, —CH—N$^+$), 5.40-5.55 (1H, m, —CH—OH, methine proton), 7.2-7.7 (5H, m, aromatic protons/phenyl group).

Figure 13A:
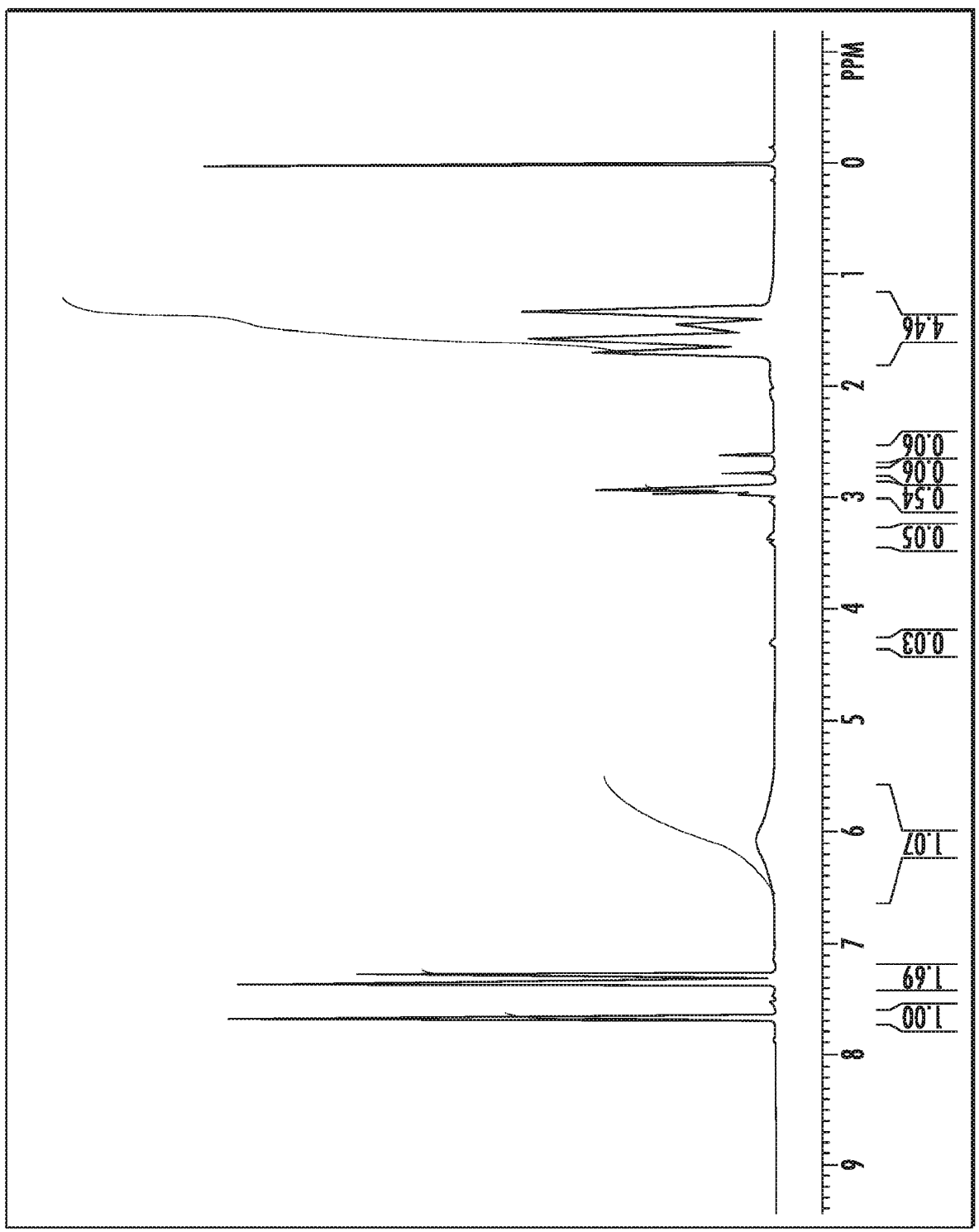
FIG. 13A shows NMR data for the whole spectrum of the Acid A by-product.
Figure 13B:
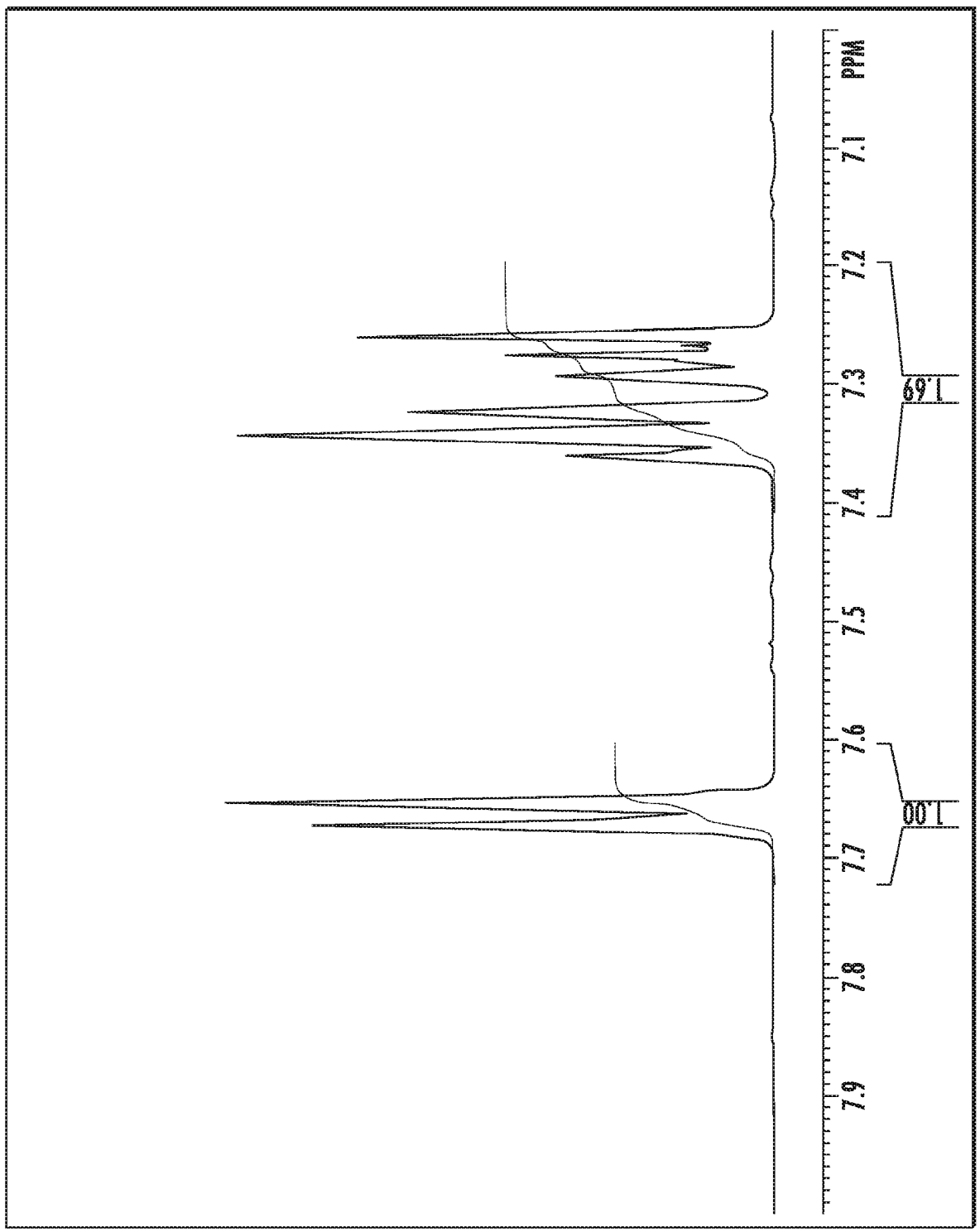
FIG. 13B shows NMR data for a portion of the spectrum of FIG. 13A.
Figure 13C:
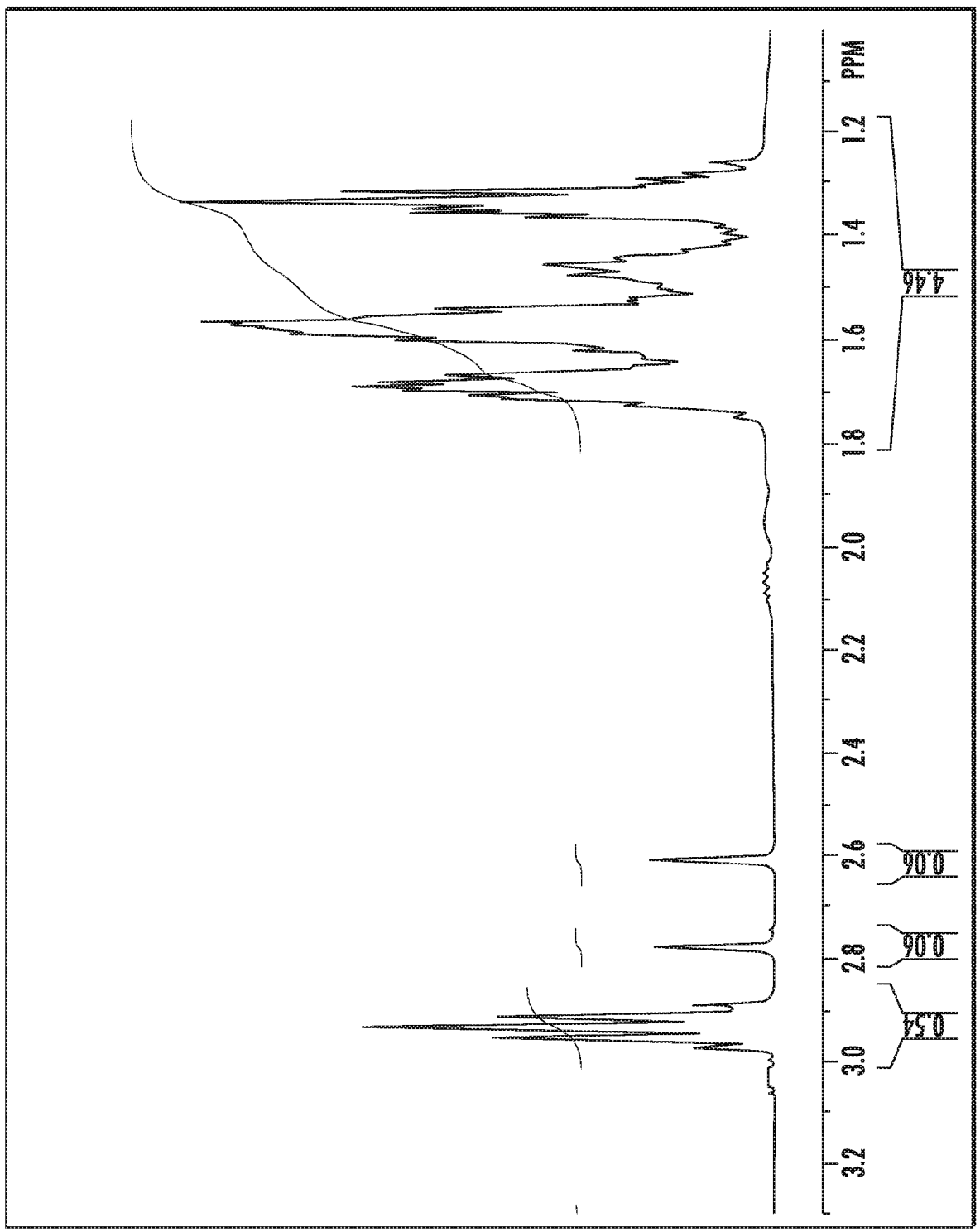
FIG. 13C shows NMR data for a portion of the spectrum of FIG. 13A.
Figure 14A:
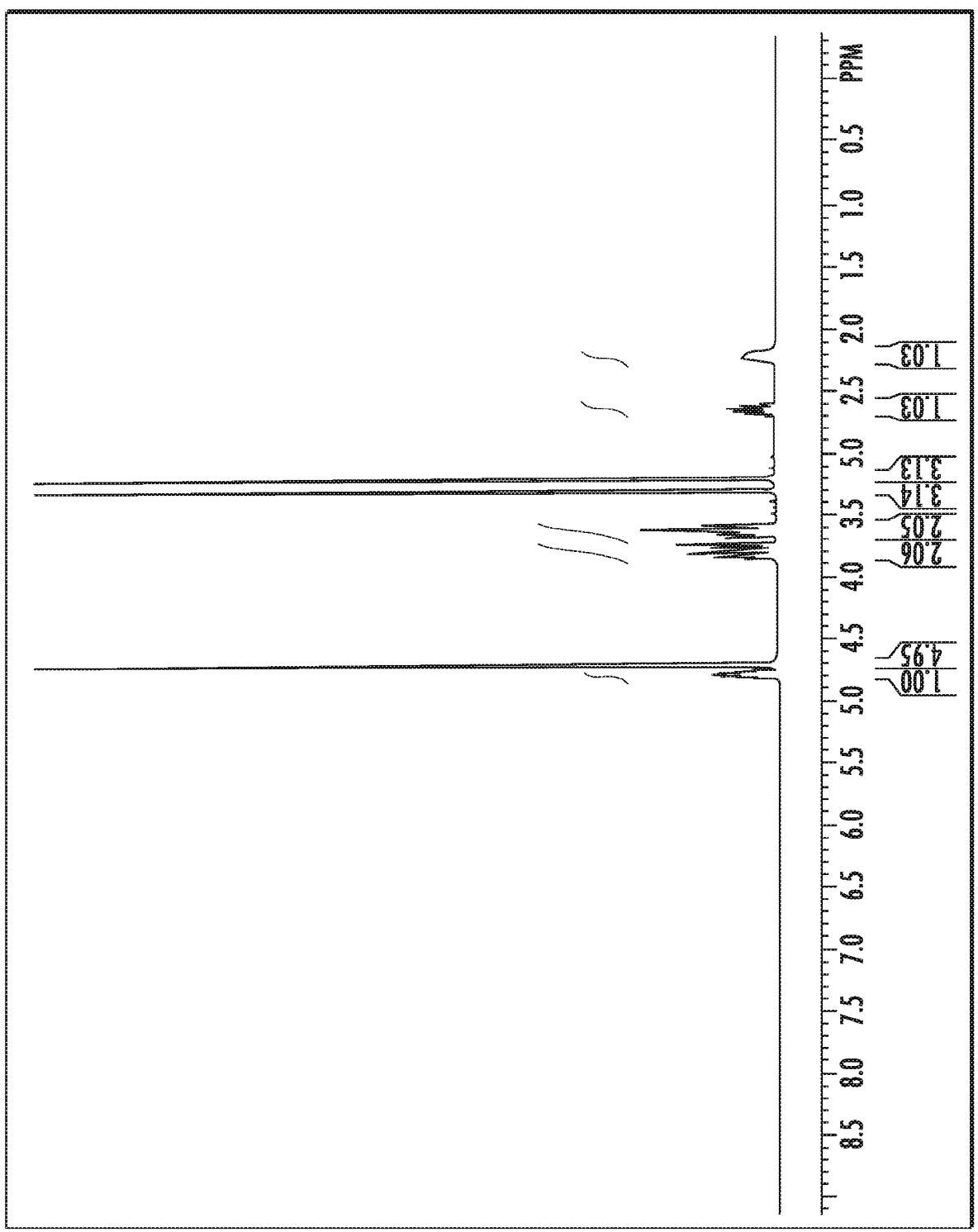
FIG. 14A shows NMR data for the glycopyrronium hydrolysis by-product, quaternary amino alcohol (QAA), residual water in DMSO-d6, s at 4.7 ppm.
Figure 14B:
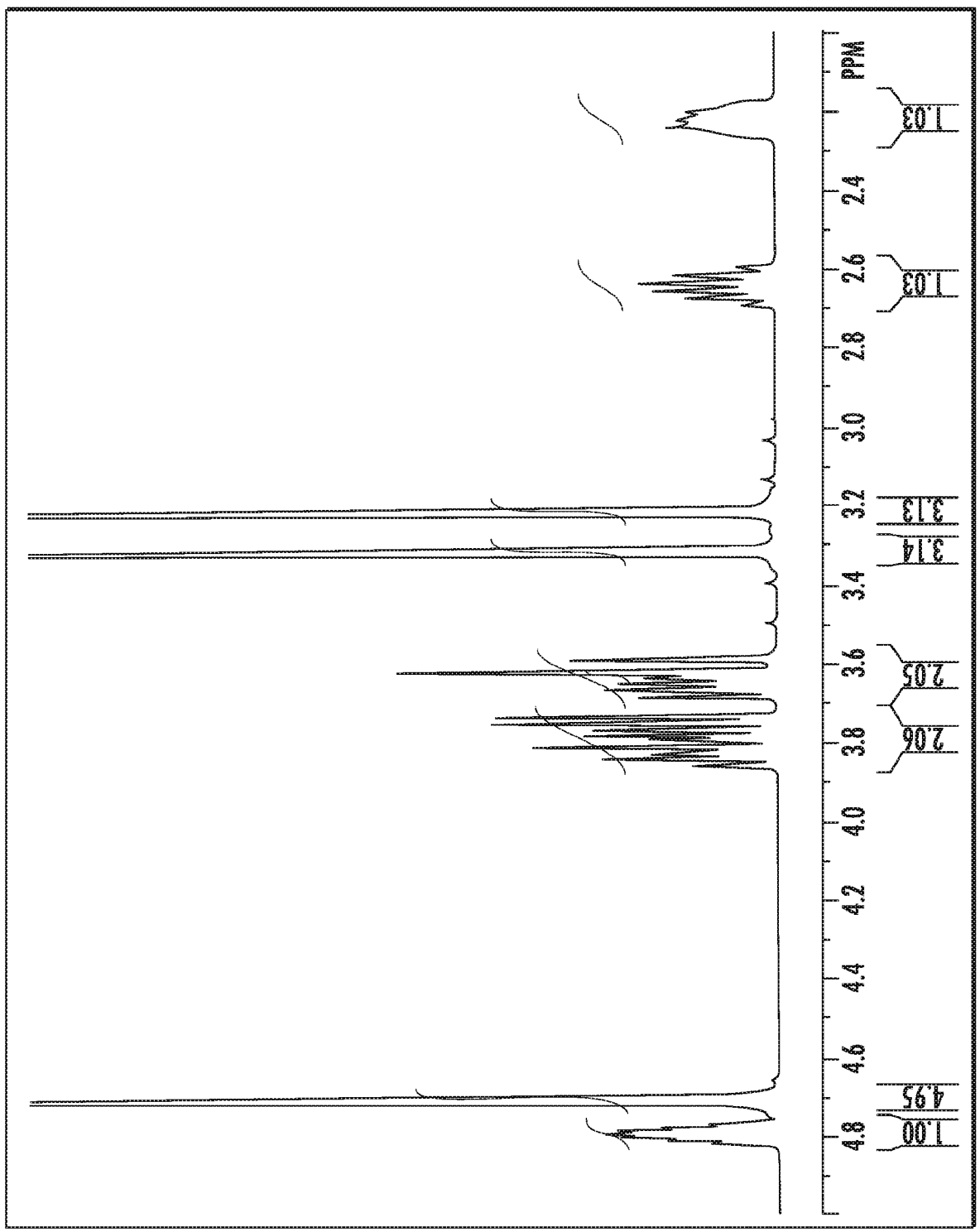
FIG. 14B shows NMR data for a portion of the spectrum of 14A.
Figure 14C:
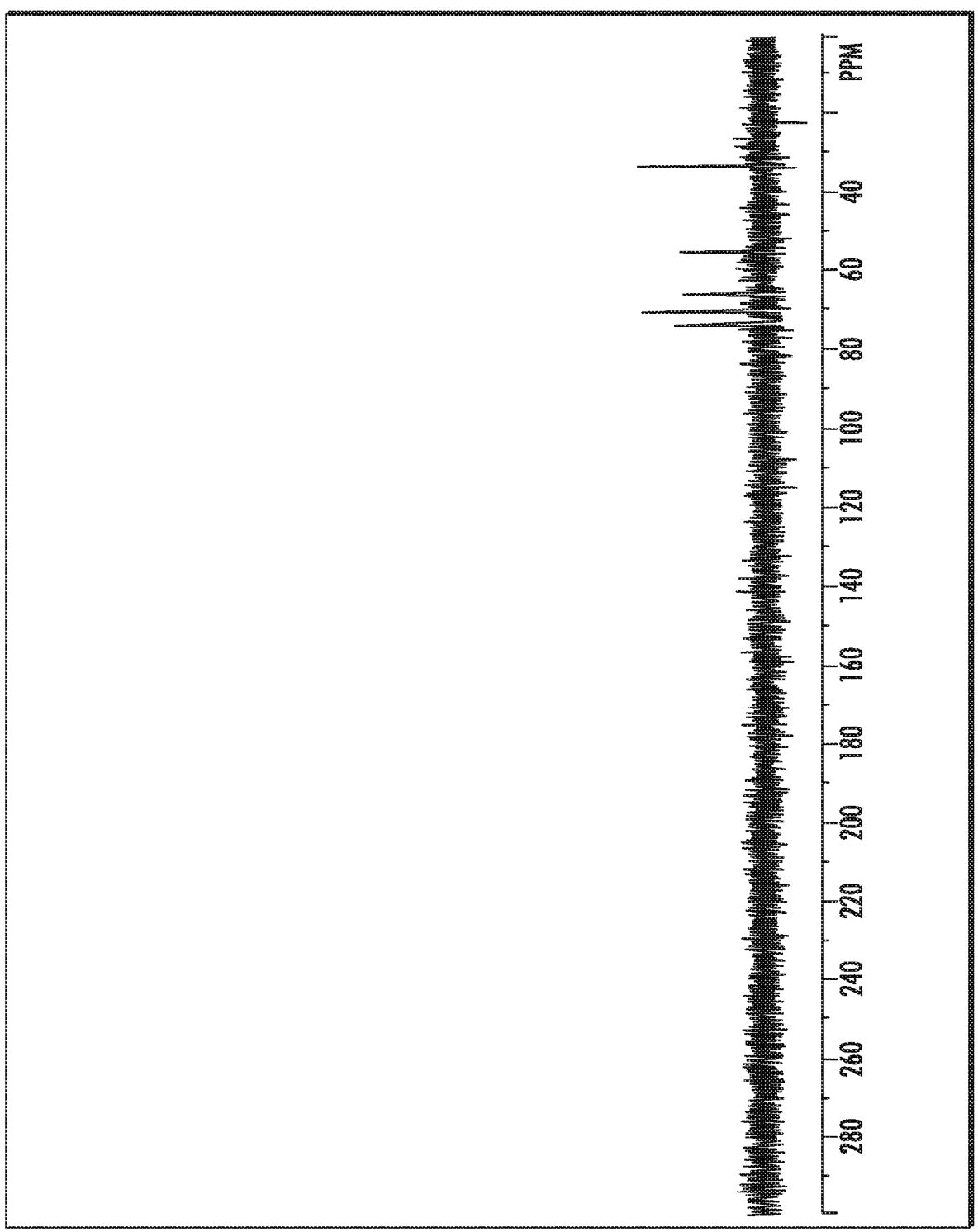
FIG. 14C shows carbon NMR data for the quaternary amino alcohol.
Figure 14D:
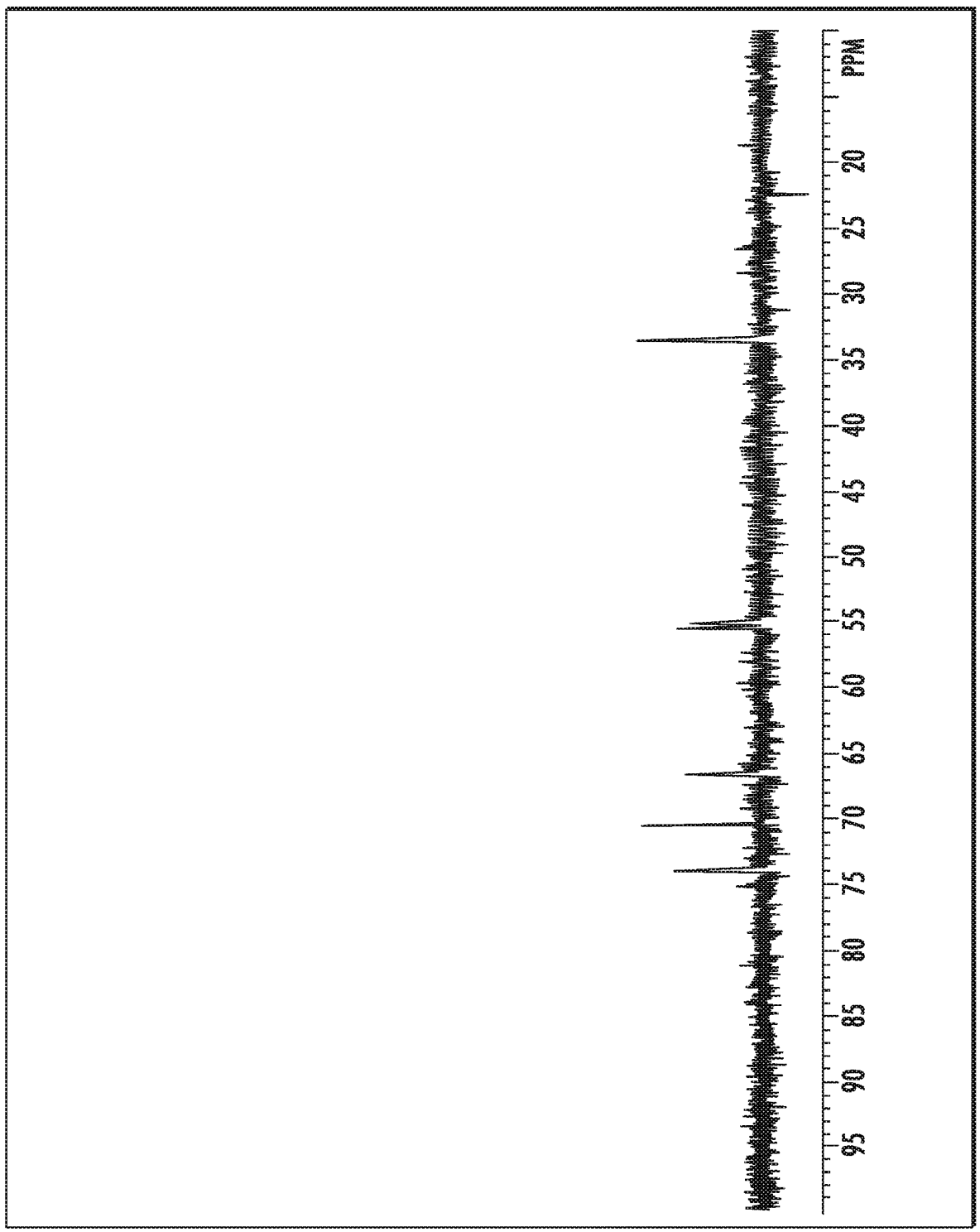
FIG. 14D shows carbon NMR data for a portion of the spectrum of FIG. 14C.
Figure 15A:
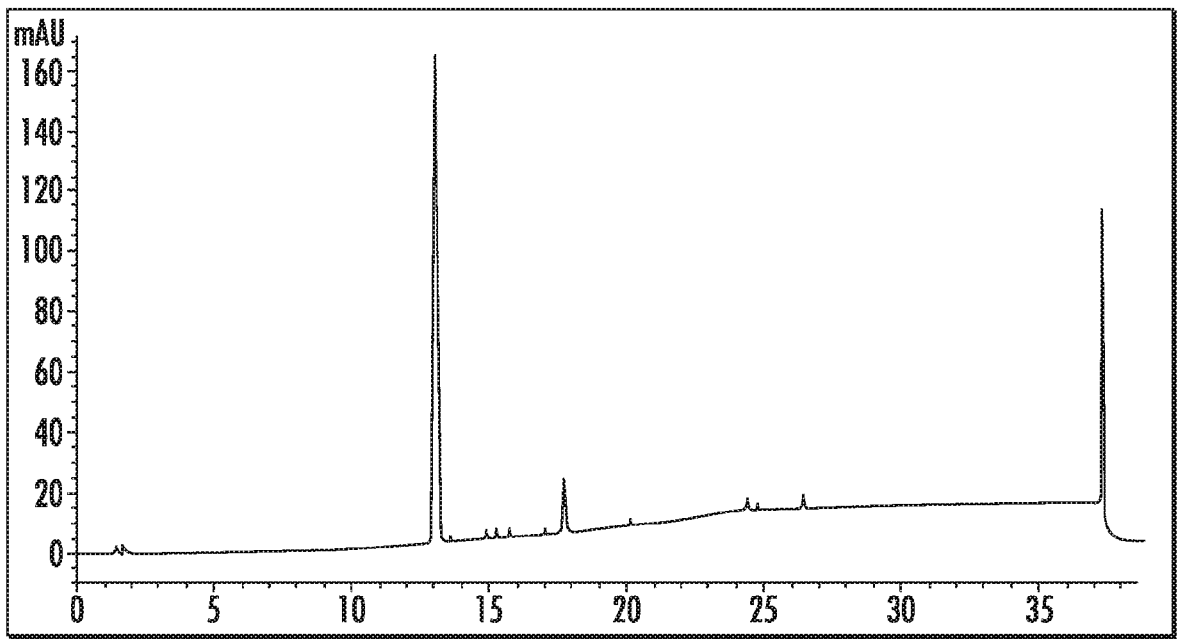
FIG. 15A shows HPLC data for glycopyrronium laurate.
Figure 15C:
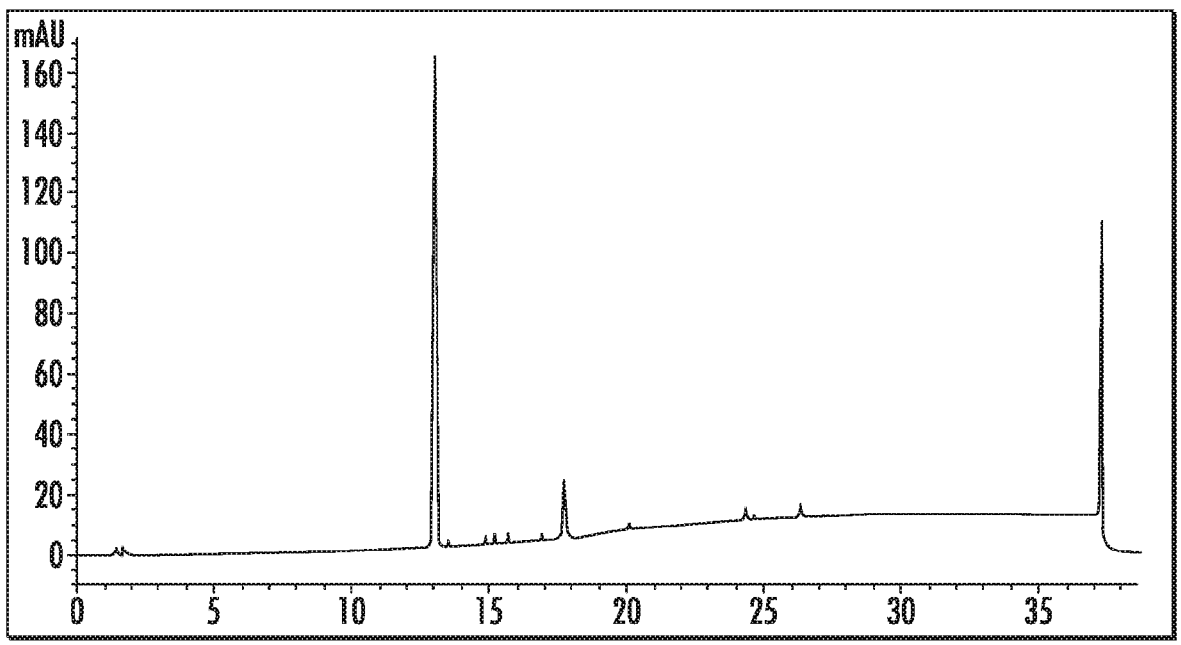
FIG. 15C shows HPLC data for another run of the glycopyrronium laurate sample.
Figure 15B:
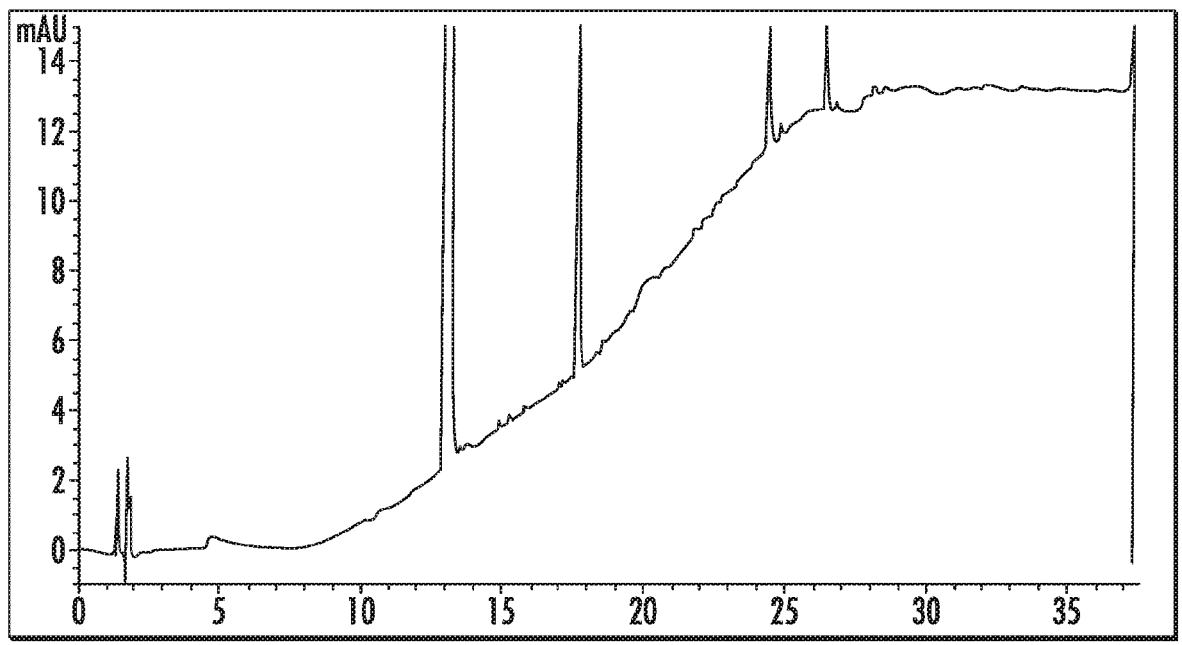
FIG. 15B shows an expanded view of the data of FIG. 15A, along with the area percent report.
Figure 15D:
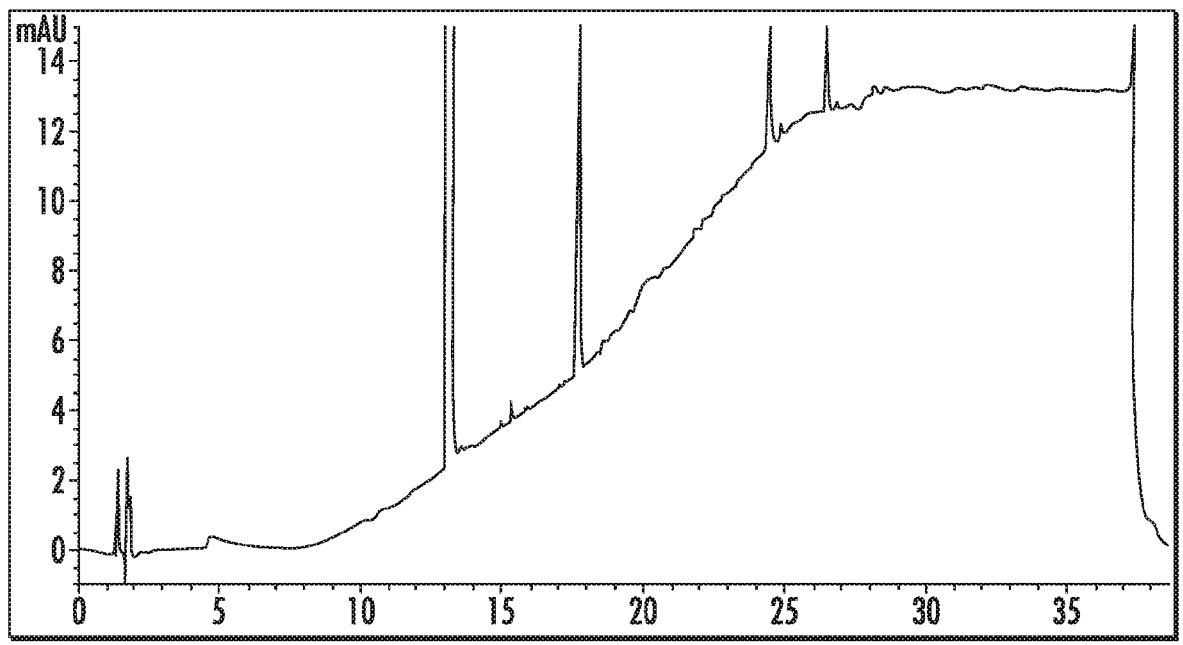
FIG. 15D shows an expanded view of the data of FIG. 15C, along with the area percent report.
Figure 16A:
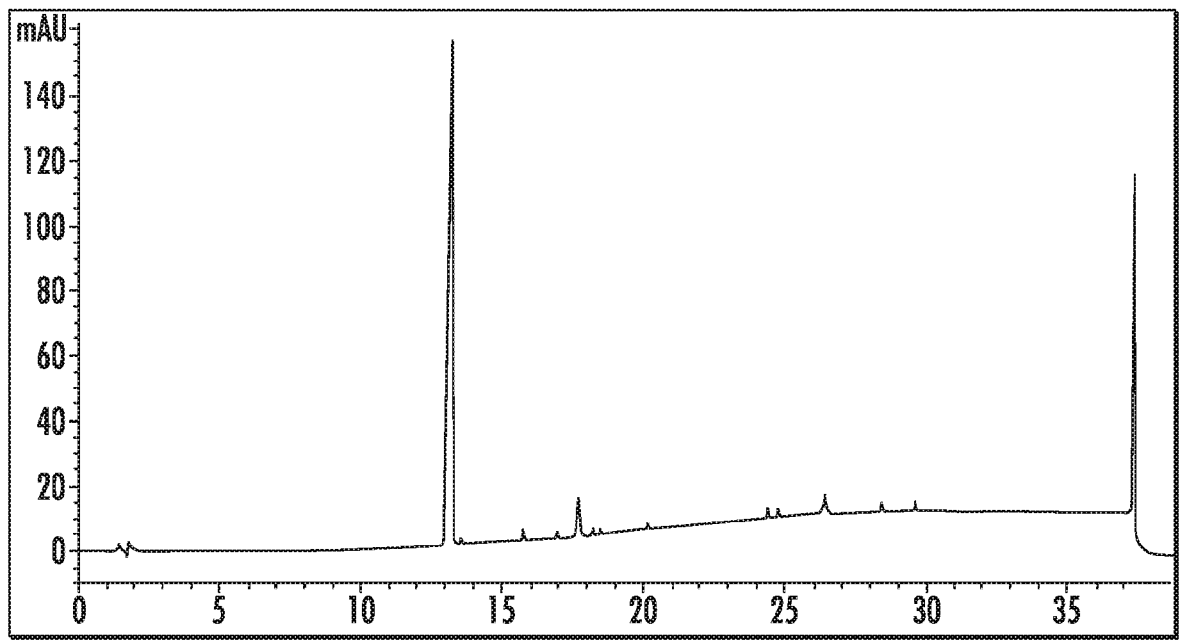
FIG. 16A shows HPLC data for glycopyrronium palmitate.
Figure 16C:
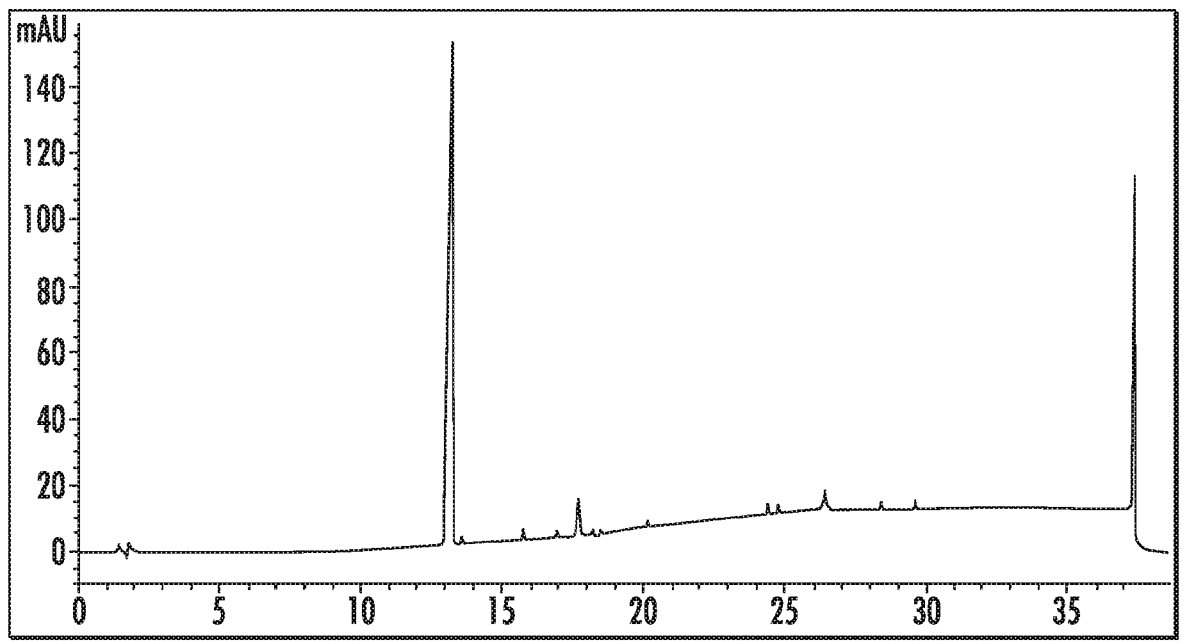
FIG. 16C shows HPLC data for another run of the glycopyrronium palmitate sample.
Figure 16B:
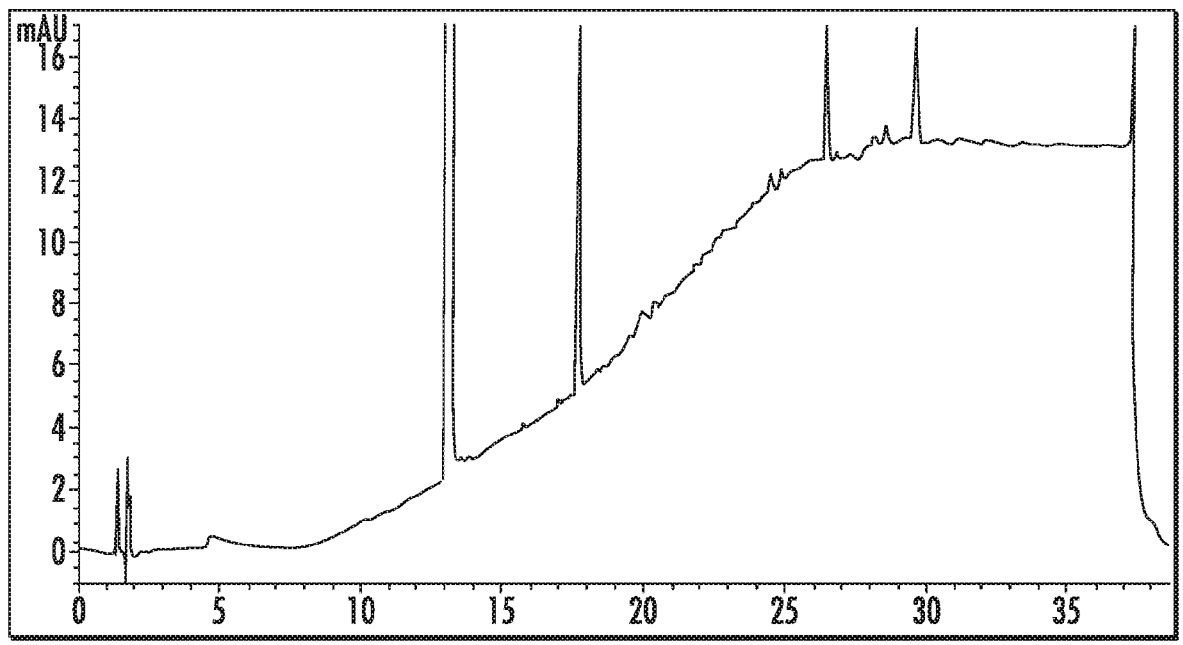
FIG. 16B shows an expanded view of the data of FIG. 16A, along with the area percent report.
Figure 16D:
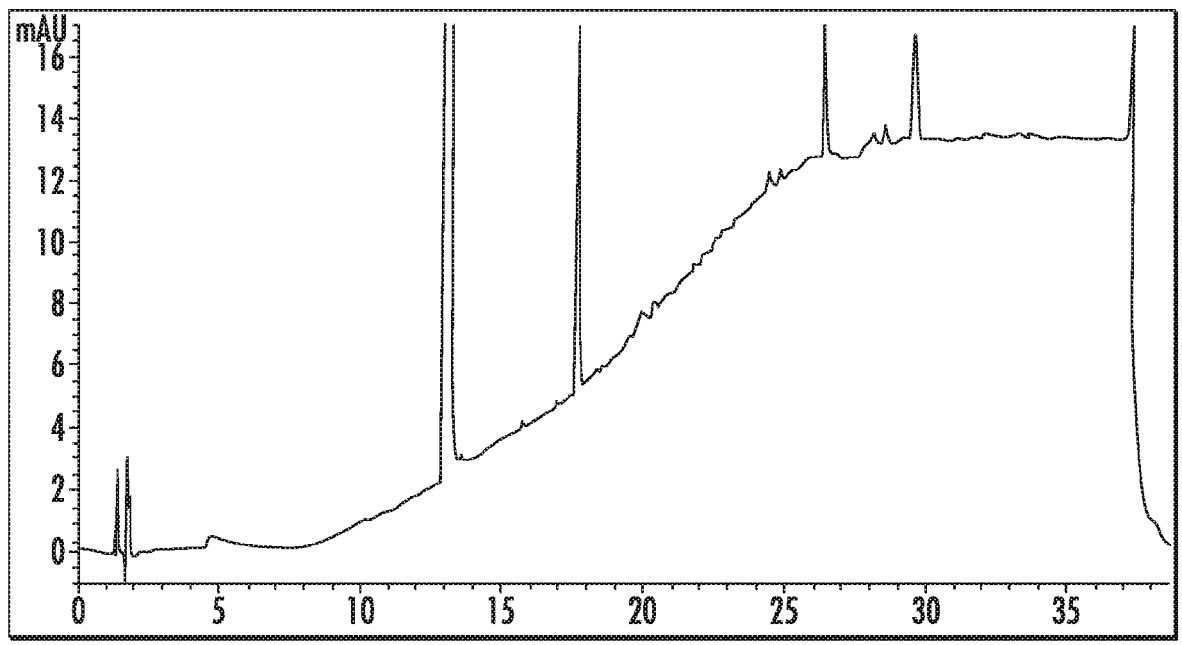
FIG. 16D shows an expanded view of the data of FIG. 16C, along with the area percent report.
Figure 17A:
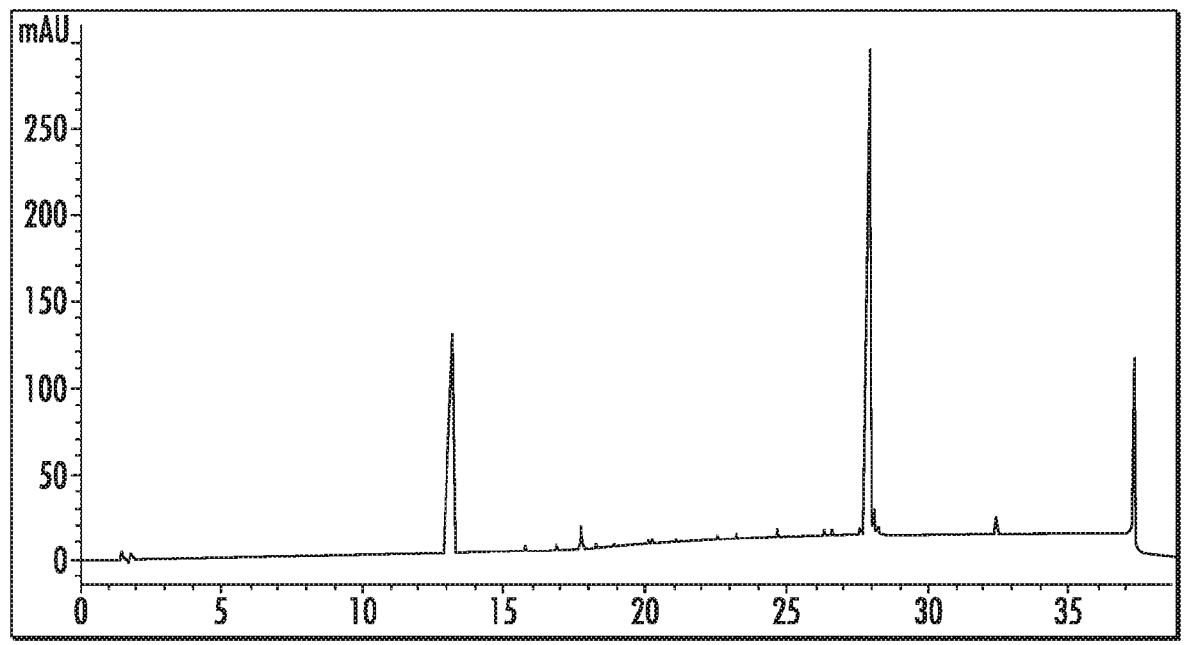
FIG. 17A shows HPLC data for glycopyrronium linoleate.
Figure 17C:
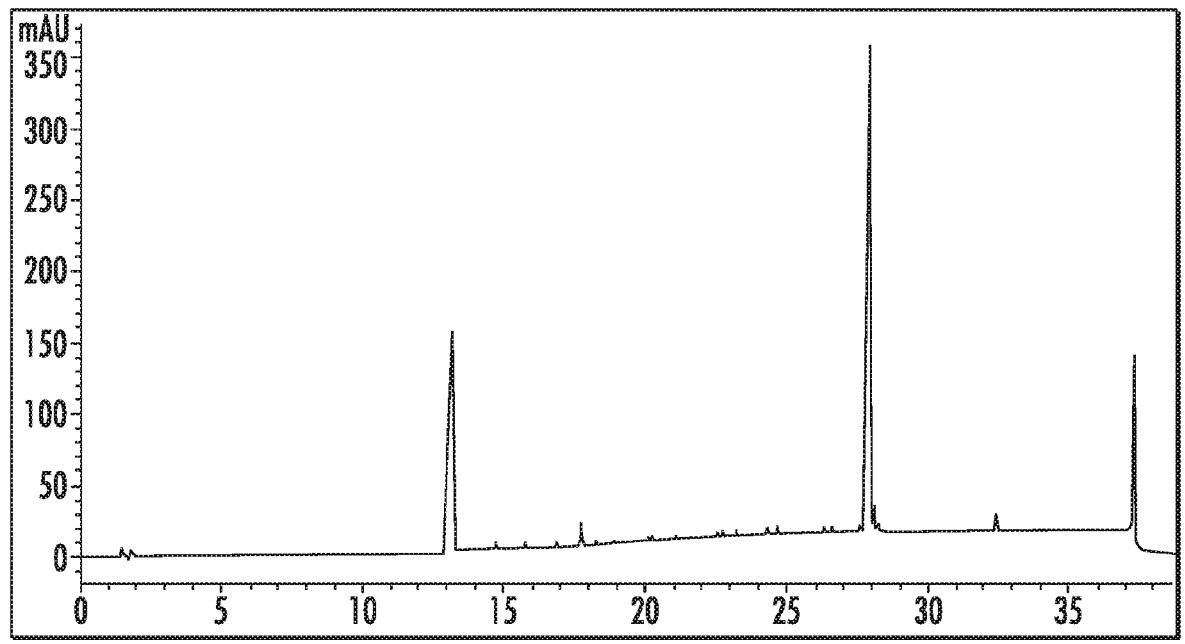
FIG. 17C shows HPLC data for another run of the glycopyrronium linoleate sample.
Figure 17B:
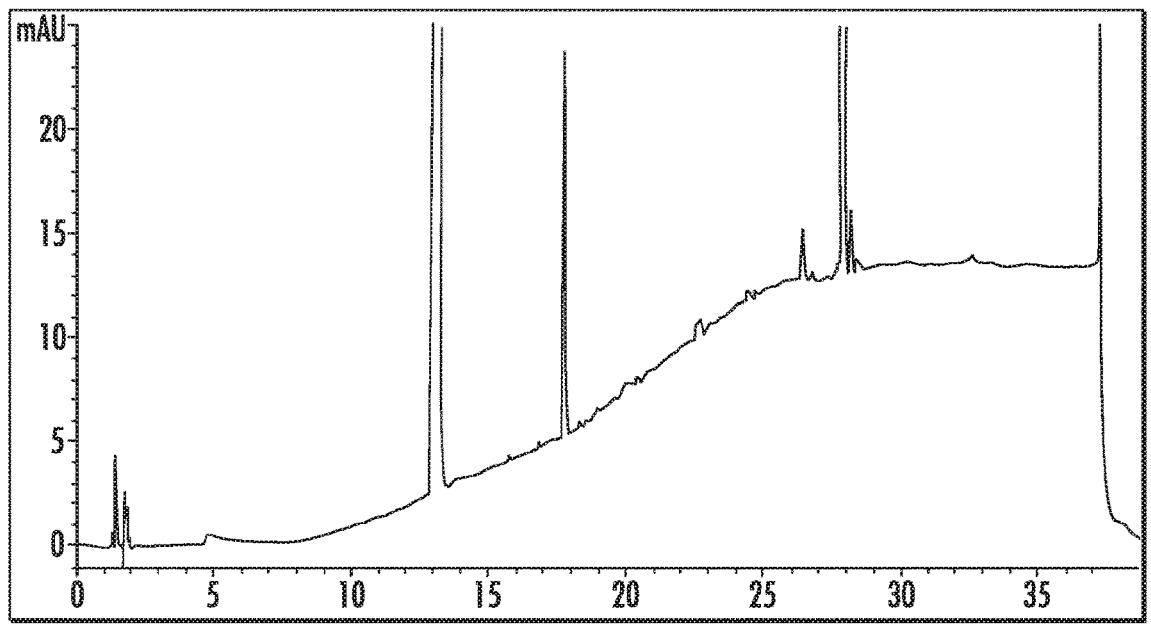
FIG. 17B shows an expanded view of the data of FIG. 17A, along with the area percent report.
Figure 17D:
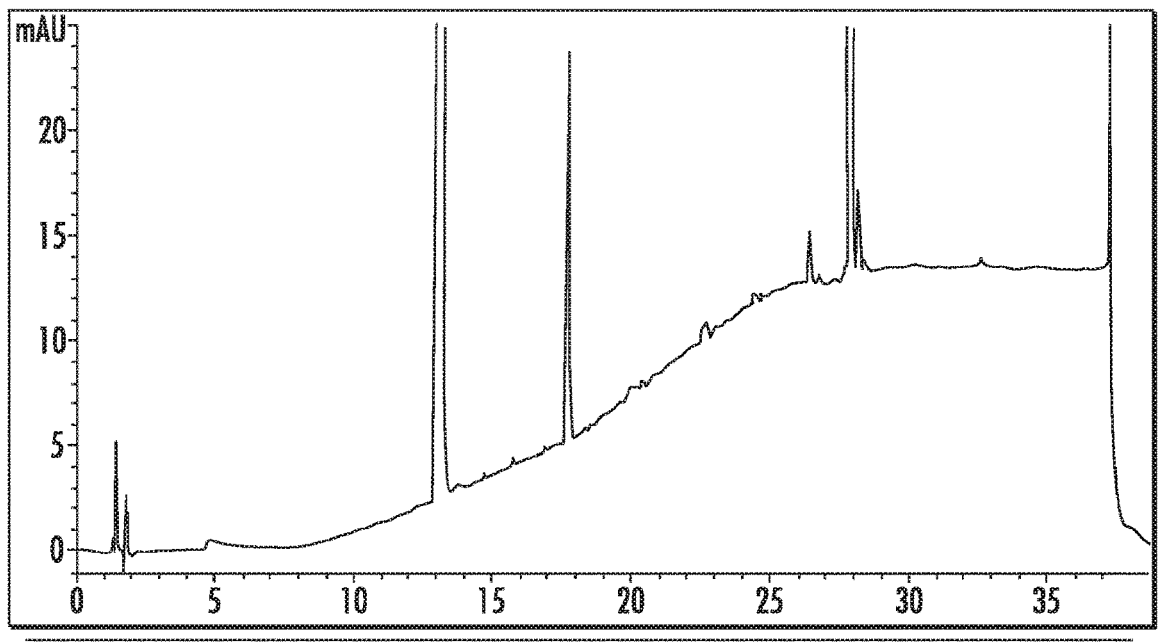
FIG. 17D shows an expanded view of the data of FIG. 17C, along with the area percent report.

NMR data for the Acid A by-product is shown in FIGS. 13A-13C. $^1$H NMR (400 MHz, CDCl$_3$) 1.2-1.8 (8H, m, 4 CH$_2$ groups from cyclopentyl ring), 2.9-3.0 (1H, m, CH group from cyclopentyl ring), 6.2 (1H, br s, OH/tertiary alcohol), 7.2-7.7 (5H, m, aromatic protons/phenyl group).

NMR data for the glycopyrronium Hydrolysis By-Product, Quaternary amino alcohol (QAA) is shown in FIGS. 14A-14D. $^1$H NMR (400 MHz, D$_2$O) 2.1-2.3 (1H, m, —CH—C—N$^+$), 2.5-2.7 (1H, m, —CH—C—N$^+$), 3.2 (3H, s, CH$_3$—N$^+$), 3.3 (3H, s, CH$_3$—N$^+$), 3.5-3.7 (2H, m, —CH$_2$—N$^+$), 3.7-3.9 (2H, m, —CH$_2$—N$^+$), 4.75-4.85 (1H, m, —CH—OH, methine proton).

When the glycopyrronium stearate hydrolyzes, it results in Acid A and QAA. QAA was very difficult to analyze using HPLC, because it does not have a strong chromophore and comes off very early in the HPLC analysis.

The loss of glycopyrronium fatty acid salts to the aqueous washes was higher than desired but the procedure is workable to prepare samples. Some methods to improve salt recovery include, but are not limited to, performing a back extraction, salting out, or choosing alternative extraction solvents. Both the glycopyrronium moiety and stearic acid are lost to the aqueous washes but the ratio of stearic acid to glycopyrronium in the isolated product is enriched compared to the input levels (2.2:1 as input, 2.35:1 isolated) The final ratio may be further adjusted with adjustments in the free fatty acid input.

There was an effective purge of bromide during work up and isolation. More specifically, the work up and isolation procedure consistently provided very low levels (<0.1%) of bromide. This may permit optimization of the washes for enhanced glycopyrronium recovery in the process while still providing control of residual bromide to acceptable levels.

The resulting glycopyrronium stearate sample was characterized by HPLC and GC and consistent with NMR results. Confirmed results by separate, complementary analytical methods validated the results. The sample stability was improved over the initial studies. The samples isolated with higher excess free fatty acid have improved stability with degradation observed only after months at ambient conditions. The excess free fatty acid appears to act as a buffer, to slow down degradation of the desired fatty acid salts.

Preparation of Glycopyrronium Fatty Acid Salts

As a more general description for preparing glycopyrronium fatty acid salts, the calculated target amount of fatty acid (FA) is mixed with water (approximately 8 mL/g FA input), 2-methyl-tetrahydrofuran (2-Me-THF, approximately 8 mL/g FA input), and metal hydroxide such as an alkali metal hydroxide or an alkaline earth metal hydroxide (e.g.—potassium hydroxide KOH, 1.1 molar equiv). In preferred embodiments, the calculated target amount is 2.2 molar equivalents (a 1.2 molar equivalent excess). In other embodiments, the calculated amount is greater than or equal to 1.2 molar equivalents (0.2 molar equivalent excess). The mixture is stirred until all solids are dissolved. Glycopyrronium bromide ("GPBr", 1.0 molar equiv.) is added and mixed until the solids are dissolved. Mixing is stopped and the phases are allowed to separate. The lower aqueous phase (pH approximately 7) is removed and the upper organic phase is retained. The upper organic phase is washed three times with water (each wash ~3.2 mL/g fatty acid input). Each lower aqueous phase (pH ~7) is removed and the upper organic phase is retained.

The rich upper organic phase is concentrated by vacuum distillation using minimal heating (20-25° C./25-30 Torr) to obtain a mushy paste. Fresh 2-Me-THF (approximately 4.8 mL/g FA input) is added and vacuum concentration is conducted (20-25° C./25-30 Torr) until no further distillate is observed.

Heptane (approximately 8 mL/g fatty acid input) is added and the mixture is stirred until most of the solids dissolve. Some of the excess free fatty acid may remain as a thin slurry which is passed through a filter to remove the remaining solids. The rich filtered heptane solution is concentrated by vacuum distillation using minimal heating (20-25° C./25-30 Torr) to obtain a waxy solid.

Additional fatty acids were used to prepare glycopyrronium fatty acid salts using the methods described herein. More specifically, lauric acid (sample PSG-008-002), palmitic acid (sample PSG-008-204) and linoleic acid (sample PSG-008-206) were used as starting materials, in addition to the stearic acid (sample EE-008-008) samples discussed above. The results are shown in Tables 23 A and 23B. The theoretical maximum recovery was calculated as total recovery of glycopyrronium fatty acid and excess free fatty acid.

TABLE 23A

| Sample Name | Lot # | File | Sample wt (mg) | GP PA (peak area) | Assay | Average Assay |
|---|---|---|---|---|---|---|
| GP Laurate | PSG-008-202 | 09 | 33.86 | 1469.4 | 34.544% | 34.703% |
| | | 10 | 33.80 | 1480.3 | 34.862% | |
| GP Palmitate | PSG-008-204 | 11 | 36.74 | 1372.6 | 29.739% | 29.934% |
| | | 12 | 36.03 | 1363.7 | 30.129% | |
| GP Linoleate | PSG-008-206 | 13 | 37.99 | 1163.5 | 24.379% | 26.749% |
| | | 14 | 38.33 | 1402.1 | 29.118% | |

TABLE 23B

| Sample | Theoretical Maximum Recovery* | Prep Output | Mass Yield | GP Wt % HPLC | Comments |
|---|---|---|---|---|---|
| EE-008-008 Stearic Acid | 9.44 g | 5.35 g | 56.67% | 31.4% | Waxy Solid |
| PSG-008-202 Lauric Acid | 7.58 g | 6.08 g | 80.2% | 34.7% | Oily Solid |
| PSG-008-204 Palmitic Acid | 8.82 g | 3.00 g | 34.0% | 29.9% | Oily Solid |
| PSG-008-206 Linoleic Acid | 9.34 g | 9.32 g | 99.8% | 26.7% | Oily Solid |

*Calculated as total recovery of GPFA and excess free FA

The HPLC data for glycopyrronium stearate is shown in FIGS. 7 and 8. The HPLC data for glycopyrronium laurate is shown in FIGS. 15A-15D. Peak 1 indicates glycopyrronium laurate, and includes an area % of 90.8652 and 90.8662, respectively in the two runs. Peak 7 indicates the by-product Acid A, which includes a 5.7508% area and a 5.758% area in the two runs. The other minor peaks are unidentified impurities or artifacts.

The HPLC data for glycopyrronium palmitate is shown in FIGS. 16A-16D. Peak 1 indicates glycopyrronium palmitate, and includes an area % of 91.2525 and 91.3890, respectively in the two runs. Peak 5 indicates the by-product Acid A, which includes a 4.1180% area and a 4.0100% area, respectively in the two runs. The other minor peaks are unidentified impurities or artifacts.

The HPLC data for glycopyrronium linoleate is shown in FIGS. 17A-17D. Peak 1 indicates glycopyrronium linoleate, and includes an area % of 39.7889 and 39.5620, respectively for the two runs. Peak 4 indicates the by-product Acid A in the first run (FIGS. 17A-17B) and peak 5 indicates the by-product Acid A in the second run (FIGS. 17C-17D), and includes a 2.4126% area and 2.4171% area, respectively for the two runs. Peak 15 (FIGS. 17A-17B and peak 17 (FIGS. 17C and 17D) actually had the highest area percentage (55.1974 and 55.4318, respectively). These peaks are consistent with the excess free linoleic acid used in the reaction, which was detected in this HPLC due to the conjugated C=C double bond chromophore. Of the fatty acids tested, only the linoleic acid shows a significant response with the UV detector. The other minor peaks are unidentified impurities or artifacts. A more accurate assessment of the amount of free linoleic acid can be carried out by gas chromatography, with a minor optimization of parameters used for the analysis of stearic acid.

As an analysis tool, HPLC was only able to identify the desired product (glycopyrronium stearate, glycopyrronium laurate, glycopyrronium palmitate and glycopyrronium linoleate) and Acid A in the samples. Given the complexity of the reagents and products, other methods were required to identify the fatty acids (gas chromatography), the desired products and by-products (NMR), and the residual bromide and potassium (ion chromatography) in the samples.

Figure 18:
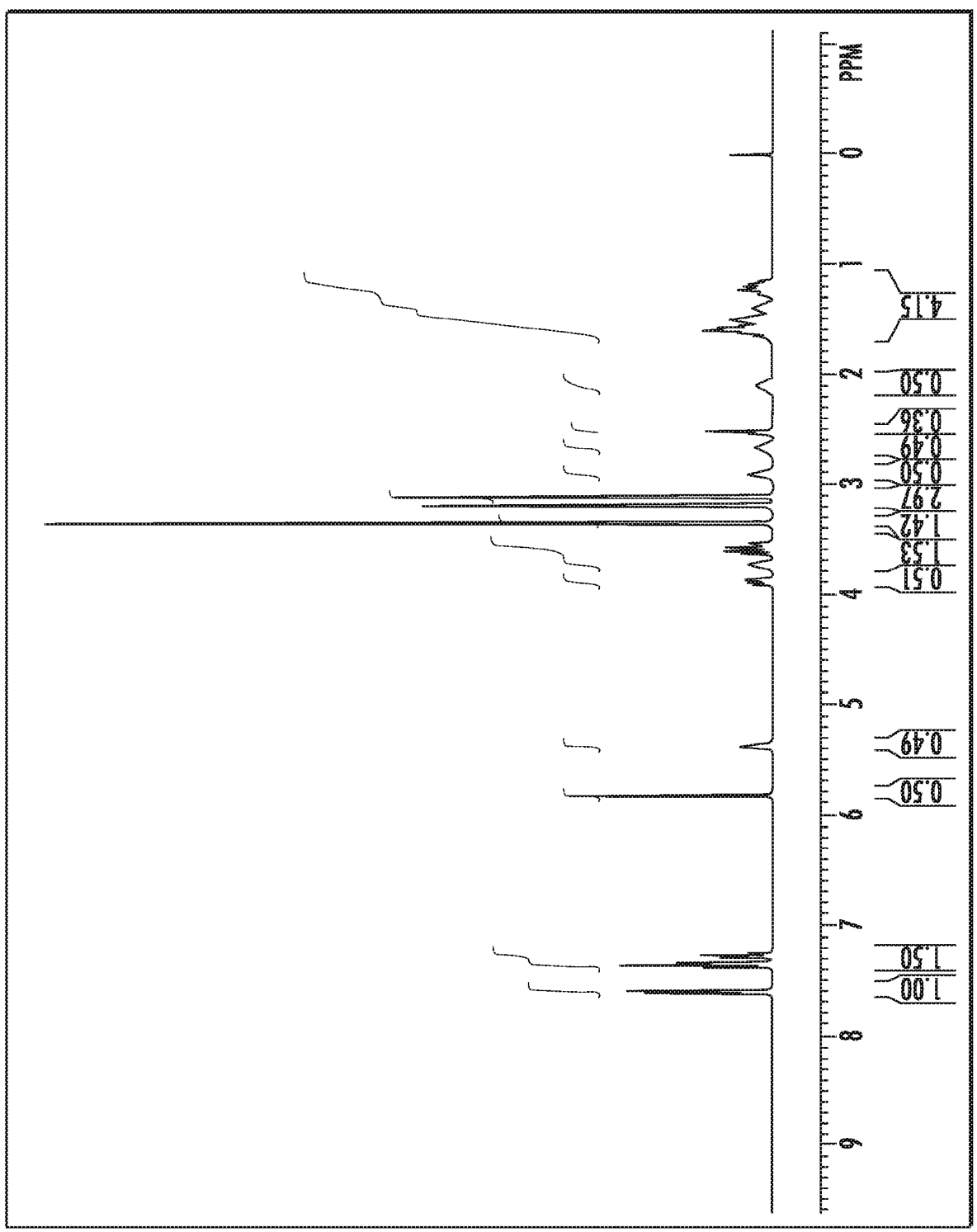
FIG. 18 shows NMR data for glycopyrronium bromide, residual water in DMSO-d6 at 3.33 ppm, singlet.

All NMR chemical shifts are provided in ppm relative to tetramethylsilane (TMS). NMR data for glycopyrronium bromide is shown in FIG. 18. $^1$H NMR (400 MHz, DMSO-$d_6$) 1.1-1.7 (8H, m, 4 $CH_2$ groups from cyclopentyl group), 2.0-2.2 (1H, m, —CH—C—$N^+$), 2.6-2.8 (1H, m, —CH—C—$N^+$), 2.8-3.0 (1H, m, CH group from cyclopentyl group), 3.1 (3H, s, $CH_3$—$N^+$), 3.2 (3H, s, $CH_3$—$N^+$), 3.45-3.65 (2H, m, —$CH_2$—$N^+$), 3.65-3.85 (1H, m, —CH—$N^+$), 3.85-3.95 (1H, m, —CH—$N^+$), 7.20-7.65 (5H, m, aromatic protons/phenyl group). NMR data for glycopyrronium stearate is discussed above and is shown in FIGS. 11 and 12A-12C.

Figure 19:
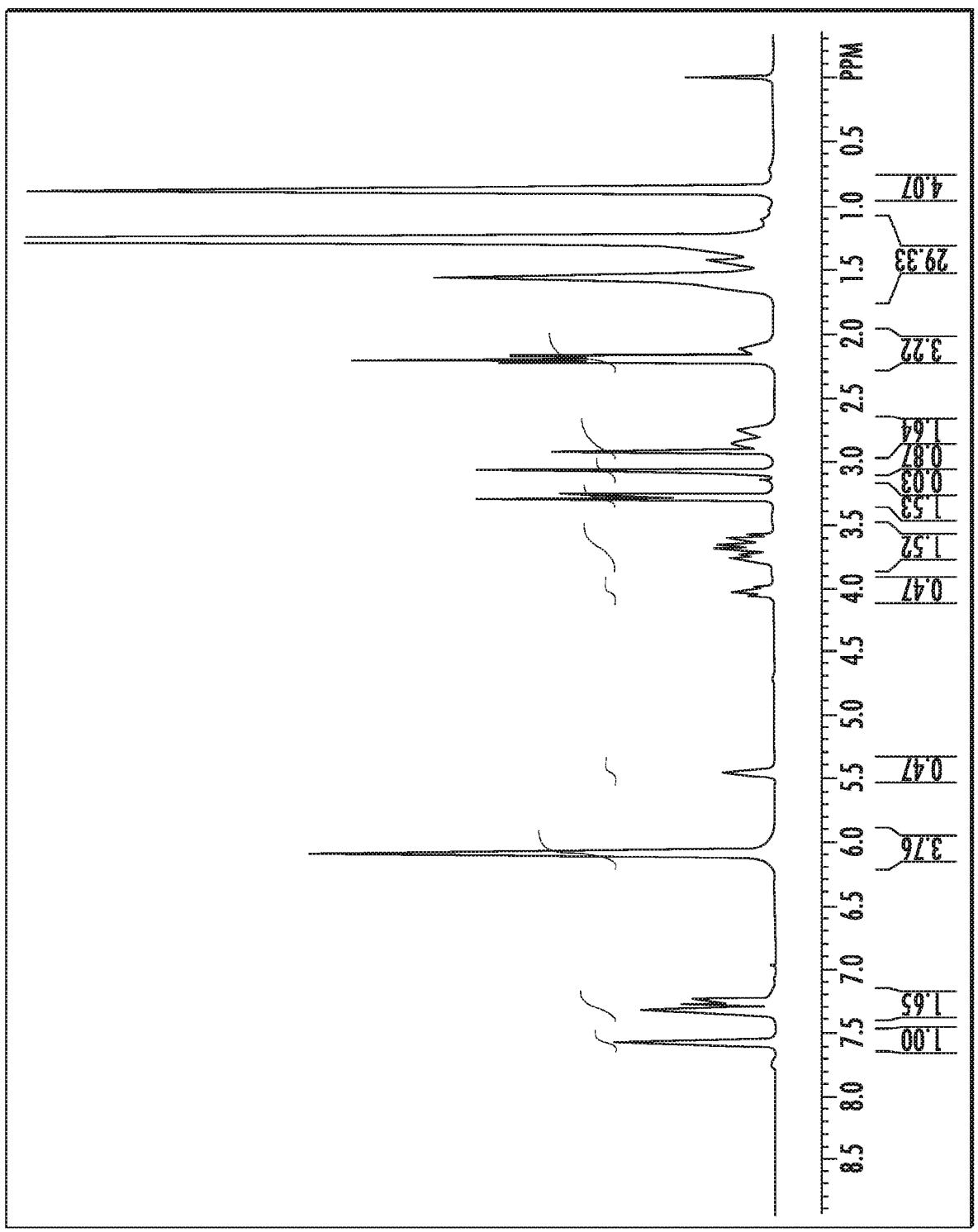
FIG. 19 shows NMR data for glycopyrronium laurate.

NMR data for glycopyrronium laurate is shown in FIG. 19. $^1$H NMR (400 MHz, CDCl3) 0.87 (3H, t, CH3-), 1.20-1.70 (18H, m, 9 —CH2 groups from fatty acid chain and 8H, m, 4 —CH2 groups from cyclopentyl ring), 2.1-2.25 (1H, m, —CH—C—N+), 2.23 (2H, t, —CH2C=O), 2.7-3.0 (1H, m, —CH—C—N+ and 1H, m, CH group from cyclopentyl group), 2.95, 3.10, 3.28, 3.30 (6H, 4 sets of singlets, 2 —CH3-N+; chemical shift differences at the charged interface possibly due to different aggregation states of the fatty acid salt), 3.6-3.85 (2H, m, —CH2-N+ and 1H, m, —CH—N+), 3.95-4.1 (1H, m, —CH—N+), 5.4-5.5 (1H, m, —CH—OH, methine proton), 7.2-7.6 (5H, m, aromatic protons/phenyl group).

Figure 20:
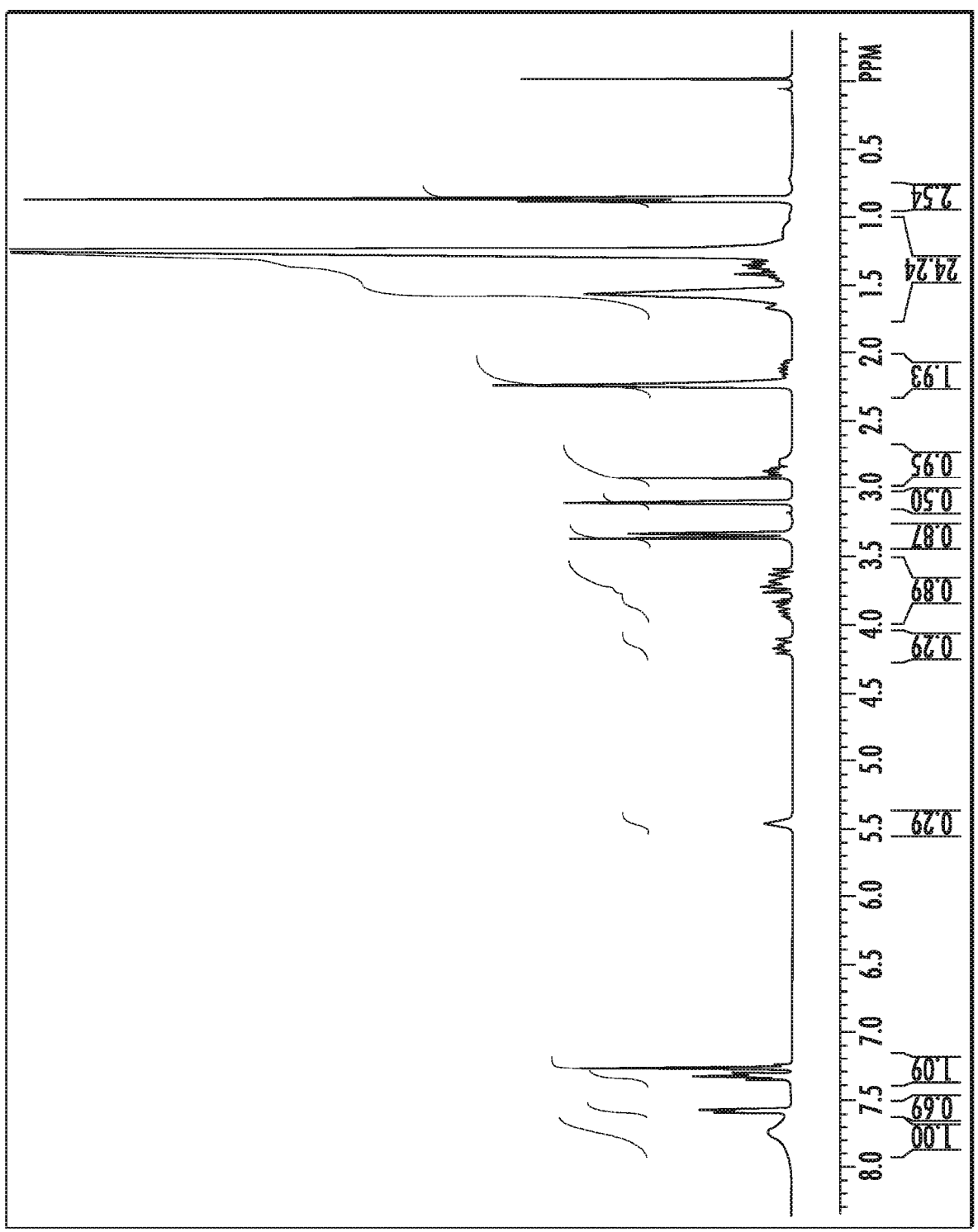
FIG. 20 shows NMR data for glycopyrronium palmitate.

NMR data for glycopyrronium palmitate is shown in FIG. 20. $^1$H NMR (400 MHz, $CDC_{13}$) 0.88 (3H, t, CH3-), 1.20-1.70 (26H, m, 13 —CH2 groups from fatty acid chain and 8H, m, 4 —CH2 groups from cyclopentyl ring), 2.0-2.2 (1H, m, —CH—C—N+), 2.25 (2H, t, —CH2C=O), 2.7-2.95 (1H, m, —CH—C—N+ and 1H, m, CH group from cyclopentyl group), 2.93, 3.11, 3.34, 3.37 (6H, 4 sets of singlets, 2 —CH3-N+; chemical shift differences at the charged interface possibly due to different aggregation states of the fatty acid salt), 3.6-3.8 (2H, m, —CH2-N+), 3.8-4.0 (1H, m, —CH—N+), 4.1-4.25 (1H, m, —CH—N+), 5.40-5.55 (1H, m, —CH—OH, methine proton), 7.2-7.6 (5H, m, aromatic protons/phenyl group).

Figure 21:
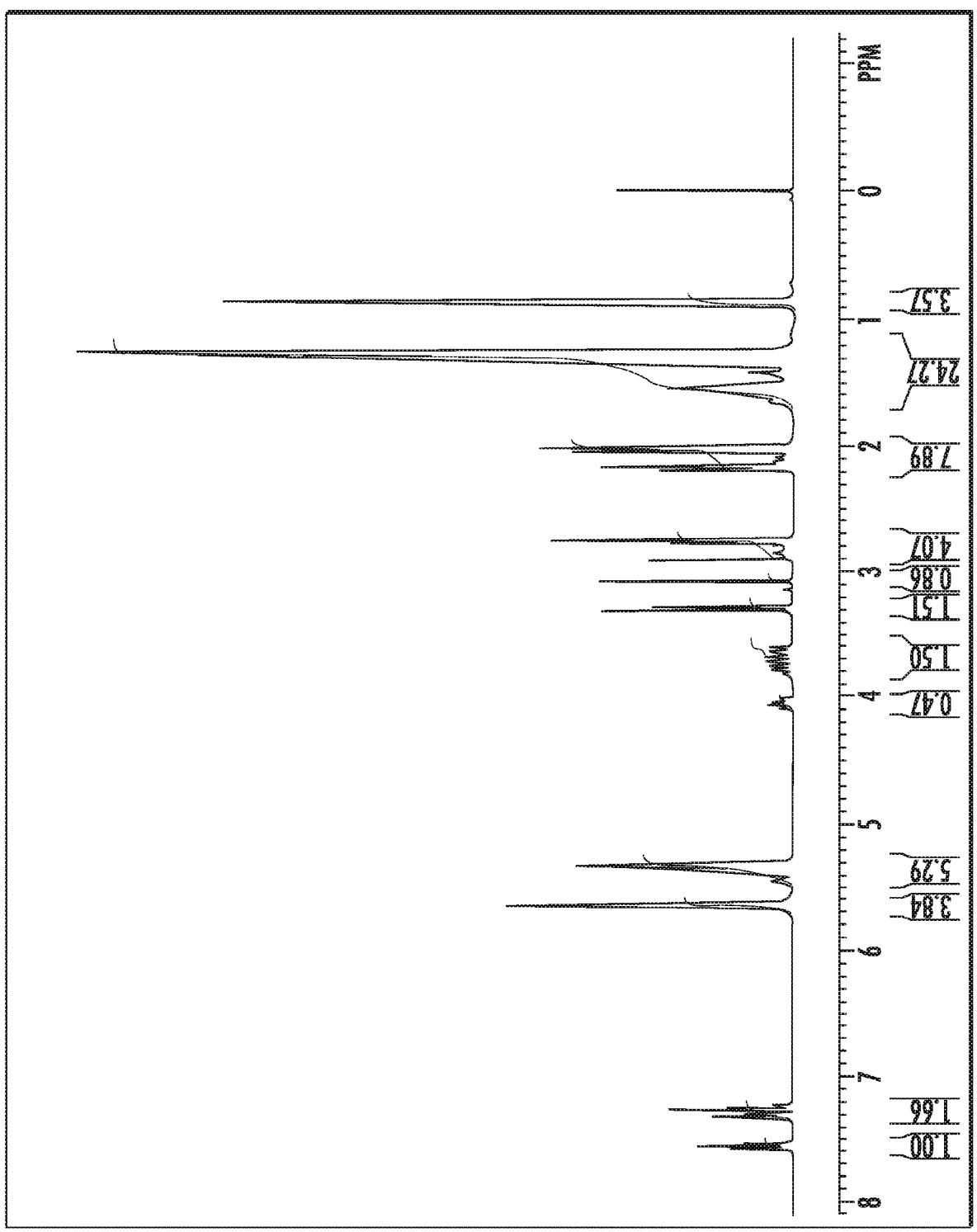
FIG. 21 shows NMR data for glycopyrronium linoleate.

NMR data for glycopyrronium linoleate is shown in FIG. 21. $^1$H NMR (400 MHz, $CDCl_3$) 0.88 (3H, t, $CH_3$—), 1.20-1.70 (16H, m, 8 —$CH_2$ groups from fatty acid chain and 8H, m, 4 —$CH_2$ groups from cyclopentyl ring), 2.0-2.1 (4H, m, allylic protons —$CH_2$—C=C), 2.0-2.2 (1H, m, —CH—C—$N^+$), 2.2 (2H, t, —$CH_2$C=O), 2.85 (2H, t, doubly allylic protons C=C—$CH_2$—C=C), 2.7-2.9 (1H, m, —CH—C—$N^+$ and 1H, m, CH group from cyclopentyl group), 2.91, 3.09, 3.29, 3.31 (6H, 4 sets of singlets, 2 —$CH_3$—$N^+$; chemical shift differences at the charged interface possibly due to different aggregation states of the fatty acid salt), 3.6-3.9 (2H, m, —$CH_2$—$N^+$ and 1H, m, —CH—$N^+$), 4.0-4.15 (1H, m, —CH—$N^+$), 5.25-5.50 (2H, m, olefinic protons), 5.35-5.50 (1H, m, —CH—OH, methine proton), 5.6-5.75 (2H, m, olefinic protons), 7.2-7.6 (5H, m, aromatic protons/phenyl group)

NMR analysis could be effectively used to accurately assess the molar ratio of glycopyrronium to the total amount of fatty acid component (i.e. stoichiometrically bound fatty acid anion and free fatty acid). A comparison of $H^1$NMR results for the glycopyrronium fatty acid salt samples is shown in Table 24. Interfering peaks were noted in the aromatic region for the stearic acid sample, but the glycopyrronium multiplets were sharp with no interference.

TABLE 24

| Sample | Integration of Fatty Acid Methyl (3 H total) | Integration of GP Aromatic Peaks (5 H total) | Integration of GP Multiplets (4 H total) 3.5-4.2 ppm | Mole Ratio Fatty Acid/GP Calculated from FA Methyl & GP Multiplets |
|---|---|---|---|---|
| EE-008-008 Stearic Acid | 1.41 (H = 0.47) | 1.70 (H = 0.34) | 0.82 (H = 0.205) | 2.29:1 |
| PSG-008-202 Lauric Acid | 4.07 (H = 1.3567) | 2.65 (H = 0.53) | 1.99 (H = 0.4975) | 2.73:1 |
| PSG-008-204 | 2.54 | 1.78 | 1.18 | 2.87:1 |

TABLE 24-continued

| Sample | Integration of Fatty Acid Methyl (3 H total) | Integration of GP Aromatic Peaks (5 H total) | Integration of GP Multiplets (4 H total) 3.5-4.2 ppm | Mole Ratio Fatty Acid/GP Calculated from FA Methyl & GP Multiplets |
|---|---|---|---|---|
| Palmitic Acid PSG-008-206 Linoleic Acid | (H = 0.8467) 3.57 (H = 1.19) | (H = 0.356) 2.66 (H = 0.532) | (H = 0.295) 1.97 (H = 0.4925) | 2.42:1 |

The glycopyrronium HPLC assay (GP wt % Content) is applicable to a variety of fatty acid salts. While the HPLC method was developed with glycopyrronium stearate, no interfering peaks or other issues were observed in the analysis of glycopyrronium fatty acid salts prepared from lauric, palmitic and linoleic acids enabling quantitation of the glycopyrronium content in these mixtures.

Similarly, NMR effectively characterizes a variety of fatty acid salts using a number of different fatty acid substrates. As in the case of glycopyrronium Stearate, the terminal methyl group of the fatty acid chain (3H) provided suitable integration for comparison with the glycopyrronium (GP) multiplets (4H total, 3.5-4.2 ppm) for calculation of the mole ratio (GP:FA) present in the isolated materials for glycopyrronium fatty acid salts prepared from lauric, palmitic, and linoleic acids.

The glycopyrronium fatty acid salt samples were relatively stable. The level of the degradant "Acid A" was low in all samples at the initial isolation but stability over time (months) was only examined for glycopyrronium stearate. For glycopyrronium stearate, degradation was observed over ~4 months at ambient conditions.

The mass recovery was variable across the different fatty acids. The mass recovery varied from worse to much better across the glycopyrronium fatty acid samples (Palmitic<Stearic<Lauric<Linoleic). This highlights the opportunity for additional procedure optimization by further improving retention of glycopyrronium salt activity and recovery in the isolated glycopyrronium fatty acid salts. Some methods to improve salt recovery include, but are not limited to, performing a back extraction, salting out, or choosing alternative extraction solvents.

Extended drying was required to achieve a low level of residual n-heptane (drying until heptane undetectable by NMR), particularly with lauric and palmitic acids. Further optimization of drying conditions may improve the process. For example, the vacuum and/or temperature of the drying conditions could be adjusted to improve the process while avoiding degradation.

Similar mole ratios were noted for fatty acid:glycopyrronium (FA:GP) in the final products. All of the isolated glycopyrronium fatty acid salt mixtures showed some enrichment of the fatty acid (relative to glycopyrronium) compared to the input ratio. The isolated products all had more than the 2.2:1 FA:GP input ratio.

Fatty acids enjoy a GRAS (Generally Regarded as Safe) status, are widely used in drug formulations, and are found in many foods that are currently consumed. So, a large excess of free fatty acid in the glycopyrronium fatty acids is not likely to pose a problem for the use of the glycopyrronium fatty acids in drug development.

The current preparative and analytical methods may be applied to other fatty acids, preferably fatty acids with at least eight carbon molecules. Some examples include, but are not limited to, arachidic acid, stearic acid, palmitic acid, oleic acid, erucic acid, arachidonic acid, lauric acid, capric acid, linoleic acid, linolenic acid, or myristic acid to make glycopyrronium fatty acid salts.

Analysis of Products and Degradants

The analytical methods needed to be sufficient to characterize composition and purity as meeting regulatory requirements to enable further development. The lack of chromophores for fatty acid components and 3-hydroxy-1,1-dimethyl pyrrolidinium degradants required the development of alternatives to HPLC/UV. The lack of retention/separation of bromide and 3-hydroxy-1,1-dimethyl pyrrolidinium by HPLC required the development and use of separate, complementary methods to quantitate these components.

Challenging solubility properties of the active pharmaceutical ingredient mixture (sample precipitation, column plugging, accelerated loss of column performance) hindered method development but these issues were ultimately overcome. No single method was suitable for all components of analysis so complementary (orthogonal) methods were required and successfully developed.

Samples of a crude product mixture and each of the key hydrolysis by-products were prepared and analyzed along with samples of the starting materials to enable method development. The samples prepared are shown in Table 25.

TABLE 25

| Sample ID | Description |
|---|---|
| EE-008-001-1 | Glycopyrronium Bromide (GPBr), lot # 6908953CD Starting Material |
| EE-008-001-2 | Stearic Acid, SAFC lot # 39397PJ Starting Material (used in excess) |
| EE-008-001-3a | Filterable Solids from GPBr/Stearic Acid/Potassium Stearate (recovered portion of stearic acid) |
| EE-008-001-3b | Waxy Solids from GPBr/Stearic Acid/Potassium Stearate API mixture of GP Stearate and excess free Stearic acid |
| EE-008-001-4a | GP Hydrolysis By-Product, Organic Acid ("Acid A") CAS 427-49-6, α-cyclopentyl-α-hydroxy-benzene acetic acid |
| EE-008-001-4b | GP Hydrolysis By-Product, Quaternary aminoalcohol ("QAA") CAS 51052-74-5, 3-hydroxy-1,1-dimethyl pyrrolidinium bromide mixture with NaBr |

By-Product (Degradant) Sample Preparation

Hydrolysis of glycopyrronium bromide and isolation of the by-products was performed. A mixture of 3.98 g (10 mmol, 1.0 eq.) glycopyrronium bromide, 0.80 g (20 mmol, 2.0 eq.) sodium hydroxide, and 20 mL of water was stirred at room temperature overnight. The resulting solution was filtered through filter paper to remove traces of sticky solids and then acidified by the drop-wise addition of 4.78 g (28.35 mmol, 2.835 equiv.) of 48% Aq. hydrobromic acid. A thick white slurry formed which was then filtered and washed with ~5 mL of water. The isolated white solids were air dried giving 2.025 g of "Acid A" (CAS 427-49-6, α-cyclopentyl-α-hydroxy-benzene acetic acid). The combined filtrate and rinse was vacuum concentrated at 40° C./9 Torr to provide 3.87 g of an oily paste containing the Quaternary Amino Alcohol By-Product (CAS 51052-74-5,3-hydroxy-1,1-dimethyl pyrrolidinium bromide) as well as NaBr in ~0.95/1 w/w ratio.

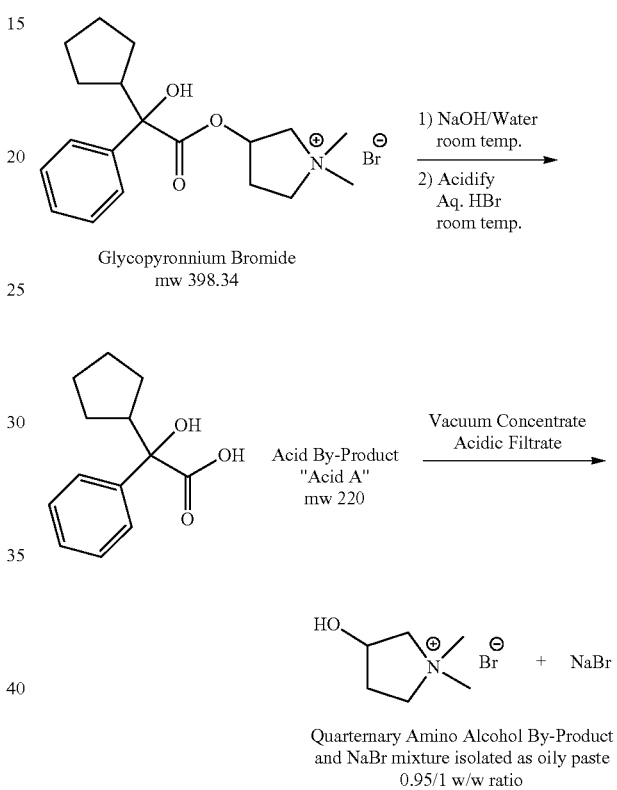

HPLC Methods

A unique HPLC method was developed to analyze the products of the reaction. Table 26 shows screening for HPLC method conditions.

TABLE 26

| Columns Screened: | Mobile Phases Used |
|---|---|
| Phenomenex Luna C18(2) 4.6 × 150 mm, 3μ | 1$^{st}$ set: |
| Waters Atlantis T3, 4.6 × 150 mm, 3μ | Mobile Phase A: 0.1% $H_3PO_4$ in DI $H_2O$ |
| SIELC Primesep 100, 4.6 × 150 mm, 5μ | Mobile Phase B: 0.1% $H_3PO_4$ in ACN |
| Waters Symmetry C18, 4.6 × 150 mm, 3.5μ | 2$^{nd}$ set: |
| Zorbax Eclipse XDB C8, 4.6 × 150 mm, 5μ | Mobile Phase A: 0.01M $KH_2PO_4$ pH 6.5 in DI $H_2O$ |
| Zorbax Eclipse XDB C18, 4.6 × 150 mm, 5μ | Mobile Phase B: 100% ACN |
| Phenomenex Hydroxy RP, 4.6 × 250 mm, 5μ | 3$^{rd}$ set: |
| | Mobile Phase A: 0.01% TFA in DI $H_2O$ |
| | Mobile Phase B: 0.01% TFA in ACN |

In addition to the listed screening, the USP method for Glycopyrrolate was evaluated. This method used Kinetex C18, 4.6×100 mm, 2.6μ, Mobile Phase A: 0.025M $KH_2PO_4$ pH 2.5 with $H_3PO_4$ in DI $H_2O$, and Mobile Phase B: 100% CAN. As per the USP method, the diluent was 1:1 mobile phase A and B, at 0.5 mg/mL sample concentration.

The first sample of glycopyrronium stearate (EE-008-001-3b, waxy solids from GPBr/Stearic Acid/Potassium Stearate, Table 25) seemed soluble in the USP diluent but methanol was used for consistency across all of the screened conditions and all samples were prepared at 0.5 mg/mL in MeOH.

With the USP Method, the baseline was not good (very irregular baseline). Also, numerous small peaks were observed on replicate injections. Precipitation on the column was suspected as the cause of the problem, so mobile phase mixtures were checked for precipitation. It was found that, at the high end of the gradient (15% mobile phase A and 85% mobile phase B), $KH_2PO_4$ buffer precipitated. Most of the C18 columns adequately retained glycopyrrolate (GP). The peak shape (GP) was found to be better at the lower pH (phosphoric acid).

From the screened conditions, the Agilent, ZORBAX Eclipse XDB-C18, 4.6×150 mm, 5 μm, P/N: 993967-902 and the 0.1% $H_3PO_4$ in $H_2O$/acetonitrile solvent system provided the best performance (baseline and peak shape). However, the degradant "QAA" (shown in Table 2, item 8, sample EE-008-001-4b) co-eluted with the bromide peak. Despite extensive efforts, the retention and separation of the bromide and QAA peaks could not be improved.

Glycopyrronium and the "Acid A" degradant were readily resolved from other components and quantitated by HPLC and a weight percent assay for glycopyrronium content was developed. While it was desired to directly quantitate the QAA content by HPLC, it remained necessary to determine bromide by a separate method (IC) and then estimate the QAA content by HPLC using a calculation to subtract the bromide content. During the course of the HPLC method development, it was observed that "Acid A" was not observed in sample EE-008-001-3b for the first month of use.

One analytical method that was developed was a method for quantitation of chromophoric starting materials, products and degradants. The method used HPLC with photodiode array detection (PDA).

A glycopyrronium stearate HPLC method was developed, which provides a procedure for the determination of glycopyrronium or 3[(cyclopentylhydroxyphenylacetoxy]-1, 1-dimethyl pyrrolidinium (GP) stearate assay and impurity profile by HPLC.

The HPLC operating conditions for the Agilent, ZORBAX Eclipse XDB-C18, 4.6×150 mm, 5 μm, P/N: 993967-902 column are shown in Table 27 and the mobile phase gradient is shown in Table 28. 0.1% of 0.25 mg/mL GPBr, average S/N=11.2. Linearity from 25% to 120% of 0.25 mg/mL GPBr is linear. The correlation coefficient=1.000.

TABLE 27

| Injection Volume | 10 μL |
|---|---|
| Mobile Phase A | 0.1% $H_3PO_4$ in $H_2O$ |
| Mobile phase B | 0.1% $H_3PO_4$ in ACN |
| Gradient | See table below |
| Flow Rate | 1 mL/min |

TABLE 27-continued

| Runtime | 40 mins |
|---|---|
| Column Temperature | 30° C. |
| UV wavelength | 210 nm; For Diode Array detector, use 210 nm Bw = 8, reference 360 nm, Bw = 100 |

TABLE 28

| Time (minutes) | A % | B % |
|---|---|---|
| 0.0 | 90 | 10 |
| 5.0 | 90 | 10 |
| 25.0 | 5 | 95 |
| 35.0 | 5 | 95 |
| 35.1 | 90 | 10 |
| 40.0 | 90 | 10 |

Figure 22:
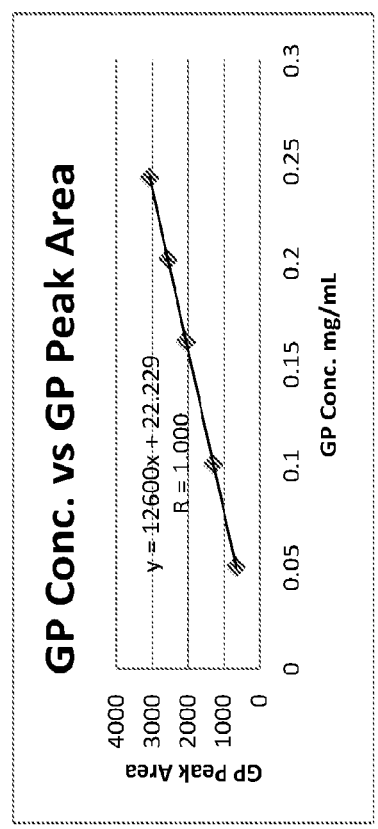
FIG. 22 shows the glycopyrronium concentration versus glycopyrronium peak area.
Figure 23:
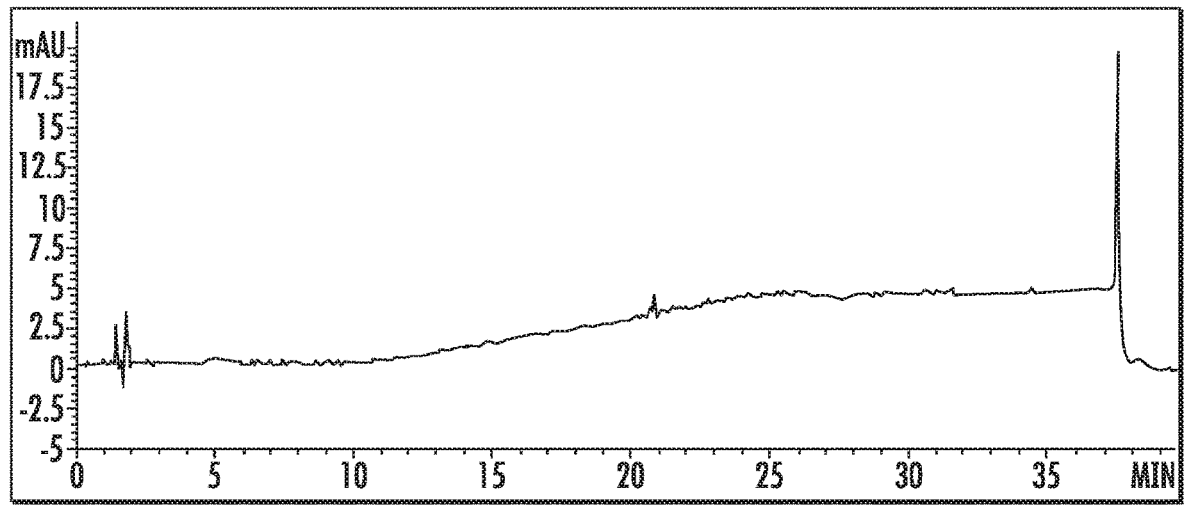
FIG. 23 shows a blank chromatogram.
Figure 24:
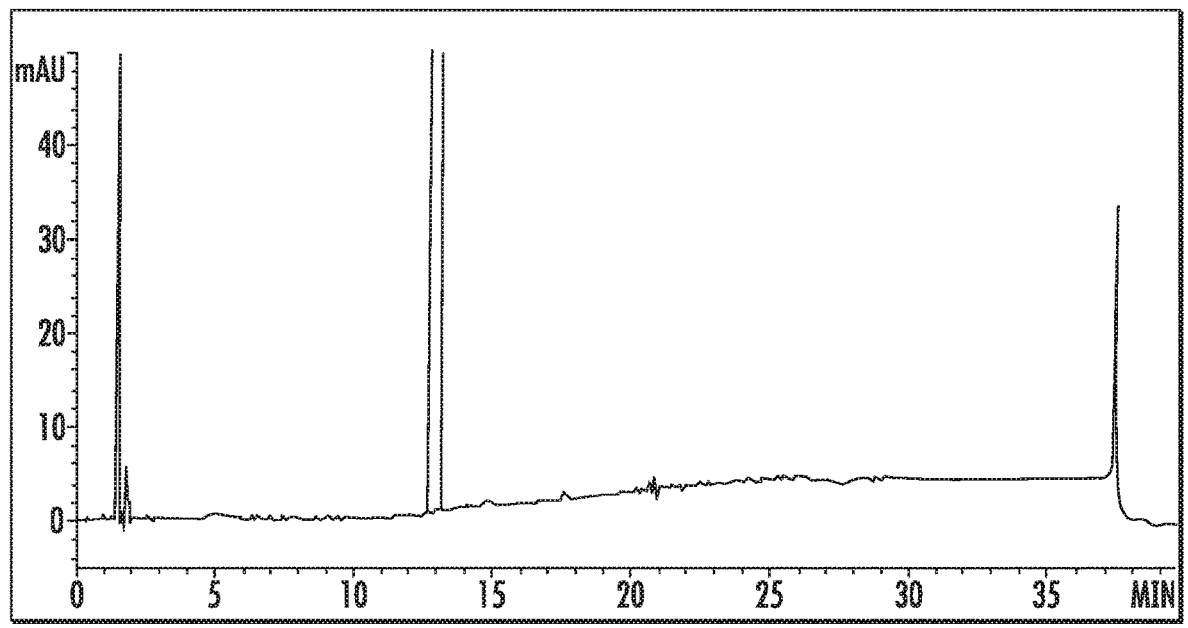
FIG. 24 shows a resolution solution chromatogram.

FIG. 22 shows the glycopyrronium concentration versus glycopyrronium peak area. FIG. 23 shows a blank chromatogram and FIG. 24 shows a resolution solution chromatogram. Method accuracy is shown in Table 29.

TABLE 29

| Name | Recovery |
|---|---|
| 80%-1 | 100.77% |
| 80%-2 | 101.37% |
| 100%-1 | 101.20% |
| 100%-2 | 99.909% |
| 120%-1 | 101.35% |
| 120%-2 | 100.94% |
| Average | 100.92% |
| Standard Deviation | 0.5% |

Ion Chromatography for Bromide Content

Another method quantitated the residual bromide ion in the product using ion chromatography (anion mode). The first rough check of the glycopyrronium stearate sample EE-008-001-3b (Table 10 p.19) showed <1% w/w bromide (limit test). A full calibration sequence and analysis was carried out. All results indicated effective removal of bromide. The final bromide assay method can check and control residual bromide ion to ≤0.1%.

This method was developed to provide a procedure for the determination of trace amounts of residual bromide ion in glycopyrronium stearate/stearic acid mixtures using ion chromatography. The analytical method applies to the quantitation of residual bromide ion in glycopyrronium stearate/stearic Acid mixtures. The method corresponds to 0.1% (1000 ppm) limit for bromide ion of a 0.5 mg/mL sample concentration.

The ion chromatographic parameters and conditions are shown in Table 30.

TABLE 30

| Instrument | Parameter | Condition |
|---|---|---|
| Auto Sampler AS-DV | Sampler Flush Factor | 10 |
| | Sampler Delay Volume | 125 µL |
| | Sampler Deliver Speed | 4.0 mL/min |
| | Sampler Deliver Sample | Full |
| RFIC | Data Collection Rate | 5.0 Hz |
| | Column Temperature | 30° C. |
| | Cell Temperature | 35° C. |
| | Eluent Generator Conc. | 10 mM |
| | Suppressor Current | 10 mA |
| | Flow Rate | 0.5 mL/min |
| | Injection Volume | 10 µL |
| | Run Time | 21.0 min |

| | Stage | Time (min) | Command | Value |
|---|---|---|---|---|
| Program Parameters | Equilibration | −3.000 | | |
| | | −2.700 | Pump_ECD.Pump_ECD_Relay_1.Closed | Duration = 138 seconds |
| | Start Run | 0.00 | Pump_ECD.Channel_Pressure.AcqOn | |
| | | | Pump_ECD.Autozero | |
| | | | Pump_ECD.ECD_1.AcqOn | |
| | | | Pump_ECD_Total.AcqON | |
| | | | Pump_InjectValve.Inject Position | Duration = 30 seconds |
| | Run Time | 0.00 | | Duration = 18 minutes |

Figure 25:
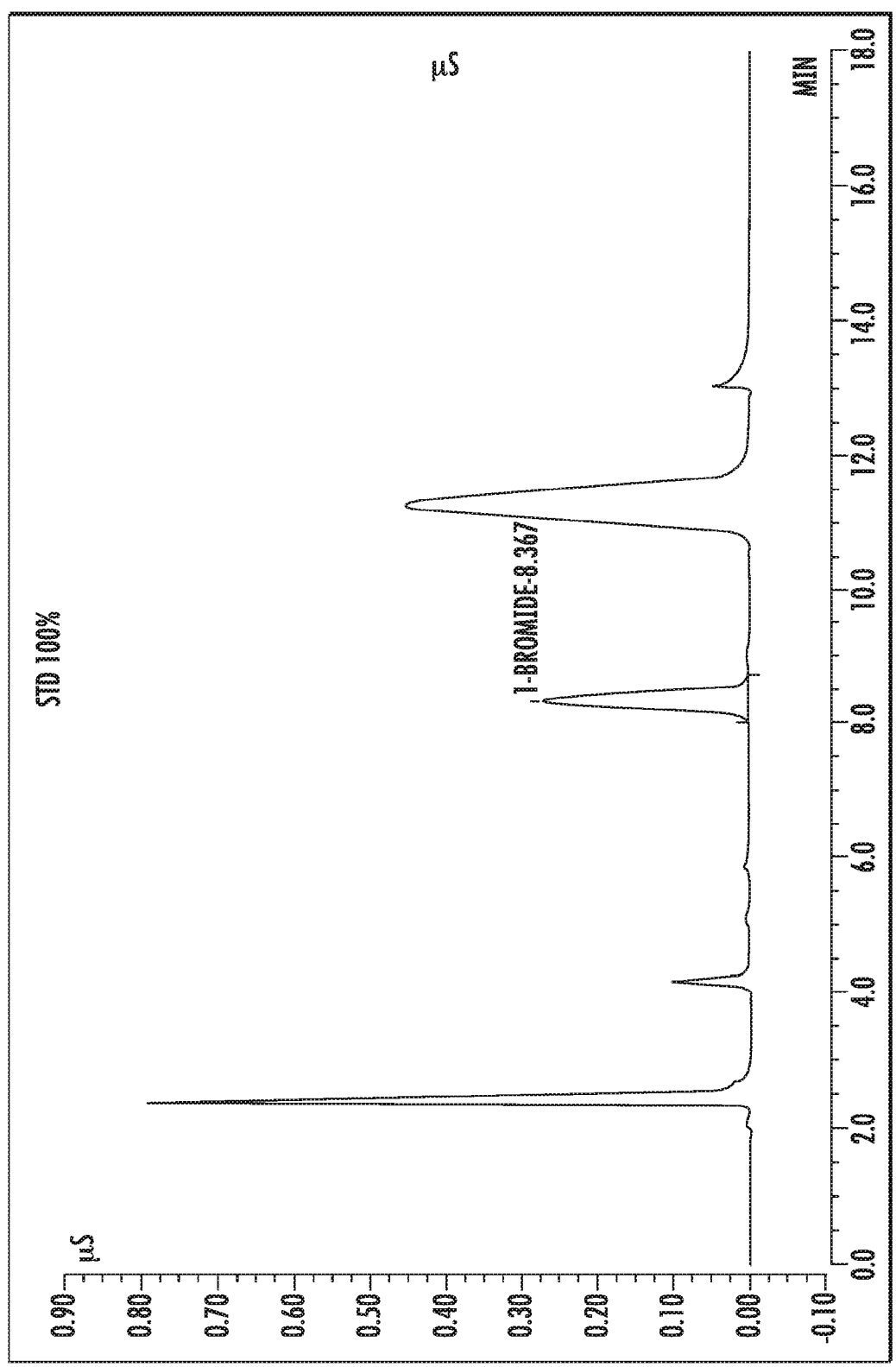
FIG. 25 shows ion chromatography data for a bromide standard.
Figure 26:
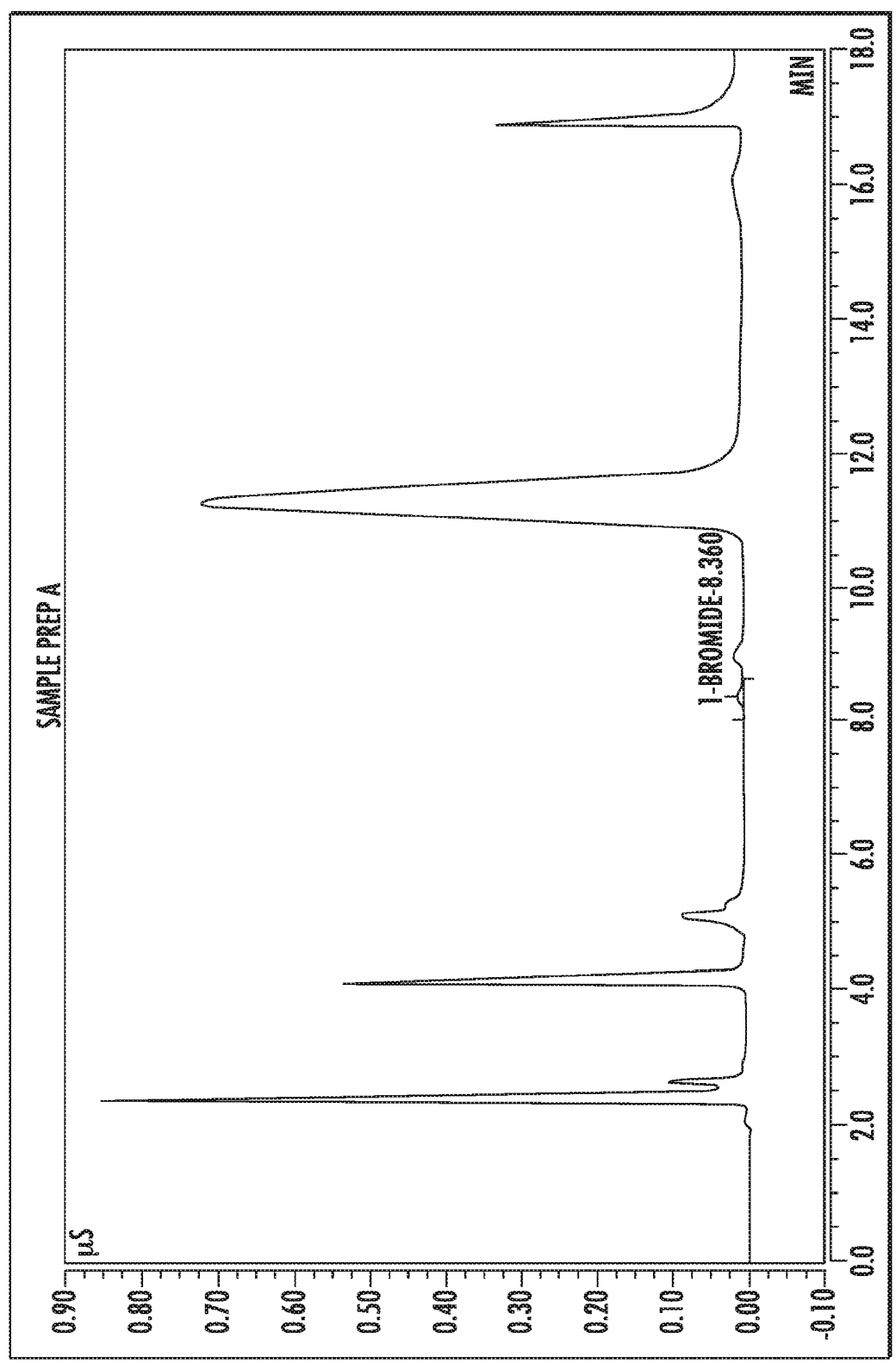
FIG. 26 shows ion chromatography data for bromide in glycopyrronium stearate.

Ion chromatography data for a bromide standard is shown in FIG. 25. Ion chromatography data for bromide in glycopyrronium stearate is shown in FIG. 26. The non-labeled peaks in FIG. 26 are the non-bromide charged species present in the sample matrix (artifacts, compare with bromide standard trace). As shown in FIG. 26, very little bromide remains in the sample, which indicates that the reaction was successful in producing the desired result, glycopyrronium stearate.

Ion Chromatography for Potassium Content

Yet another method quantitated the residual potassium (or sodium) ion in the product using ion chromatography (cation mode). The key challenges were the limited solubility of the sample in a suitable diluent and the initial observation of interfering peaks near the potassium retention time. These were resolved and the method can detect potassium ion down to a limit of quantitation of 0.1% level for a 0.5 mg/mL API sample.

Figure 27:
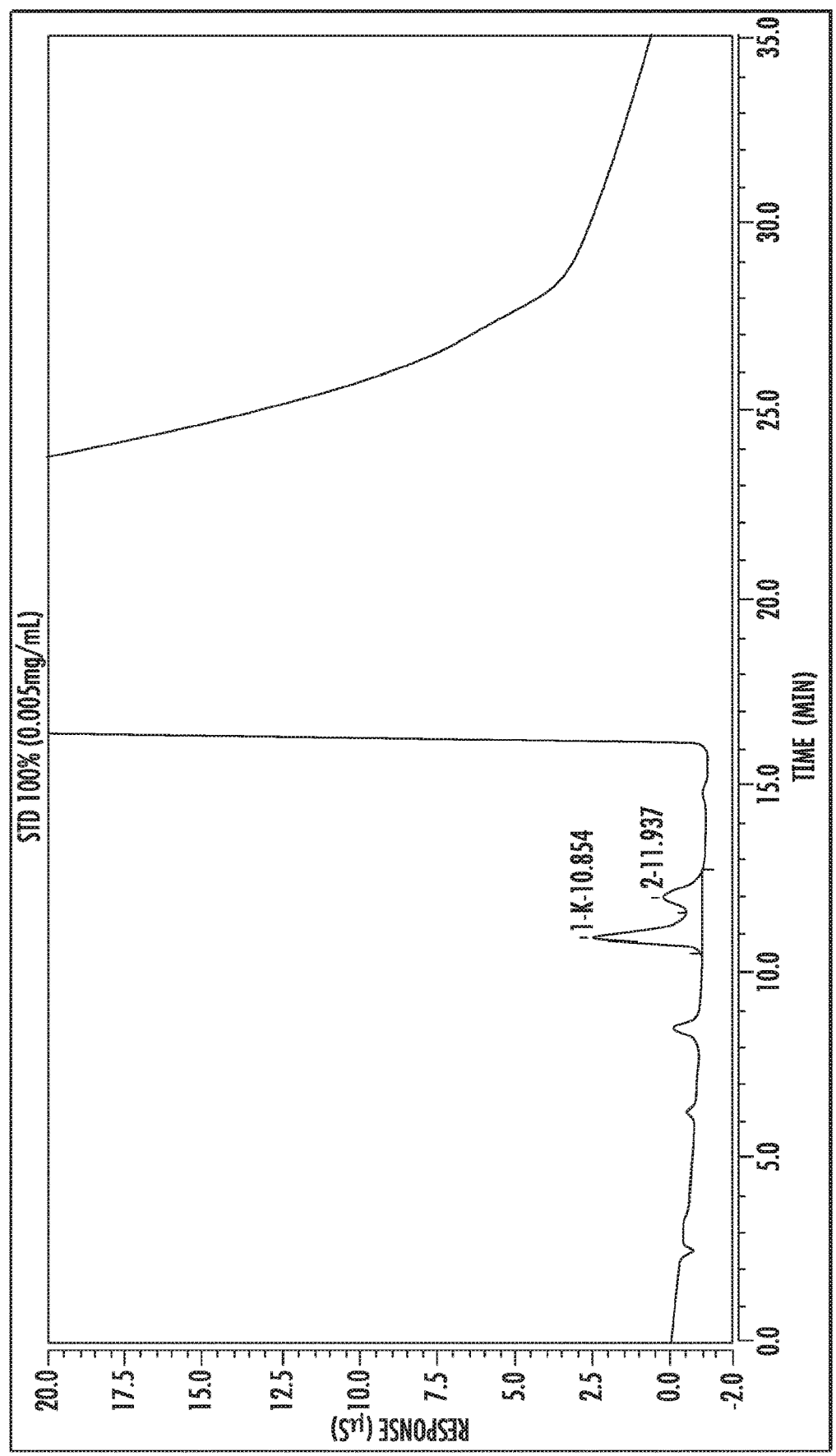
FIG. 27 shows ion chromatography data for potassium in glycopyrronium stearate.

Ion chromatography data for potassium in glycopyrronium stearate is shown in FIG. 27. Peak 1 shows potassium still present in the sample. Peak 2 is unknown, but was also present in the blank sample. As shown in FIG. 27, very little potassium remains in the sample, which indicates that the reaction was successful in producing the desired result, glycopyrronium stearate. The combination of the results shown in FIGS. 26 and 27, taken together, also indicate a successful reaction.

Gas Chromatography for Fatty Acid Content

Another analytical method that was developed was a method for quantitation of weakly- or non-chromophoric starting materials and degradants (fatty acids and derived salts, dimethylhydroxypyrrolidinium degradants). The method used a GC (FID) method to determine stearic acid content.

Gas chromatography was used to determine stearic acid content in glycopyrronium stearate. A direct injection gas chromatography method was developed for Wt % assay for stearic acid. Glycopyrronium stearate is dissolved in THF and acidified with glacial acetic acid. The method is potentially applicable to other fatty acids (with modifications to the temperature gradient). Other components of the glycopyrronium fatty acid salts mixture were not detected (but therefore also not interfering). Sample analysis gave the results shown in Table 31.

TABLE 31

| Sample | Description | Stearic Acid Content |
|---|---|---|
| EE-008-001-3a | Filterable Solids from GPBr/Stearic Acid/ Potassium Stearate (recovered portion of excess free stearic acid) | 98.3% wt. |
| EE-008-001-3b | Waxy Solids from GPBr/Stearic Acid/ Potassium Stearate (mixture of GP stearate and excess free stearic acid) | 51.45% wt. |

It is somewhat difficult to separate the excess free fatty acid from the salt. In order to determine how much excess free fatty acid is still in the mixture, one can subtract the amount bound to glycopyrronium (which can be determined using stoichiometry calculations) to get the excess. The filterable solid in Table 31 represents what precipitates out, and is predominantly the free fatty acid (stearic acid in the table). This filterable solid, which is fairly pure (98.3% by weight of stearic acid) is discarded. The desired product (glycopyrronium stearate) is in the waxy solid. While some of the excess has been filtered out in the filterable solid, the stearic acid measured in the waxy solid is both the stearic acid that is part of glycopyrronium stearate and the excess free stearic acid.

While FIGS. 9 and 10 and Table 31 only show gas chromatography results for stearic acid content, gas chromatography could also be used to quantitate other fatty acids, with minor modifications to the gas chromatography method. Some parameters that could be modified include, but are not limited to, the hold time, the injection temperature, the concentration for injection, and the time to ramp up the temperature. Alternatively, NMR results may be used to quantitate the amount of fatty acid. The amount of bound fatty acid can be determined using stoichiometry. The length of the particular fatty acids determines how much of the glycopyrronium fatty acid salt is fatty acid and how much is glycopyrronium. The gas chromatography operations are shown in Table 32.

TABLE 32

| Parameter | Condition |
| --- | --- |
| Inlet | Split; Split Ratio 50:1 |
| Inlet Temperature | 250° C. |
| Thermal Program | Initial 235° C. (hold for 30 mins isothermal) |
| Detection | Flame Ionization |
| Detector Temperature | 300° C. |
| Carrier Gas | Helium |
| Makeup Gas | Helium, 30 mL/min |
| Air Flow | 350 mL/min |
| Hydrogen Flow | 30 mL/min |
| Lit Offset | 0.5 |
| Mode | Constant flow |
| Flow | 3.1 mL/min |
| Run Time | 21 min |

Figure 28:
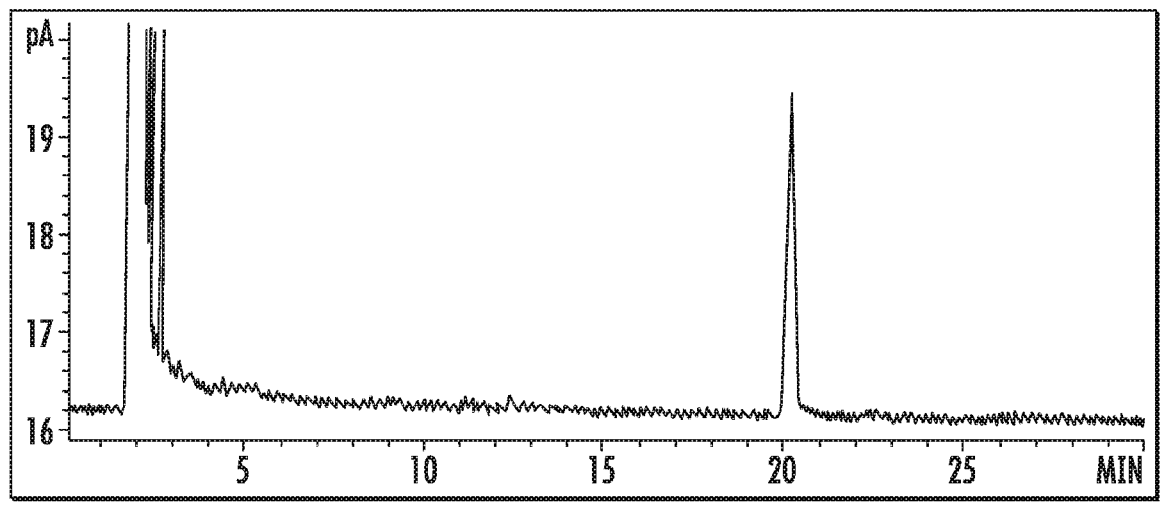
FIG. 28 shows a standard gas chromatography chromatogram for stearic acid.
Figure 29:
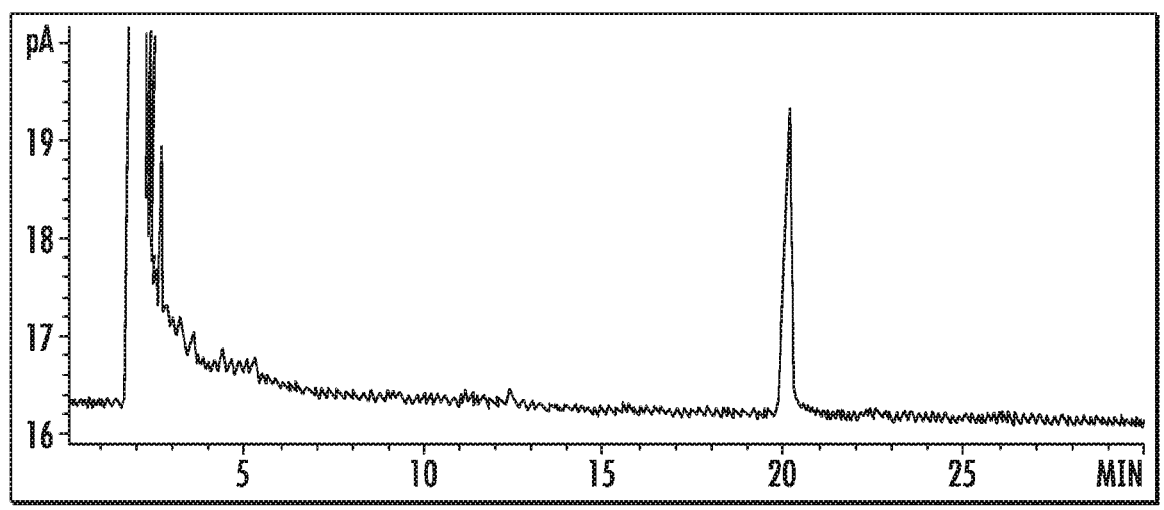
FIG. 29 shows a sample gas chromatography chromatogram for stearic acid analysis in glycopyrrolate stearate.

FIG. 28 shows a standard chromatogram and FIG. 29 shows a sample chromatogram. The approximate retention time for the peak ID for stearic acid was 20.1 minutes.

The complex mixtures that resulted from the chemical reactions to make the glycopyrronium fatty acid salts of interest were not amenable to straightforward analysis. For example, they included an oily mixture with free fatty acids. Most chromatographic methods use detection of a compound, but individual methods fell short of being able to capture the information about all of the materials (including starting materials, degradants, and final products). For example, UV can see the starting material and final product, but not the degradant QAA. The final product includes a chromophore, which is why it can be detected with UV, but the degradation product without the chromophore is not detectable with UV detection methods. Due to the chemical nature of the individual components, multiple analytical strategies were needed. Multiple methods were used, in tandem, to quantify the starting material, final product, and degradation products. Analysis may be optimized for each of the fatty acids used in the reactions.

Procedures were developed for glycopyrronium fatty acid salts and these procedures enabled the preparation of glycopyrronium fatty acid salts from a variety of fatty acids. Analysis of the fatty acid salts included various procedures. These procedures included HPLC with photodiode array detection, GC (FID) method for stearic acid, bromide content by ion chromatography (anion mode), and potassium content by ion chromatography (cation mode). In addition to these methods, analysis by NMR (in d6-DMSO) was found to be useful for the characterization of the isolated materials.

While the examples described herein predominantly discuss glycopyrronium bromide, another quaternary ammonium anti-cholinergic muscarinic receptor antagonist, for example trospium chloride, could substitute for glycopyrronium bromide in the reaction to product a quaternary ammonium fatty acid salt (for example, a trospium fatty acid salt).

In one method of manufacturing such a salt, trospium chloride is reacted with a fatty acid salt in a biphasic reaction mixture, and at least 0.2 molar equivalent of excess free fatty acid is added to the reaction mixture. The method preferably mixes a fatty acid with water, 2-methyl-tetrahydrofuran (or another appropriate solvent), and a metal hydroxide selected from the group consisting of an alkali metal hydroxide and an alkaline earth metal hydroxide, until all solids are dissolved to form the fatty acid salt. Any of the steps and variations described with respect to the glycopyrronium fatty acid salts could alternatively be used to make trospium fatty acid salts.

All cited references are incorporated by references herein.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of synthesizing at least one glycopyrronium fatty acid salt product comprising the step of mixing glycopyrronium bromide with a fatty acid salt in a biphasic reaction mixture, wherein at least a 0.2 molar equivalent of excess free fatty acid is added to the reaction mixture.

2. The method of claim 1, wherein the mixing step comprises the substep of:
   i) mixing a fatty acid with water, 2-methyl-tetrahydrofuran, and a metal hydroxide selected from the group consisting of an alkali metal hydroxide and an alkaline earth metal hydroxide, until all solids are dissolved to form the fatty acid salt.

3. The method of claim 2, wherein the mixing step further comprises the substeps of:
   ii) adding glycopyrronium bromide and mixing until solids dissolve;
   iii) removing a lower aqueous phase of the reaction mixture and retaining an upper organic phase;
   iv) washing the upper organic phase with water;
   v) repeating steps iii) and iv) at least once;
   vi) performing vacuum distillation on the upper organic phase;
   vii) adding new 2-methyl-tetrahydrofuran;
   viii) repeating step;
   vi) until no distillate is observed;
   ix) adding a non-polar hydrocarbon solvent and filtering the resulting mixture to remove any suspended solids; and
   x) performing vacuum distillation of a filtrate from step ix) to obtain the product.

4. The method of claim 3, wherein, in step v), substeps iii) and iv) are repeated at least two times.

5. The method of claim 3, wherein the non-polar hydrocarbon solvent is selected from the group consisting of n-heptane, a mixture of heptane isomers, n-hexane, isooctane, and petroleum ether.

6. The method of claim 1, wherein the product is selected from the group consisting of an oil, an oily solid, and a waxy solid.

7. The method of claim 1, wherein a cation of the fatty acid salt is selected from the group consisting of Na, K, and Ca.

8. The method of claim 1, wherein the fatty acid is selected from the group consisting of: arachidic acid, stearic acid, palmitic acid, oleic acid, erucic acid, linoleic acid, arachidonic acid, lauric acid, capric acid, linoleic acid, a-linolenic acid, y-linolenic acid and myristic acid.

9. The method of claim 1, wherein the fatty acid comprises at least eight carbon molecules.

10. The method of claim 1, wherein an isolated glycopyrronium fatty acid salt mixture has an enrichment of the fatty acid relative to glycopyrronium compared to an input ratio.

11. The method of claim 1, wherein at least a 0.6 molar equivalent of excess free fatty acid is added to the reaction mixture.

12. The method of claim 1, wherein between approximately 0.6 molar equivalent of excess free fatty acid and 1.2 molar equivalent of excess free fatty acid is added to the reaction mixture.

13. The method of claim 1, wherein at least a 1.1 molar equivalent of excess free fatty acid is added to the reaction mixture.

14. The method of claim 1, wherein approximately 1.2 molar equivalent of excess free fatty acid is added to the reaction mixture.

15. The method of claim 14, wherein a ratio of the fatty acid relative to glycopyrronium of an isolated glycopyrronium fatty acid salt mixture is between approximately 2.25:1 and 3.00:1.

16. The method of claim 15, wherein a ratio of the fatty acid relative to glycopyrronium of an isolated glycopyrronium fatty acid salt mixture is between approximately 2.29:1 and 2.87:1.

17. The method of claim 1, wherein the biphasic reaction mixture comprises water and 2-methyl-tetrahydrofuran.

18. The method of claim 1, further comprising the step of analyzing the glycopyrronium fatty acid salt product, comprising the substeps of:
  i) performing high pressure liquid chromatography to quantitate a glycopyrronium component and a hydrolysis degradant, Acid A, present in the product;
  ii) performing gas chromatography to quantitate a total fatty acid component in the product;
  iii) performing anion mode ion chromatography to quantitate a bromide component in the product;
  iv) performing cation mode ion chromatography to quantitate a potassium component in the product;
  v) performing stoichiometric calculations combining the results from substeps i), ii), iii), and iv) to determine an amount of excess free fatty acid and an amount of a quaternary amino alcohol degradant; and
  vi) performing nuclear magnetic resonance to determine a molar ratio of glycopyrronium to total fatty acid in the product.

19. A method of synthesizing trospium fatty acid salts comprising the step of mixing trospium chloride with a fatty acid salt in a biphasic reaction mixture, wherein at least a 0.2 molar equivalent of excess free fatty acid is added to the reaction mixture.

20. The method of claim 19, wherein the mixing step comprises the substep of:
  i) mixing a fatty acid with water, 2-methyl-tetrahydrofuran, and a metal hydroxide selected from the group consisting of an alkali metal hydroxide and an alkaline earth metal hydroxide, until all solids are dissolved to form the fatty acid salt.

* * * * *